(12) United States Patent
Ziv

(10) Patent No.: US 9,889,202 B2
(45) Date of Patent: *Feb. 13, 2018

(54) COMPOUNDS AND METHODS FOR TRANS-MEMBRANE DELIVERY OF MOLECULES

(71) Applicant: Aposense LTD., Petach-Tikva (IL)

(72) Inventor: Ilan Ziv, Kfar Saba (IL)

(73) Assignee: Aposense LTD., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/872,179

(22) Filed: Oct. 1, 2015

(65) Prior Publication Data

US 2016/0129125 A1     May 12, 2016

Related U.S. Application Data

(63) Continuation-in-part of application No. 14/870,406, filed on Sep. 30, 2015, which is a continuation-in-part
(Continued)

(51) Int. Cl.
*A61K 47/48*     (2006.01)
*A61K 38/46*     (2006.01)
(Continued)

(52) U.S. Cl.
CPC ...... *A61K 47/48123* (2013.01); *A61K 38/465* (2013.01); *C07F 9/2408* (2013.01);
(Continued)

(58) Field of Classification Search
CPC .................................................. A61K 31/481
(Continued)

(56) References Cited

U.S. PATENT DOCUMENTS 6,028,066 A     2/2000  Unger
8,809,514 B2    8/2014  Yamada et al.
(Continued)

FOREIGN PATENT DOCUMENTS

FR      2846969          5/2004
WO     WO 97/40679      11/1997
(Continued)

OTHER PUBLICATIONS

Kraft, Adv. Drug Delivery Rev. (2001), vol. 47, pp. 209-228.*
(Continued)

*Primary Examiner* — Taofiq A Solola
(74) *Attorney, Agent, or Firm* — Pearl Cohen Zedek Latzer Baratz LLP

(57) ABSTRACT

A novel delivery system for drugs, and especially macromolecules such as proteins or oligonucleotides through biological membranes is provided, and specifically delivery of siRNA The delivery system comprises conjugation of the macromolecule drug to a moiety that enables effective passage through the membranes. Respectively, novel compounds and pharmaceutical compositions are provided, utilizing said delivery system. In one aspect of the invention, the compounds may be utilized in medical practice, for example, in delivery of siRNA or antisense oligonucleotides across biological membranes for the treatment of medical disorders.

30 Claims, 18 Drawing Sheets
(15 of 18 Drawing Sheet(s) Filed in Color)

Related U.S. Application Data of application No. 14/830,799, filed on Aug. 20, 2015, which is a continuation-in-part of application No. PCT/IL2015/000019, filed on Mar. 29, 2015.

(60) Provisional application No. 61/978,903, filed on Apr. 13, 2014, provisional application No. 62/002,870, filed on May 25, 2014, provisional application No. 62/008,509, filed on Jun. 6, 2014, provisional application No. 62/091,551, filed on Dec. 14, 2014, provisional application No. 61/971,548, filed on Mar. 28, 2014.

(51) Int. Cl.
| | |
|---|---|
| C07F 9/6553 | (2006.01) |
| C07F 9/6558 | (2006.01) |
| C07F 9/24 | (2006.01) |
| C07J 1/00 | (2006.01) |
| C07J 9/00 | (2006.01) |
| C07J 41/00 | (2006.01) |
| C07J 51/00 | (2006.01) |
| C12N 15/11 | (2006.01) |
| C07J 31/00 | (2006.01) |

(52) U.S. Cl.
CPC .... *C07F 9/65586* (2013.01); *C07F 9/655363* (2013.01); *C07J 1/0077* (2013.01); *C07J 9/00* (2013.01); *C07J 41/0072* (2013.01); *C07J 51/00* (2013.01); *C12N 15/111* (2013.01); *C12Y 301/00* (2013.01); *C07J 9/005* (2013.01); *C07J 31/006* (2013.01); *C12N 2310/11* (2013.01); *C12N 2310/14* (2013.01); *C12N 2320/32* (2013.01)

(58) Field of Classification Search
USPC .......................................................... 549/21
See application file for complete search history.

(56) References Cited

U.S. PATENT DOCUMENTS

2011/0123457 A1   5/2011   Yu
2015/0141678 A1   5/2015   Payne et al.

FOREIGN PATENT DOCUMENTS

WO    WO98/50041     11/1998
WO    WO2005/077968   8/2005

OTHER PUBLICATIONS

Vierling et al., J. Fluorine Chem. (2001), vol. 107, pp. 337-354.*
Reiss, Tetrahed. (2002), vol. 58, pp. 4113-4131.*
Alconcel et al., Polym. Chem. (2011), vol. 2, pp. 1442-1448.*
Shengguo Sun; Adejare, Adeboye "Fluorinated Molecules as Drugs and Imaging Agents in the CNS" Current Topics in Medicinal Chemistry; vol. 6 Issue 14, p. 1457-64 , Jul. 2006.
International Search Report for Application No. PCT/IL2015/000019, dated Jul. 28, 2015.
Andersen, Olaf Sparre, et al. "Effect of phloretin on the permeability of thin lipid membranes." The Journal of general physiology 67.6 (1976): pp. 749-771.
Ikumi, Yusuke, et al. "Polymer-phloridzin conjugates as an antidiabetic drug that Inhibits glucose absorption through the Na+/glucose cotransporter (SGLT1) in the small intestine." Journal of controlled release 125.1 (2008): pp. 42-49.
Üllen, Andreas, et al. "Covalent adduct formation between the plasmalogen-derived modification product 2-chlorohexadecanal and phloretin." Biochemical pharmacology 93.4 (2015): pp. 470-481.
International Search Report for PCT Application No. PCT/IL2016/50893 dated Dec. 28, 2016.
Bellucci, Maria Cristina, and Alessandro Volonterio. "Multicomponent Synthesis of Peptide-Sugar Conjugates Incorporating Hexafluorovaline." Advanced Synthesis & Catalysis 352.16 (2010): pp. 2791-2798.
Janout, Vaclav, et al. "Molecular umbrella conjugate for the ocular delivery of siRNA." Bioconjugate chemistry 25.2 (2014): pp. 197-201.
Grijalvo, Santiago, et al. "Synthesis of oligonucleotides carrying amino lipid groups at the 3'-end for RNA interference studies." The Journal of organic chemistry 75.20 (2010): pp. 6806-6813.
Yue, Xuyi, Yue Feng, and Y. Bruce Yu. "Synthesis and characterization of fluorinated conjugates of albumin." Journal of Fluorine Chemistry 152 (2013): pp. 173-181.
Jiang, Zhong-Xing, and Y. Bruce Yu. "The design and synthesis of highly branched and spherically symmetric fluorinated macrocyclic chelators." Synthesis 2008.02 (2008): pp. 215-220.
Blazejewski., et al. "Synthesis, characterization and biological evaluation of 7α-perfluoroalkylestradiol derivatives." Bioorganic & medicinal chemistry 11.3 (2003): pp. 335-345.
Schiller, R., A. P. Funke, and C. Günther. "DSC measurements on full thickness mice skin." Journal of Thermal Analysis and Calorimetry 77.2 (2004): 497-510.
Extended European Search Report for EP Application No. 15770224 dated Sep. 22, 2017.

* cited by examiner (i).

(ii).

(i).

(ii).

(i).

(ii).

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens
<220> FEATURE:
<221> NAME/KEY: misc_feature
<222> LOCATION: (1)..(1)
<223> OTHER INFORMATION: c is attached to Apo-si-TT-iCy3

<400> SEQUENCE: 1
cggtggtgca gatgaacttc agggtca                                            27

<210> SEQ ID NO 2
<211> LENGTH: 29
<212> TYPE: DNA
<213> ORGANISM: Homo sapiens
<220> FEATURE:
<221> NAME/KEY: misc_feature
<222> LOCATION: (1)..(1)
<223> OTHER INFORMATION: t is attached to Apo-si

<400> SEQUENCE: 2
tgaccctgaa gttcatctgc accaccgaa                                          29

<210> SEQ ID NO 3
<211> LENGTH: 25
<212> TYPE: RNA
<213> ORGANISM: Homo sapiens

<400> SEQUENCE: 3
acccugaagu ucaucugcac caccg                                              25

<210> SEQ ID NO 4
<211> LENGTH: 27
<212> TYPE: RNA
<213> ORGANISM: Homo sapiens

<400> SEQUENCE: 4
cgguggugca gaugaacuuc aggguca                                            27
```

COMPOUNDS AND METHODS FOR TRANS-MEMBRANE DELIVERY OF MOLECULES

CROSS-REFERENCE TO RELATED APPLICATIONS

This application is a continuation-in-part of U.S. application Ser. No. 14/870,406, filed on Sep. 30, 2015, which is a continuation-in-part of U.S. application Ser. No. 14/830,799, filed on Aug. 20, 2015, which is a continuation-in-part of PCT International Application No. PCT/IL2015/000019, International Filing Date Mar. 29, 2015, claiming the benefit of US Provisional Patent Applications Nos. 61/971,548, filed Mar. 28, 2014, 61/978,903, filed Apr. 13, 2014, 62/002,870, filed May 25, 2014, 62/008,509 filed Jun. 6, 2014, and 62/091,551, filed Dec. 14, 2014, which are hereby incorporated by reference.

FIELD OF THE INVENTION

The invention relates to a novel delivery system and methods for delivery of molecules and macromolecules across biological membranes into cells, optionally with subsequent intracellular entrapment.

BACKGROUND

Protein pathology is a common denominator in the etiology or pathogenesis of many medical disorders, ranging from malfunction of a mutated protein, to pathological gain of function where a specific protein acquires a novel property, which renders it toxic. Conceptually, inhibition of the synthesis of these of proteins by gene therapy may hold promise for patients having such protein anomaly.

One of the major advances of recent years is the concept of silencing a specific gene by RNA interference, using small interfering RNA (siRNA). RNA interference is based on short (≈19-27 base pairs), double-stranded RNA sequences (designated siRNA), capable of acting, in concert with cellular biological systems [among others, the Dicer protein complex which cleaves double-stranded RNA to produce siRNA, and the RNA-induced silencing complex (RISC)], to inhibit translation and mark for degradation specific mRNA sequences, thus inhibiting gene expression at the translational stage. The use of antisense oligonucleotide (ASO), being a short sequence (usually 13-25 nucleotides) of unmodified or chemically modified DNA molecules, complementary to a specific messenger RNA (mRNA), has also been used to inhibit the expression and block the production of a specific target protein.

However, albeit the tremendous potential benefits of such approaches for medical care, delivery of such macromolecules into cells remains a substantial challenge, due to the relatively large and highly-charged structures of oligonucleotides (for example, siRNA has an average molecular weight of 13 kD, and it carries about 40 negatively-charged phosphate groups). Therefore, trans-membrane delivery of oligonucleotides requires overcoming a very large energetic barrier.

The membrane dipole potential is an electric potential that exists within any phospholipid membrane, between the water/membrane interface and the membrane center (positive inside). It is assumed to be generated by the highly ordered carbonyl groups of the phospholipid glyceryl esteric bonds, and its amplitude is about 220-280 mV. Since the membrane dipole potential resides in a highly hydrophobic environment of dielectric constant of 2-4, it translates into a very strong electric field of $10^8$-$10^9$ V/m. Conceivably, the membrane dipole potential and related intra-membrane electric field are highly important for the function of membrane proteins, determining the conformation and activity of membrane proteins. However, to the best of our knowledge, to date, the dipole potential has not been recruited for drug development.

Various methods have been developed for delivery of macromolecules such as oligonucleotides or proteins across biological membranes. These methods include viral vectors, as well as non-viral delivery systems, such as cationic lipids or liposomes. However to date, use of these methods has been largely limited to applications in vitro, or to focal administration in vivo, for example, by direct injection into the eye or direct administration into the lung. Efficient delivery has also been achieved to the liver. Among these methods, electroporation is an effective and widely-used method for delivery of macromolecules in vitro. According to this method, an external electric field is applied to a cell suspension, leading to collision of charged target molecules with the cell membrane, subsequent temporary and focal membrane destabilization, and consequent passage of the macromolecules into the cell. However, as described above, electroporation is mainly used in vitro. Electroporation in vivo encounters limited success, and was attempted only to specific organs (e.g., muscle, lung), where external electrodes could be inserted into the target organ.

In conclusion, delivery of macromolecules, such as oligonucleotides or proteins through cell membranes, or through other biological barriers, such as the Blood-Brain-Barrier, Blood-Ocular-Barrier or Blood-Fetal-barrier still presents a substantial unmet need, and systemic delivery of therapeutic macromolecules, still remains a huge, unaddressed challenge.

SUMMARY OF THE INVENTION

Embodiments of the present invention provide a novel delivery system, based on a novel, rationally-designed "Molecular NanoMotors (MNMs)". The MNMs according to embodiments of the invention have the structure of moiety E, E' or E" as set forth in Formula (II) below. The drugs to be delivered by the MNMs may be small-molecule drugs, or macromolecules such as peptides, proteins or oligonucleotides (e.g., single-stranded or double-stranded, RNA or DNA). In an embodiment of the invention, the macromolecules to be delivered may include RNA strands for gene silencing, i.e., siRNA (small interfering RNA), or DNA sequences designed to serve as antisense oligonucleotides (ASO).

Conjugates of drugs (e.g., small molecule drugs or macromolecules) with MNMs according to embodiments of the invention may be utilized in basic research or clinical medical practice, among others, for treatment of medical disorders, where aberrant proteins or protein dysfunction play a role, and where silencing the expression of genes encoding for these proteins can be beneficial; for example, in the treatment of degenerative disorders, cancer, toxic or ischemic insults, infections, or immune-mediated disorders.

Conjugates according to embodiments of the invention have the general Formula (I):

Formula (I)

$E_y\text{—}D\begin{smallmatrix}E'_z\\E''_w\end{smallmatrix}$ including pharmaceutically acceptable salts, hydrates, solvates and metal chelates of the compound represented by the structure as set forth in Formula (I), and solvates and hydrates of the salts, wherein:

D is a drug to be delivered across biological membranes. D may be a small-molecule drug, a peptide, a protein, or a native or modified, single-stranded or double-stranded DNA or RNA, such as ASO or siRNA;

y, z and w are each an integer, independently selected from 0, 1, 2, 3, 4, 5, 6, wherein at least one of y, z or w is different from 0. In one embodiment, y=1, z=o and w=0; in another embodiment y=1, z=1 and w=0.

E, E' or E" can be the same or different, each having the structure as set forth in general Formula (II):

$$(A)_a\text{-}B\text{-}L_1\text{-}Q_1\text{-}L_2\text{-}Q_2\text{-}L_3 \quad \text{Formula (II)}$$

where A is selected from the structures as set forth in Formulae (III), (IV), (V) and (VI):

Formula (III)

Formula (IV)

Formula (V)

Formula (VI)

M is selected from —O— or —CH$_2$—; and g, h and k are each individually an integer selected from 0, 1, 2, 3, 4, 5, 6, 7, 8, 9, 10, 11, 12, 13, 14, 15 and 16; * is —H, or the point of linkage to B; a is an integer, selected from 1, 2, 3 or 4;

B is selected from the group consisting of:
  linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkyl or heteroalkyl;
  linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene;
  $C_5$, $C_6$, $C_7$, $C_8$, $C_9$, $C_{10}$, $C_{11}$, $C_{12}$, $C_{13}$ or $C_{14}$ aryl or heteroaryl;
  one or more steroid moiety (such as, cholesterol, bile acid, estradiol, estriol), estrogen, nucleoside, nucleotide; and any combination thereof;
  wherein each group is optionally substituted by hydroxyl, amine, or thiol;

$Q_1$ and $Q_2$ are each independently an optionally cleavable group, selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], imidazole, triazole, a pH-sensitive moiety, a redox-sensitive moiety; a metal chelator, including its chelated metal ion; and any combinations thereof;

$L_1$, $L_2$ and $L_3$ are each independently selected from null and the group consisting of:
  linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkyl or hetero-alkyl;
  linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene;
  $C_5$, $C_6$, $C_7$, $C_8$, $C_9$, $C_{10}$, $C_{11}$, $C_{12}$, $C_{13}$ or $C_{14}$ aryl or heteroaryl;
  —(O—CH$_2$—CH$_2$)$_u$—, wherein u is an integer of 1, 2, 3, 4, 5;
  nucleoside, nucleotide; imidazole, azide, acetylene; and any combinations thereof;
  wherein each group is optionally substituted by one or more hydroxyl, amine, or thiol;

wherein each of $Q_1$, $Q_2$, $L_1$, $L_2$ and $L_3$ is optionally substituted by T; wherein T is an initiator group, selected from $C_5$, $C_6$, $C_7$-1,2-dithiocycloalkyl(1,2-dithiocyclo-pentane, 1,2-dithiocyclohexane, 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); and T optionally comprises an amine group.

In another embodiment, there is provided a molecule according to general Formula (I), which includes E, E' or E", having the structure as set forth in Formulae (XI):

Formula (XI)

including pharmaceutically acceptable salts, hydrates, solvates and metal chelates of the compound represented by the structure as set forth in Formulae (XI) and solvates and hydrates of the salts.

Some embodiments of the invention relate to a method for delivery of a drug across a biological membrane into cells, either in vitro or in vivo, the method comprising contacting the cells with a Conjugate as described herein.

Another embodiment, relates to a method for treating a medical disorder in a patient in need thereof; the method comprises administration to the patient in need therapeutically efficient amounts of a pharmaceutical composition, comprising a Conjugate as described herein.

In some embodiments of the invention, the medical disorder is cancer.

BRIEF DESCRIPTION OF THE FIGURES

The patent or application file contains at least one drawing executed in color. Copies of this patent or patent application publication with color drawings will be provided by the Office upon request and payment of the necessary fee.

The invention will now be described in connection with certain Examples and embodiments, in a non-limiting manner, with reference to the following illustrative figures, so that it can be more fully understood. In the drawings:

FIG. 5a-5f: 3T3-cells:

FIG. 5a shows fluorescent microscopy of delivery of a Conjugate, comprising a 29-mer, single-stranded DNA (ss-DNA) across biological membranes of 3T3 cells, expressing the EGFP Protein (3T3-EGFP cells) in vitro;

FIG. 5b shows quantification of the delivery as described in FIG. 5a by flow cytometric analysis (FACS), presented as a dot plot;

FIG. 5c shows quantification by ELISA reader of the delivery as described in FIG. 5a, at 24 hours of incubation;

FIG. 5d shows fluorescent microscopy of delivery of a conjugate, comprising a 58-mer double-strand DNA (ds-DNA) across biological membranes of 3T3 cells, expressing the EGFP Protein (3T3-EGFP cells) in vitro;

FIG. 5e shows quantification of the delivery as described in FIG. 5d, by flow cytometric analysis (FACS): (i). Dot plot; (ii). Histogram;

FIG. 5f shows delivery as described in FIG. 5d, detected by confocal microscopy, confirming that the delivery of a Conjugate of the invention, comprising a 58-mer double-stranded DNA is into the cytoplasm of the 3T3-EGFP cells.

FIG. 6a-6c: Murine Melanoma B16 Cells:

FIG. 6a presents fluorescent microscopy of the delivery of a Conjugate of the invention, comprising a 58-mer double-stranded DNA, across biological membranes of B16 melanoma cells in vitro: (i). Control; (ii). A Conjugate comprising MNMs;

FIG. 6b shows quantification of the delivery as described in FIG. 6a, by flow cytometric analysis (dose/response);

FIG. 6c shows delivery as described in FIG. 6a, detected by confocal microscopy, confirming that the delivery of the conjugate, comprising a 58-mer double-strand DNA, is into the cytoplasm of the B16 cells.

FIG. 7: Murine C26 Colon Carcinoma Cells:

Flow cytometric analysis of the delivery of a Conjugate of the Invention, comprising a 58-mer double-stranded DNA, across the biological membranes of C26 cells in vitro.

Figure 8:
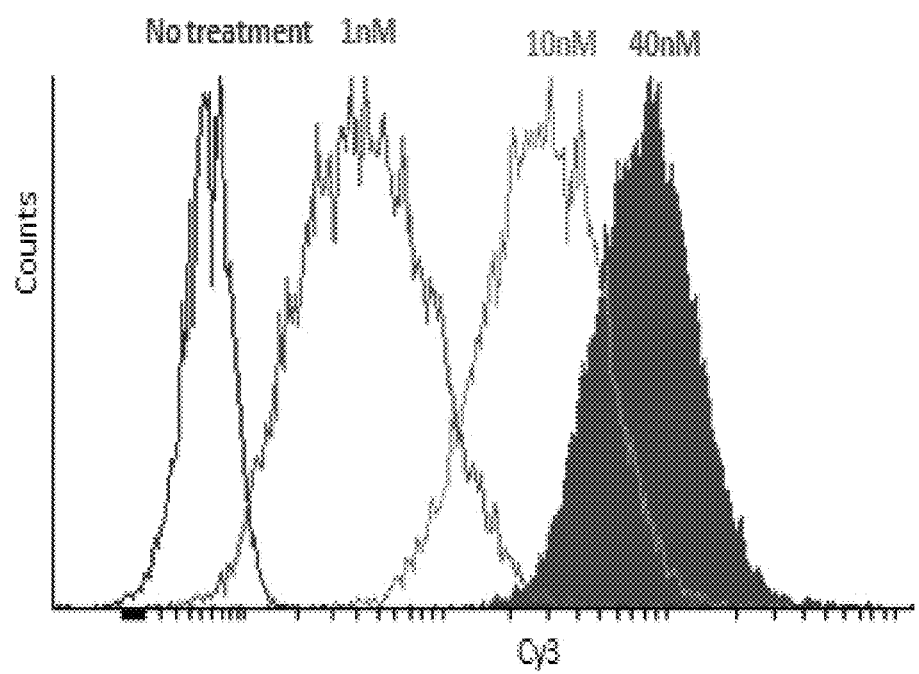

FIG. 8: HeLa Cells:

Flow cytometric analysis, of the delivery of a conjugate comprising a 58-mer double-stranded DNA across the biological membranes of HeLa cells in vitro; dose/response.

Figure 9:
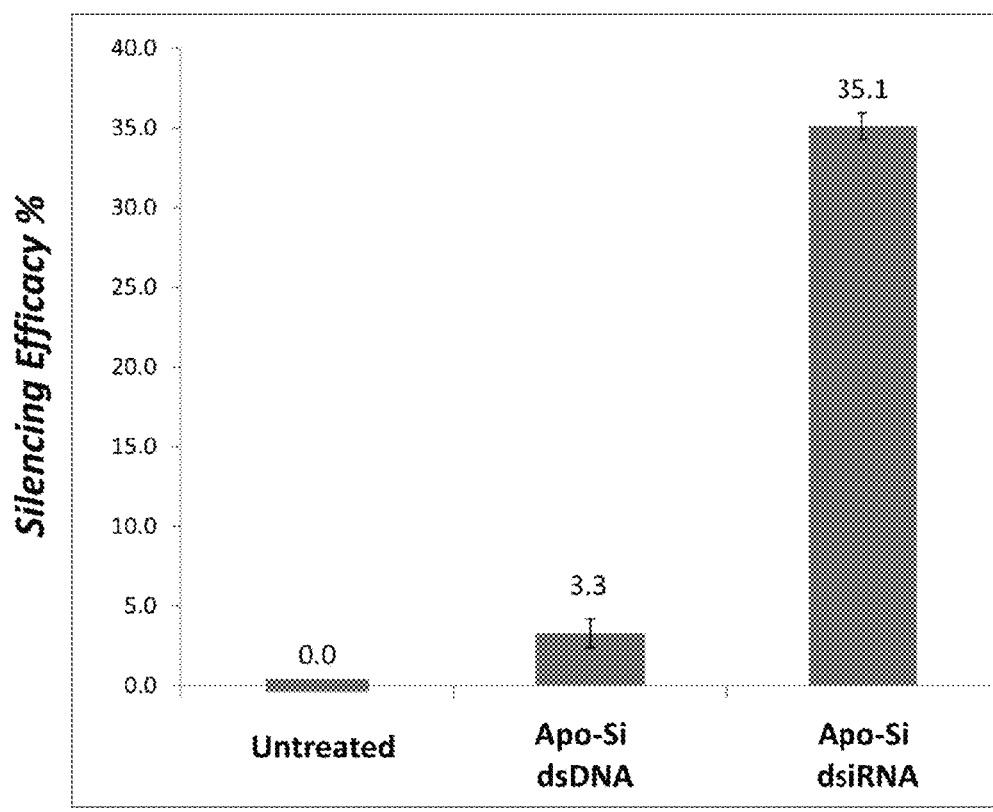

FIG. 9: Gene silencing (EGFP gene), exerted in human HeLA cells by a Conjugate of the invention, being a respective siRNA, specifically-designed to silence the EGFP gene, linked to two MNMs, each having the structure as set forth in Formula (XVI) (mean±SEM).

Figure 10:
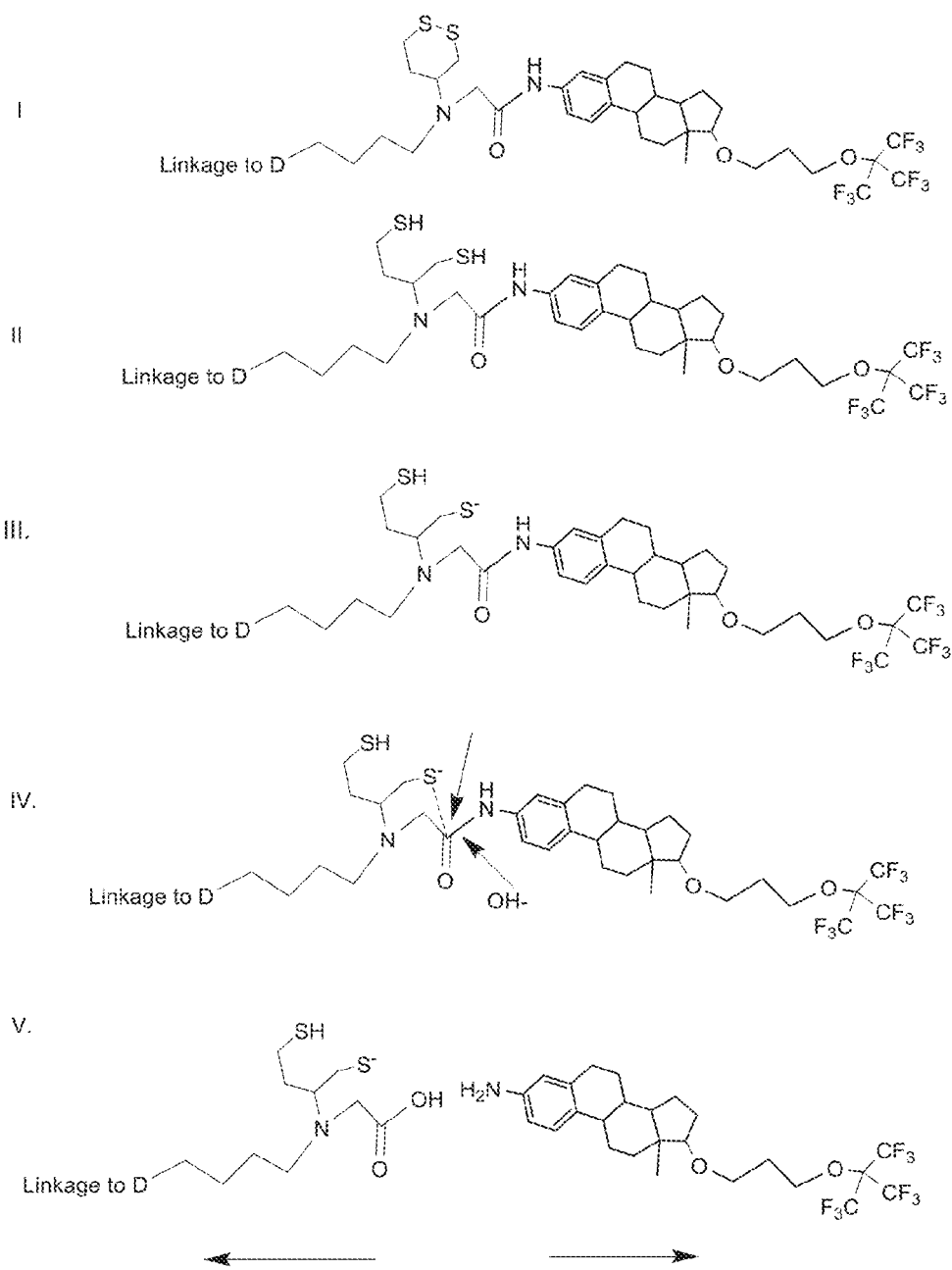

FIG. 10: Mechanism of redox-sensitive cleavage of the Conjugate of the Invention according to Formula (XI), with release of the cargo drug D in the cytoplasm.

DETAILED DESCRIPTION OF THE INVENTION

Embodiments of the present invention relate to novel Conjugates, comprising a delivery system for drugs across biological membranes into the cytoplasm, or through biological barriers, such as, the blood-brain-barrier (BBB), the blood-ocular barrier (BOB), or the blood-fetal-barrier (placental-blood-barrier). Compounds according to embodiments of the invention comprise novel, rationally-designed "Molecular NanoMotors (MNMs)", rationally-designed to move within phospholipid membranes, from the membrane/water interface to the membrane core, utilizing the internal membrane electric field, generated by the membrane dipole potential. When attached to a drug, the delivery system acts to re-locate the drug towards the membrane center, thus assisting in its trans-membrane movement. Among others, this delivery system is designed for the delivery of therapeutic macromolecules: proteins or oligonucleotides, the latter being single or double-stranded DNA or RNA. Among others, the delivery system is designed for the delivery of antisense oligonucleotides (ASO), siRNA or therapeutic proteins, such as, for example without limitation, the Cas9 protein or antibodies.

Figure 1A:
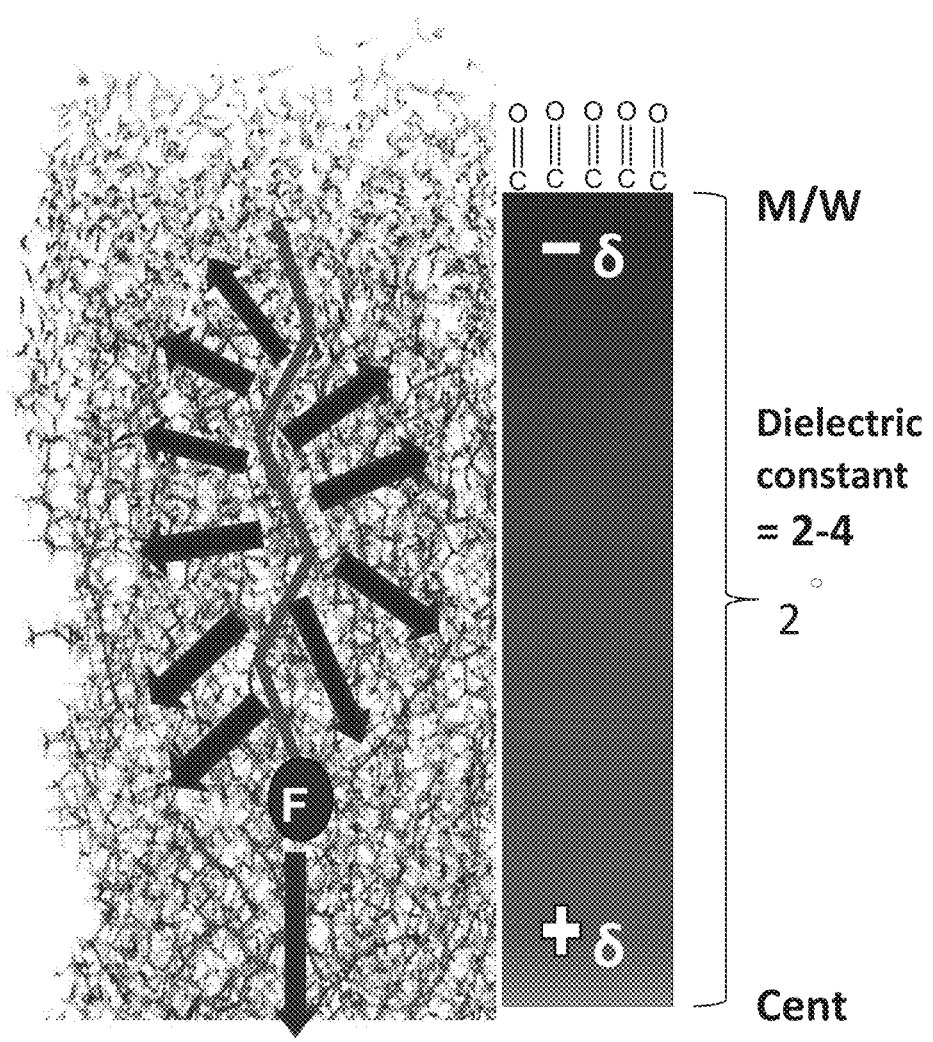
FIG. 1a is a schematic presentation of the principle of asymmetrical polarity, underlying the putative Mechanism Of Action (MOA) of compounds according to embodiments of the invention.

Proposed in a non-limiting manner, one of the principles underlying the structures of MNMs according to embodiments of the invention is the principle of "asymmetrical polarity". This principle relates to hydrophobic, uncharged molecules, that according to their log P are capable of partitioning into biological membranes, [for example without limitation, having a log P value>1 (see FIG. 1 A)]. In addition, these molecules are polar, and have their partial charges distributed in an uneven manner: the partial negative charge is highly focused and localized, while the partial positive charge is dispersed along hydrocarbon chains within the molecule. Furthermore, upon interaction with the phospholipid membrane, the partial positive charge is also masked, through London type hydrophobic interactions, taking place between hydrocarbon chains of the molecule and adjacent hydrocarbon chains of the phospholipid milieu (London dispersion forces). Consequently, as schematically illustrated in FIG. 1A, the molecules of the invention are capable of moving in the membrane milieu. Since the internal membrane electric field has a negative pole at the membrane/water interface, and a positive pole at the membrane center, the molecules of the invention move toward the membrane center, and when attached to a cargo (e.g., a drug such as siRNA, ASO, a therapeutic protein or another medicament), the cargo is re-located onto the membrane center. This movement may facilitate the trans-membrane movement of the cargo molecule in several ways. Among others, it may enforce proximity of a charged macro-molecule to the phospholipid headgroups (PLHG), perturb the hydration shells around the PLHG, and thus force lateral movement of the PLHG. Formation of transient pores within the membrane may then takes place, with passage of the cargo drug through these pores into the cell. Subsequent spontaneous closure of these transient pores may then take place, thus sealing the membrane pore, with membrane healing (FIG. 2).

Figure 1B:
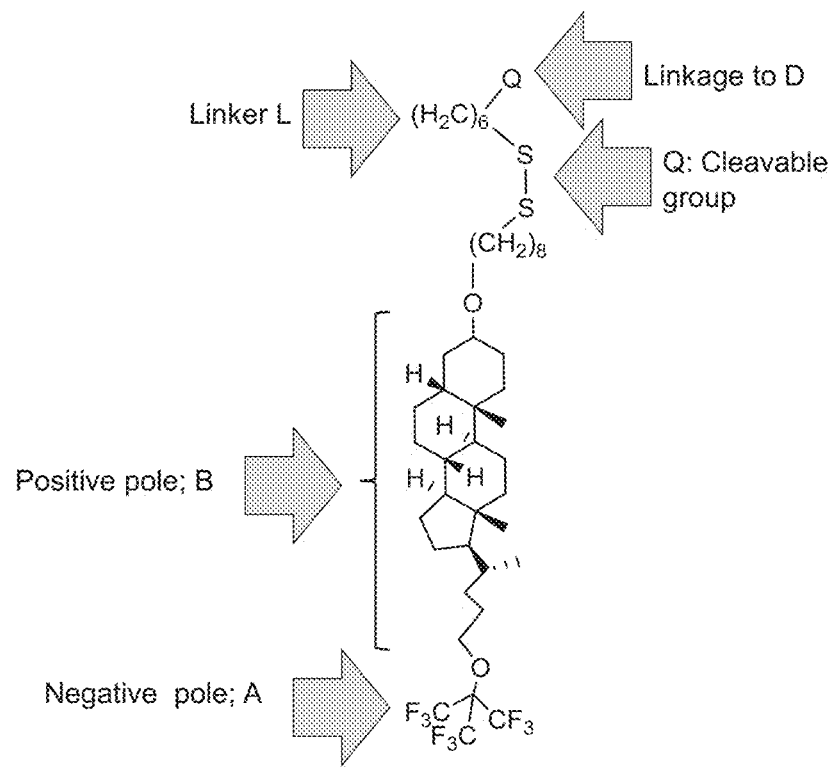
FIG. 1b schematically depicts structural motifs of the molecules of the invention, as exemplified by a compound according to Formula (VII), wherein $Q_1$ is —S—S—; and $Q_2$ is null.
Figure 2:
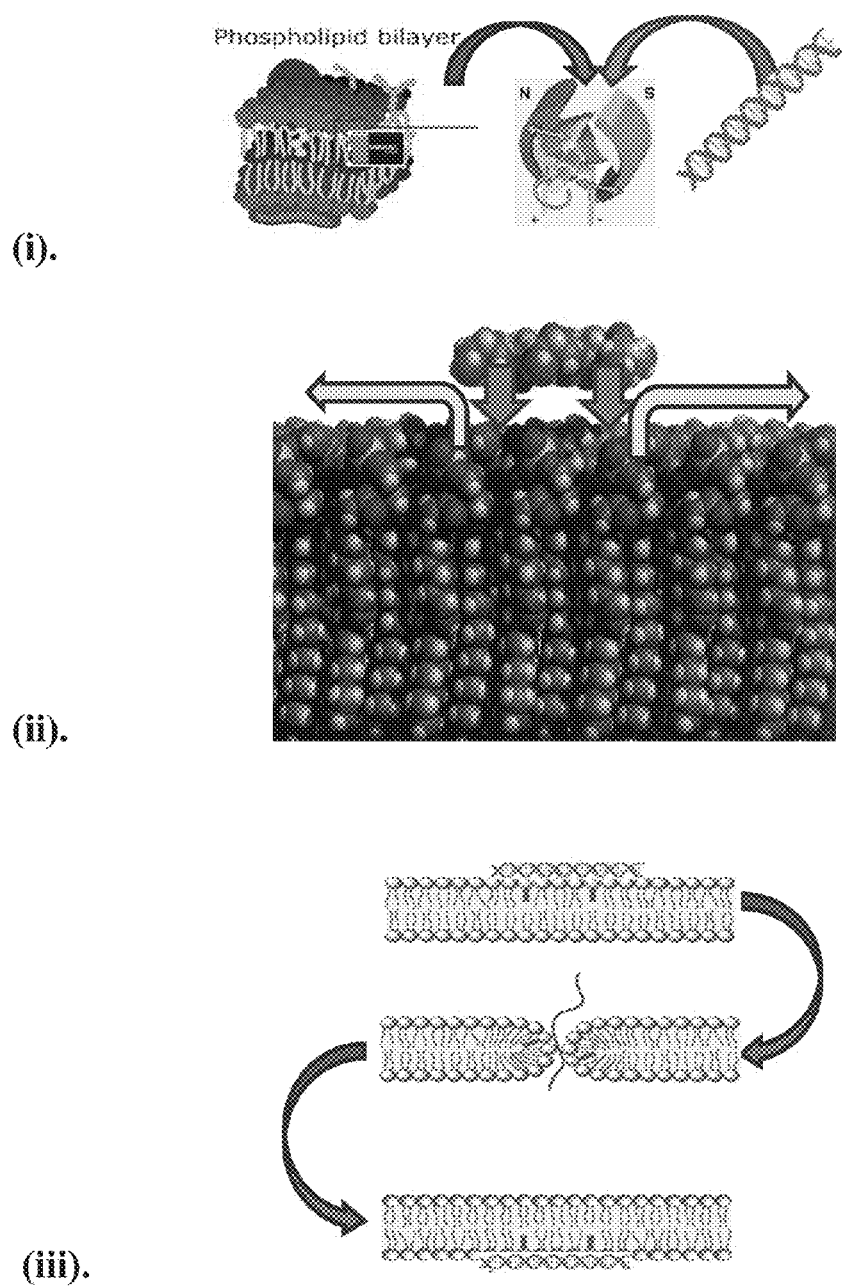
FIG. 2 schematically illustrates a putative MOA of a conjugate according to embodiments of the invention: (i). A "Molecular NanoMotor (MNM)", energized by the internal membrane electric field, which relates to the membrane dipole potential; (ii). Forced proximity of the macromolecule to the membrane surface induced by the MNM, forcing lateral movement of the phospholipid head-groups; (iii). Subsequent formation of transient membrane pores, through which there is movement of the macromolecules into the cell. This is followed by spontaneous closure of the membrane pore and membrane healing.
Figure 3:
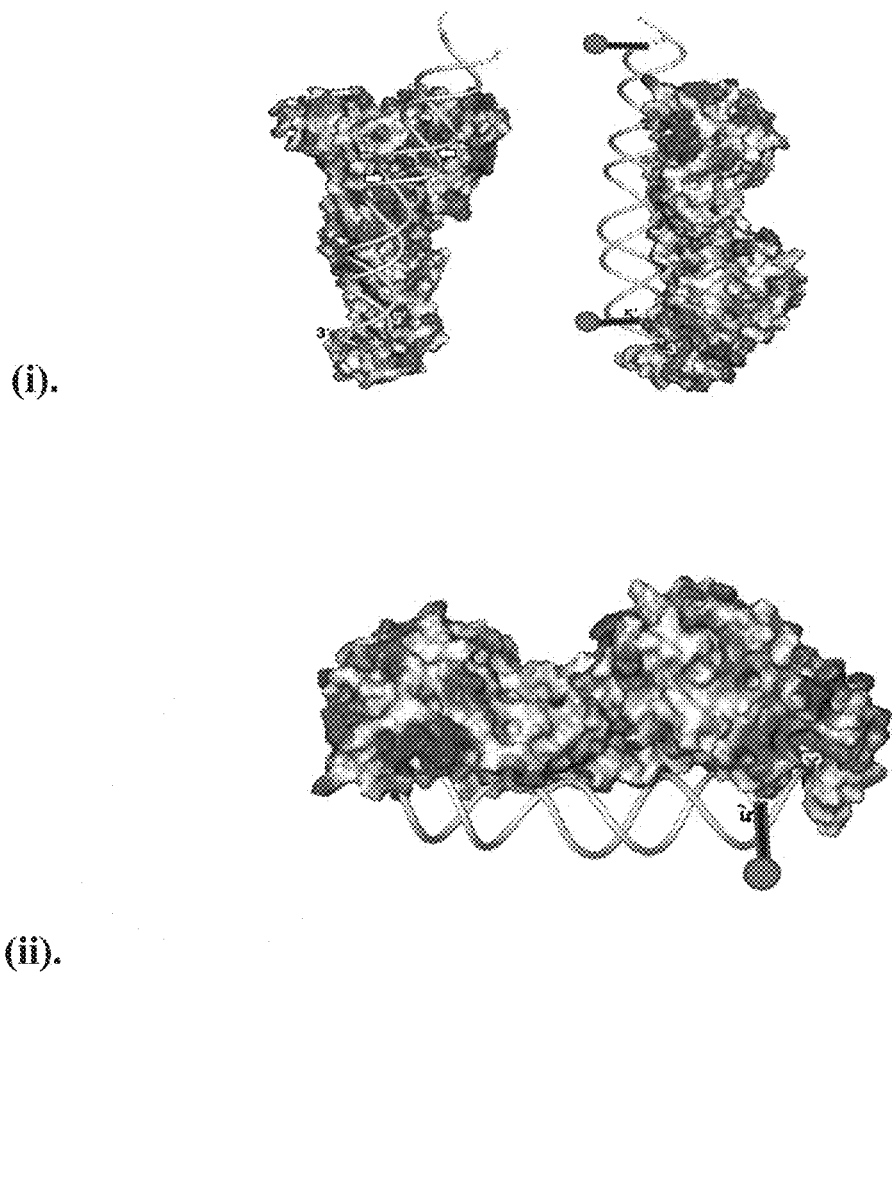
FIG. 3 schematically illustrates a mechanism for entrapment of siRNA within the cytoplasm, utilizing the Dicer enzyme to cleave and remove the MNM; (i). Docking of siRNA, linked to two Apo-Si MNMs on the Dicer protein; (ii). Removal of one motor by enzyme-mediated RNA cleavage.

The Conjugates of the invention may also comprise a cleavable group (e.g., a disulfide group, or an oligonucleotide sequence cleavable by the Dicer enzyme) (FIG. 1b, or FIG. 3). Cleavage of a Conjugate of the invention at these sites may act to trap the cargo drug (e.g., highly negatively-charged siRNA or ASO, or other medicament) in the cytoplasm of the target cell. In addition, the continuous consumption of the Conjugate due to its cleavage may also assist in maintaining a concentration gradient of the Conjugate across the cell membrane. The term "cleavable group" in the context of the present invention, therefore relates to a chemical moiety, capable of undergoing spontaneous or enzyme-mediated cleavage in certain physiological conditions, such as changes in pH, changes in red-ox state, or other conditions within cells. Examples for cleavable groups are ester, thio-ester, amide, carbamate, disulfide, ether, a pH-sensitive moiety, a redox-sensitive moiety, or a metal chelator [which thereby includes its chelated metal ion(s)]. Conceptually, a cleavable group may assist in entrapment of a drug within a target cell following its trans-membrane passage, or assist in maintaining a concentration gradient of the Conjugate of the invention) across the biological membranes.

For example, in the case of a Conjugate according to an embodiment of the invention, that comprises siRNA, ASO or a therapeutic protein as pharmaceutically-active drugs, and a disulfide group as a cleavable group, once inside the cytoplasm, the prevailing ambient reductive environment will act to reduce the disulfide bond to free thiol groups, thus cleaving the Conjugate, and leading to disengagement of the MNMs from the cargo drug. Devoid of the MNM, the charged cargo macromolecule will eventually be captured in the cytoplasm, where for example, in the case of siRNA, it will be ready for interaction with the Diver enzyme, or the RNA-induced silencing complex (RISC), resulting in silencing of the expression of a specific gene. According to embodiments of the invention, the gene may encode for a protein playing a role in the etiology or pathogenesis of a specific disease.

The term "initiator group", in the context of the present invention, relates to a chemical group, that when it undergoes a spontaneous or an enzyme-mediated chemical reaction, it initiates cleavage of an adjacent chemical bond. In more specific embodiments of the invention, the initiator group is selected from $C_4$, $C_5$, $C_6$-1,2-dithiocycloalkyl(1,2-dithiocyclo-butane; 1,2-dithiocyclopentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring).

The term "activated ester" in the context of the present invention, relates to a derivative of carboxylic acids, harboring a good leaving group, and thus being capable of interacting with amines to form amides. An example for such activating agent for carboxylic acid is N-hydroxysuccinimide (NHS).

The term "metal chelator" in the context of the present invention, relates to a chemical moiety that entraps a metal ion through coordination, wherein the coordinating atoms are selected from nitrogen, sulfur or oxygen atoms. In a preferred embodiment, the chelated ion(s) is calcium ($Ca^{+2}$), coordinated by nitrogen and oxygen atoms. In another preferred embodiment, the metal chelator is BAPTA [1,2-bis(o-aminophenoxy)ethane-N,N,N',N'-tetraacetic acid], EGTA (ethylene glycol tetraacetic acid) or analogues thereof, manifesting advantageous selectivity for $Ca^{+2}$ over other ions such as $Mg^{+2}$. Such chelators may enable utilization of the substantial concentration gradient of $Ca^{+2}$ between the extracellular space and the cystosol, for potential disengagement of the MNM from the cargo drug and capture and accumulation of the target drug within the cytoplasm.

The term "heteroalkyl, heteroalkylene or heteroaryl" in the context of the invention, relates to the respective hydrocarbon structure, where a least one of the atoms has been replaced by a nitrogen, oxygen, or sulfur atom(s), or any combination thereof.

According to one of the embodiments of the invention, the "cargo" or the "cargo drug" is a siRNA, ASO, a therapeutic protein, or any other medicament to be delivered across cell membranes and into cells. Said cells may be either in cell culture of within the body of a living animal or a human subject, and said delivery aims at exerting beneficial therapeutic effects.

The term "precursor" in the context of the invention, relates to a chemical moiety, used in the synthesis of conjugates according to embodiments of the invention. The precursor comprises chemical groups, destined to be removed during the synthesis of the Conjugate in various stages of the synthesis, for example without limitation, during the attachment of a macromolecule, such as an oligonucleotide to MNMs of the invention.

The field of Protein Drugs for Intracellular Targets (PDIT) is a relatively novel field, derived, in part, from the completion of the Human Genome Sequencing Project, which allows identification of a huge number of novel intracellular targets for potential medical interventions, through administration of protein drugs, gene silencing, RNA or DNA editing, or protein replacement therapy. Conceptually, such therapeutic strategies can be useful for treatment of almost any medical disorder. Specific, highly attractive candidate proteins within the PDIT field are the CRISPR (clustered regularly interspaced short palindromic repeats)-related proteins, and specifically, the Cas9 Protein. This recently-discovered protein is initially a bacterial protein, naturally-used by bacteria as for an anti-viral agent. Practically, Cas9 can be loaded by any RNA sequence, entailing specificity in directing the protein specifically to any locus within the genome, rationally-selected according to its potential relation to a mutated, defective gene. Cas9 then induces an accurate double-strand cut of the DNA. Naturally-occurring DNA repair mechanisms may then be subsequently recruited, to repair said DNA locus within the malfunctioning gene. Therefore, Cas9 and related proteins enable highly effective gene editing (adding, disrupting or changing the sequence of specific genes) and gene regulation and repair, applicable to species throughout the tree of life. By delivering Cas9 protein and an appropriate guide RNA into a cell, the organism's genome can therefore be cut at any desired location, and be subjected to editing and repair.

As exemplified below (Example 4), an embodiment of the invention includes one or more "molecular nanomotors (MNMs)" linked to the Cas9 protein, having a potential role in DNA or RNA editing.

Another embodiment of the invention, relates to a therapeutic protein, administered as a replacement therapy. Such replacement therapy may be needed in the treatment of a disease, associated with reduced levels of a physiologically-important protein, due to its deficiency or mutations. In such case, the respective protein may be delivered exogenously, as a drug. Since protein is a charged macro-molecule, many times it is incapable of trans-membrane delivery, unless conjugated to a delivery system such as the MNMs of the invention.

MNMs according to embodiments of the invention are typically hydrophobic [typically, without limitation, having octanol to water partition co-efficient (log P)>1], dipolar, uncharged chemical moieties, designed according to the principle of asymmetrical polarity (explained above). As discussed, this unique set of features of the MNM (namely, being hydrophobic, of overall neutral charge, but being polar, with focused partial negative charges and dispersed partial positive charges, creates a unique vectorial system when put in the internal membrane electric field, entailing movement of the molecule within the phospholipid milieu, from the membrane/water interface to the membrane center. When attached to a drug, this molecule respectively pulls the drug to the membrane core.

As schematically illustrated in FIG. 1B, Conjugates according to embodiments of the invention typically include "Molecular NanoMotor(s) (MNMs)" as described above, being an E, E' or E" moiety [demonstrated, for example, by the moiety according to Formula (X)]. The "Molecular NanoMotor (MNM)" is a combination of the following structural elements:

(i). A negative pole (group A of moiety E, E' or E"), typically comprising at least one electronegative atom(s), selected from a halogen [for example, fluorine atom(s)] or oxygen, arranged in space as a focused, spherical (or near spherical) arrangement. Due to the electron-withdrawing properties of such atoms, and their structural arrangement in space, the negative pole of the Conjugate is an electron-rich focus.

(ii). A positive pole (group B of moiety E, E' or E"), comprising relatively electropositive atoms, selected from carbon, silicon, boron, phosphor and sulfur, arranged to enable maximal interaction with adjacent hydrocarbon chains, when put in a phospholipid membrane, preferably through arrangement as an aliphatic or aromatic structure of linear, branched or cyclic chains, or combinations thereof. In an embodiment of the invention, the positive pole comprises linear, saturated hydrocarbon chain(s), or a steroid moiety, such as cholesterol, bile acids, estradiol, estriol, or derivatives or combinations thereof. Optionally, the Conjugate of the invention may comprise several negative pole and several positive pole structural motifs, for example, sequentially-arranged perfluro- and oxygen-motifs, separated by hydrocarbon chains, exemplified in the Compound according to Formula VIIIa.

In addition to the "Molecular NanoMotor(s) (MNMs)", a Conjugate according to embodiments of the invention may also comprise one or more linkers (L) and cleavable groups (Q), as further described above. The linkage of a drug D to the molecular nanomotor(s) E, E' or E" can be either directly, or through moiety L or Q; said linkage can be through covalent or non-covalent bonds, such as electrostatic or coordinative bonds.

Embodiments of the invention further relate to the use of Conjugates according to the invention, comprising therapeutically-useful drugs, such as proteins or oligonucleotides (e.g., siRNA or ASO), for the treatment of medical disorders in a subject in need thereof. The medical disorders may be, without being limited, degenerative disorders, cancer, traumatic, toxic or ischemic insults, infections or immune-mediated disorders, in which specific protein(s) play(s) a role in either disease etiology or pathogenesis, and where modulation of the expression of the respective gene(s), through siRNA or antisense mechanisms, or modulation of the activity of the respective protein by a therapeutic protein or by protein replacement therapy, may have beneficial effects in inhibiting disease-related processes or treating the underlying disease.

For example, Conjugates according to embodiments of the invention, may be used as antisense therapy, which is a form of medical treatment comprising the administration of a single-stranded or a double-stranded nucleic acid strands (DNA, RNA or a chemical analogue), that binds to a DNA sequence encoding for a specific protein, or to the respective messenger RNA (mRNA) where the translation into protein takes place. This treatment may act to inhibit the expression of the respective gene, thereby preventing the production of the respective protein. Alternatively, the Conjugates of the invention may comprise therapeutic proteins, such as the Cas9 protein.

The terms "drug" or "medicament" in the context of the present invention relate to a chemical substance, that when administered to a patient suffering from a disease, is capable of exerting beneficial effects on the patient. The beneficial effects can be amelioration of symptoms, or counteracting the effect of an agent or a substance, that play(s) a role in the disease process. The drug may comprise a small molecule or a macromolecule, such as, a protein, or single- or double-stranded RNA or DNA, administered to inhibit gene expression. Among others, the drug may comprise siRNA or ASO. In some embodiments, the drug is aimed at treating degenerative disorders, cancer, ischemic, infectious, toxic insults, or immune-mediated disorders.

The term "biological membrane" according to the invention, refers to any phospholipid membrane related to a biological system. Examples for such phospholipid membranes are the plasma membrane of cells, intercellular membranes, or biological barriers, such as, the blood-brain-barrier (BBB), the ocular-blood-barrier (BOB), or the placenta barrier.

Embodiments of the invention provide Conjugates, comprising MNMs according to embodiments of the invention, and a drug. Embodiments of the invention further provide pharmaceutical compositions, comprising the Conjugates described herein, and pharmaceutically-acceptable carrier(s) or salt(s).

Other embodiments of the invention, describe methods for treatment of medical disorders, comprising administration to a patient in need, pharmaceutical composition of the Conjugates of the invention.

In some embodiments, the medical disorder is cancer. In some specific embodiments, the cancer is, among others melanoma or uterine cervical cancer.

According to some embodiments, the Conjugates and pharmaceutical compositions of the invention may be used to achieve efficient delivery and effective performance of a replacement protein therapy or gene therapy [for example, without limitation siRNA or antisense therapy (ASO)] in vivo, in the clinical setting.

A Conjugate according to embodiments of the invention may be advantageous in improving delivery of siRNA, ASO or a therapeutic protein through cell membranes or through biological barriers, such as the Blood-Brain-Barrier (BBB), thus improving the performance of said macromolecule drug in one or more aspects, such as, for example, efficacy, toxicity, or pharmacokinetics.

As described above in a non-limiting potential Mechanism Of Action (MOA), Conjugates according to embodiments of the invention, comprising a drug such as siRNA or a therapeutic protein, conjugated to MNM(s), undergo trans-membrane delivery when interacting with a phospholipid membrane. This mechanism of action is schematically summarized in FIG. 2. Due to the principle of asymmetrical polarity, described in FIGS. 1a and 2, initially, the MNMs move from the membrane surface to the membrane core, energized by the internal membrane electric field (i). As the second stage [FIG. 2 (ii)], the macromolecule, linked to the MNMs, is forced to approach the membrane surface, thus perturbing the hydration shells of both the cargo macromolecule drug and the phospholipid head-groups. Consequently, there is lateral movement of the phospholipid head-groups, and formation of transient membrane pores, through which the macromolecule drug is delivered into the cell. Subsequent closure of the transient pore then takes place with membrane healing [FIG. 2 (iii)].

In an example, schematically presented in FIG. 1B, the Conjugate of the invention comprises a cargo drug (moiety D), being siRNA, ASO or a therapeutic protein, and a disulfide group, for entrapment of the cargo drug in the cytoplasm, due to the ambient reductive environment.

In another embodiment of the invention, entrapment of siRNA in the cytoplasm may be achieved through the administration of a Conjugate, where D is a double-stranded RNA, which is a Dicer substrate, namely, comprising 23-30 nucleotides, selected according to the genetic code suitable for silencing a specific target gene. One or several MNMs may then be linked to such oligonucleotide drug. Preferably, MNMs are attached at the 3'-end and/or the 5'-end of the sense ("passenger") strand, and/or at the 5'-end of the antisense ("guide") strand. Upon administration of the Conjugate, the MNMs will enable the trans-membrane delivery of the macro-molecule drug. Subsequent cleavage of the dsRNA by the Dicer enzyme in the cytoplasm will then remove the MNM(s) at the 3'-end of the passenger strand, and/or at the 5'-end of the guide stand, thus releasing the siRNA. The siRNA, due to its numerous negative charges, is eventually entrapped in the cytoplasm, where it interacts with the RISC complex, resulting in silencing of the target gene. This, Dicer-mediated mechanism of intracellular entrapment is schematically illustrated in FIG. 3.

In yet another mechanism, entrapment of siRNA or ASO within the cytoplasm can be achieved in the case that E, E' or E" comprises a Q moiety, being a chelator for calcium ion(s), bound via coordinative bonds to phosphate groups of the oligonucleotide drug. Such binding can be mediated, for example, by $Ca^{+2}$ ions. Such Conjugatse may be stable in the plasma, due to the relatively high ambient $Ca^{+2}$ levels (about 1 mM). Moreover, due to the MNMs, the Conjugates will manifest trans-membrane delivery into the cells. Once inside the cytoplasm, the low cytoplasmatic $Ca^{+2}$ levels will induce de-complexation, releasing the cargo oligonucleotide, which will then interact with its target sites, such as the Dicer or the RISC complex, for gene silencing.

Conjugates according to embodiments of the invention have the structure, as set forth in general Formula (I):

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes. D may be a small-molecule drug, a peptide, a protein, or a native or modified, single-stranded or double-stranded DNA or RNA, such as siRNA or ASO;

y, z and w are each an integer, independently selected from 0, 1, 2, 3, 4, 5, 6; at least one of y, z or w is different from 0. In one embodiment, y=1, z=o and w=0; in another embodiment y=1, z=1 and w=0.

E, E', or E" can be the same or different, each having the structure as set forth in general Formula (II):

$(A)_a$-B-$L_1$-$Q_1$-$L_2$-$Q_2$-$L_3$     Formula (II)

wherein

B (a positive pole as described above) is selected from the group consisting of, linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene;

$C_5$, $C_6$, $C_7$, $C_8$, $C_9$, $C_{10}$, $C_{11}$, $C_{12}$, $C_{13}$, $C_{14}$ aryl or heteroaryl;

one or more steroid moiety (such as, cholesterol, bile acid, estrogen, estradiol, estriol), nucleoside, nucleotide; and any combination thereof;

wherein each group is optionally substituted by hydroxyl, amine, or thiol;

$Q_1$ and $Q_2$ are each independently an optionally cleavable group, selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], imidazole, triazole, a pH-sensitive moiety, a redox-sensitive moiety; a metal chelator, including its chelated metal ion; and any combinations thereof;

$L_1$, $L_2$ and $L_3$ are each independently selected from null and the group consisting of:

linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene;

$C_5$, $C_6$, $C_7$, $C_8$, $C_9$, $C_{10}$, $C_{11}$, $C_{12}$, $C_{13}$ or $C_{14}$ aryl or heteroaryl;

—(O—$CH_2$—$CH_2$)$_u$—, wherein u is an integer of 1, 2, 3, 4, 5;

nucleoside, nucleotide; imidazole, azide, acetylene; and any combinations thereof;

wherein each group is optionally substituted by one or more hydroxyl, amine, or thiol;

wherein each of $Q_1$, $Q_2$, $L_1$, $L_2$ and $L_3$ optionally comprises a T moiety; wherein T is an initiator group, selected from $C_4$, $C_5$, $C_6$-1,2-dithiocycloalkyl(1,2-dithiocyclo-butane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); and T optionally comprises an amine group.

A is selected from the structures as set forth in Formulae (III), (IV), (V) and (VI) (a negative pole as described above):

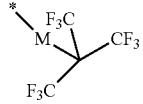

Formula (III)

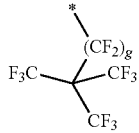

Formula (IV)

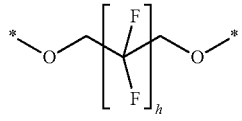

Formula (V)

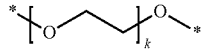

Formula (VI)

M is selected from —O— or —$CH_2$—; and g, h and k are each individually an integer selected from the group consisting of 0, 1, 2, 3, 4, 5, 6, 7, 8, 9, 10, 11, 12, 13, 14, 15 and 16; * is —H, or a point of linkage to B; a is an integer, selected from 1, 2, 3 or 4.

The linkage of D to other moieties of the molecule can be through covalent, electrostatic, or coordinative bonds. In the case that the bond is covalent, linkage can be through a $Q_1$ or $Q_2$ group, selected from the group consisting of ether, ester, amide, thioester, thioether and carbamate groups. In the case that the bond is coordinative, it involves a $Q_1$ or $Q_2$ group that is a metal chelator, and the linkage preferably involves coordination of calcium ion(s). An example for electrostatic linkage, can be a salt bridge between amine groups of moiety $L_1$, $L_2$ or $L_3$ of E, E' or E", and negatively-charged phosphate groups of D. In case that D is an oligonucleotide, linkage can be to the nucleobase, to the ribose moiety (e.g., through the 2', 3' or 5' positions of the ribose), or to the phosphate moiety of the nucleotide; linkage can be either to a terminal, or to a non-terminal nucleotide of the oligonucleotide chain; linkage can be through a natural or through a modified nucleotide. In the case that D is a protein, its linkage to the other moieties of the molecule can be through linkage to side chain(s) of the protein's amino acids, such as lysine, cysteine, glutamate or aspartate.

The term "oligonucleotide", in the context of the invention, may include DNA or RNA molecules, each being a single-stranded or double-stranded sequence of one or more nucleotides. Each nucleotide comprises a nitrogenous base (nucleobase), a five-carbon sugar (ribose or deoxyribose), and a phosphate group. The nucleobases are selected from purines (adenine, guanine) and pyrimidines (thymine, cytosine, uracil). In addition, the term may also refer to modified forms of nucleotides, where the modification may be at the backbone of the molecule (e.g., phosphorothioate, peptide nucleic acid) or at the nucleobase (e.g., methylation at the 2' position of the ribose group in RNA, or attachment of fluorine atoms at that site). These modifications may enable properties such as improved stability or improved pharmacokinetics of the oligonucleotide in body fluids. The use of such modified oligonucleotides is therefore also within the scope of the invention.

In one embodiment, a method for specific inhibition of gene expression is disclosed, applicable either in vitro or in vivo. The method comprises the utilization of a Conjugate of the invention or a pharmaceutical composition comprising the Conjugate, where D is siRNA or ASO, designed to silence the expression of a specific gene, which encodes for a pathogenic protein, that has a role in the etiology or pathogenesis of disease.

Accordingly, Conjugates according to embodiments of the invention may be used for the treatment of a medical disorder. Embodiments of the invention therefore disclose a method for medical treatment, comprising the administration to a patient in need, therapeutically effective amounts of a pharmaceutical composition according to embodiments of the invention. In one embodiment, the administered pharmaceutical composition may comprise siRNA or an antisense oligonucleotide, active in inhibiting the expression of a specific gene encoding for a disease-related protein.

In one embodiment of the invention, there is provided a Conjugate according to general Formula (I), comprising MNMs, being an E, E' or E" moiety, having the structure as set forth in Formula (VII):

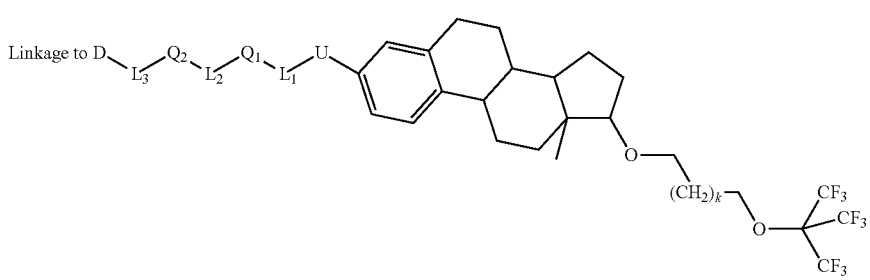

Formula (VII)

where m is an integer, selected from the group consisting of null and 1, 2, 3, 4, 5, 6, 7, 8, 9 or 10; k is an integer, selected from 0, 1, 2, 3 or 4; U is selected from the group consisting of null, —O—, N and NH; and the E, E' or E" moiety is linked to D; including pharmaceutically acceptable salts, hydrates, solvates and metal chelates of the Compound represented by the structure as set forth in Formula (VII), and solvates and hydrates of the salts.

In one embodiment, k=1.

In another embodiment, the steroid moiety is substituted by residue of lithocholic acid, or a related analogue.

In another embodiment, $L_1$, $L_2$ and $L_3$ are each individually selected form null and a linear, cyclic or branched $C_1$, $C_2$, $C_3$, $C_4$, $C_5$, $C_6$, $C_7$, $C_8$ hydrocarbon chain; $L_1$, $L_2$ and $L_3$ can be the same or different.

In another embodiment $Q_1$ or $Q_2$ is an amide group, an ester, a carbamate, or a disulfide.

In still another embodiment, $Q_1$ or $Q_2$ is imidazole.

In still another embodiment, $L_1$, $L_2$ or $L_3$ comprises a T moiety, being 1,2-dithiocyclo-butane, optionally linked to an amide or amine group.

In a more specific embodiment, there is provided a Conjugate according to general Formula (I), which includes E, E' or E", having the structure as set forth in Formulae (VIIa):

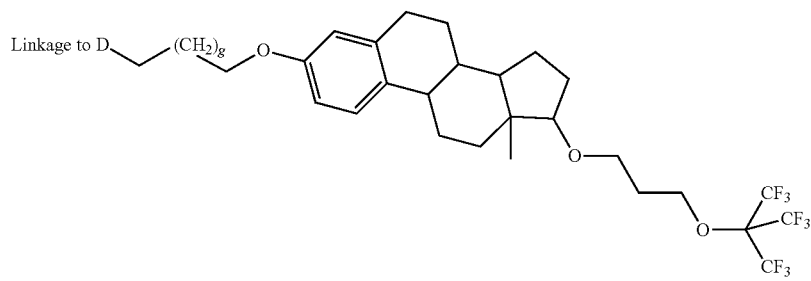

Formula (VIIa)

including pharmaceutically acceptable salts, hydrates, solvates and metal chelates of the Compound represented by the structure as set forth in Formula (VIIa), and solvates and hydrates of the salts; wherein g stands for an integer of 0, 1, 2, 3, 4, 5, 6, 7, 8, 9, 10, 11, 12, 13, 14.

In a preferred embodiment, g=2 or g=12.

In another embodiment, there is provided a molecule according to general Formula (I), which includes E, E' or E", having the structure as set forth in Formulae (VIII):

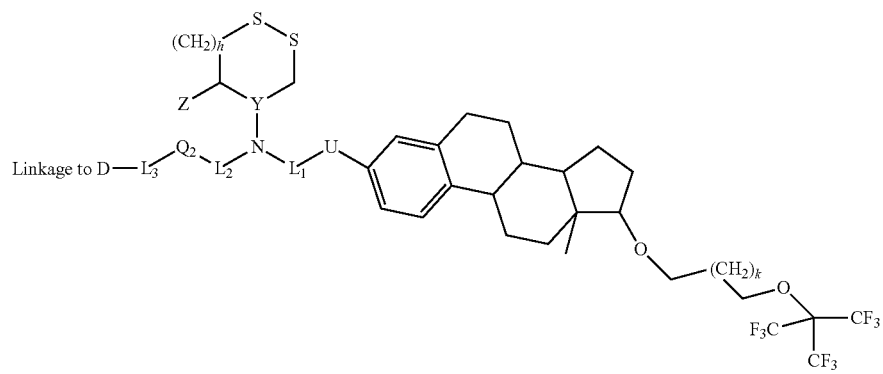

Formula (VIII)

including pharmaceutically acceptable salts, hydrates, solvates and metal chelates of the compound represented by the structure as set forth in Formulae (VIII) and solvates and hydrates of the salts; where k stands for an integer, selected from the group consisting of 0, 1, 2, 3, 4, 5, 6, 7, 8, 9, 10, 11, 12, 13, 14, 15, 16; h stands for an integer, selected from the group consisting of 0, 1, 2, 3, 4; U is selected from the group consisting of null, and a $C_1$, $C_2$, $C_3$ or $C_4$ alkyl; Z is selected from hydrogen, hydroxyl and amine groups; Y is selected from —CH— and a nitrogen atom.

In preferred embodiments, k=1, and h=1.

In another embodiment, there is provided a molecule according to general Formula (I), which includes E, E' or E", having the structure as set forth in Formulae (IX):

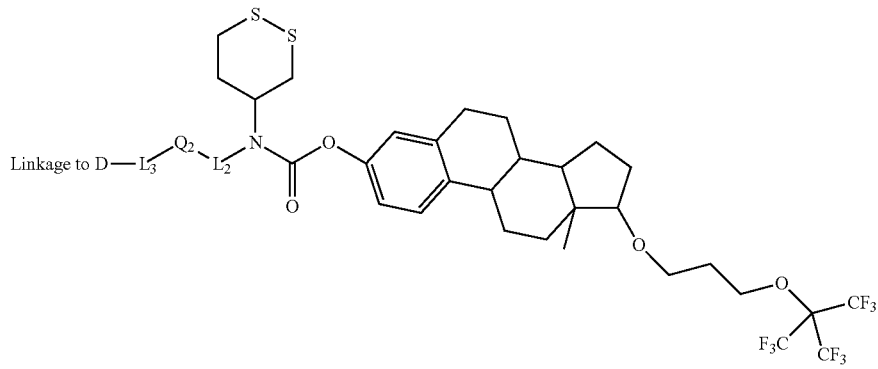

Formula (IX)

including pharmaceutically acceptable salts, hydrates, solvates and metal chelates of the compound represented by the structure as set forth in Formulae (IX) and solvates and hydrates of the salts.

In another embodiment, there is provided a molecule according to general Formula (I), which includes E, E' or E", having the structure as set forth in Formula (X):

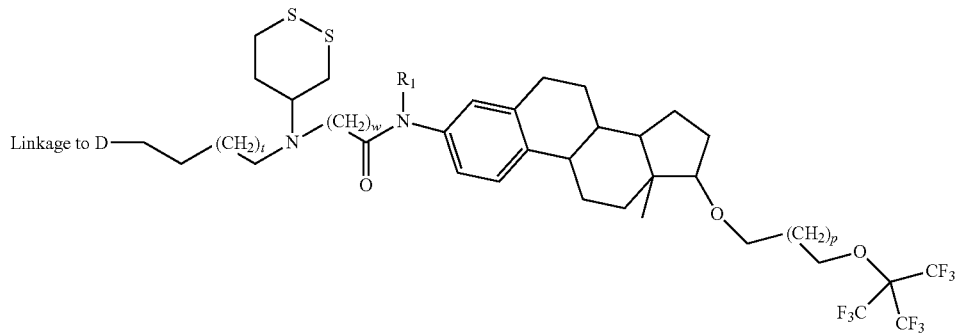

Formula (X)

including pharmaceutically acceptable salts, hydrates, solvates and metal chelates of the compound represented by the structure as set forth in Formulae (X) and solvates and hydrates of the salts; wherein w stands for an integer of 0, 1, 2 or 3; t stands for an integer of 0, 1, 2, 3, 4, 5, 6, 7, 8, 9, 10, 11, 12, 13 or 14; p stands for an integer of 0, 1, 2 or 3; $R_1$ stands for hydrogen, or an alkyl group of 1, 2 or 3 carbon atoms.

In another embodiment, there is provided a molecule according to general Formula (I) and Formula (XI), which includes E, E' or E", having the structure as set forth in Formulae (XI):

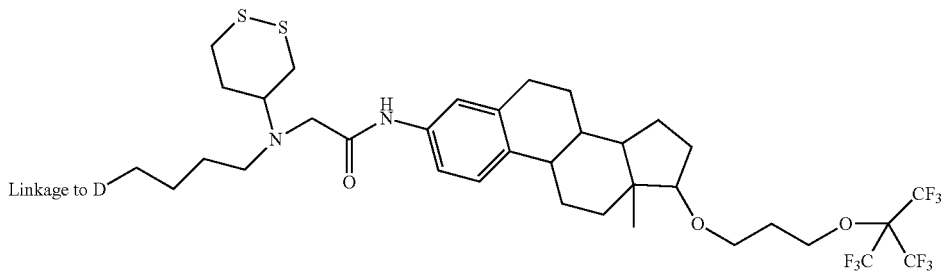

Formula (XI)

including pharmaceutically acceptable salts, hydrates, solvates and metal chelates of the compound represented by the structure as set forth in Formulae (XI) and solvates and hydrates of the salts.

In another embodiment, there is provided a molecule according to general Formula (I) and Formula (VIII), which includes E, E' or E", having the structure as set forth in Formulae (XII):

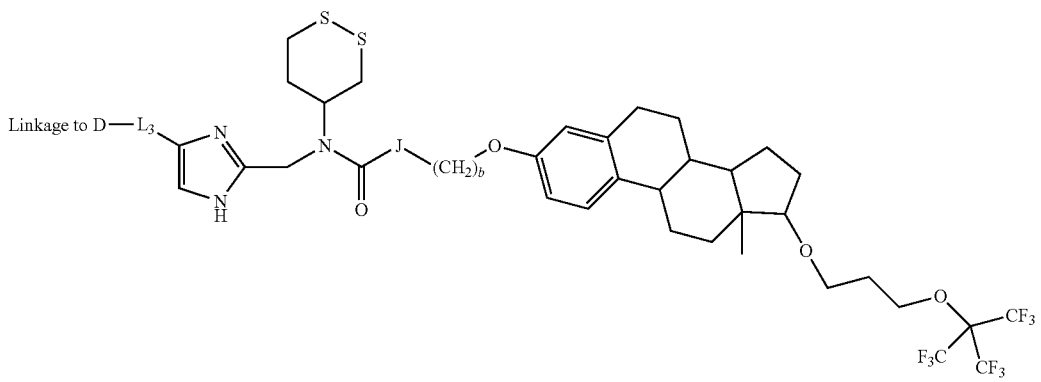

Formula (XII)

including pharmaceutically acceptable salts, hydrates, solvates and metal chelates of the compound represented by the structure as set forth in Formulae (XII) and solvates and hydrates of the salts; wherein b strands for an integer of 0, 1, 2, 3, 4, 5, 6, 7, 8 or 9; J is null, nitrogen or an oxygen atom.

In a specific embodiment, there is provided a molecule according to general Formula (I) and Formula (XII), which includes E, E' or E", having the structure as set forth in Formulae (XIII):

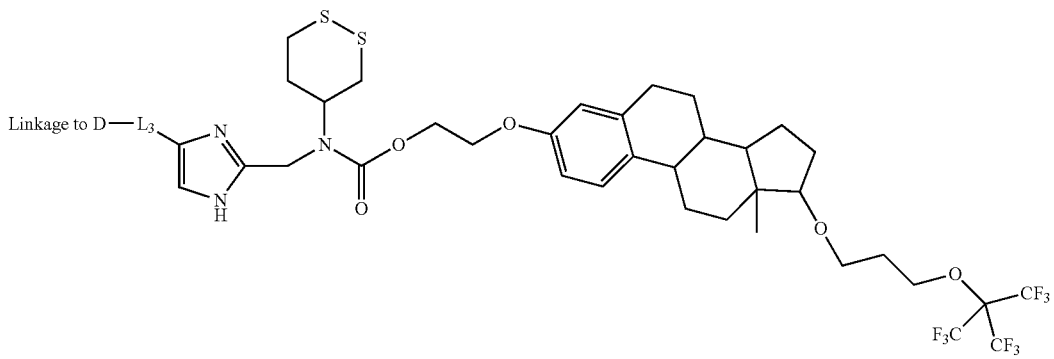

Formula (XIII)

In another specific embodiment, there is provided a Conjugate according to general Formula (I) and Formula (XII), which includes E, E' or E", having the structure as set forth in Formulae (XIV):

Formula (XIV)

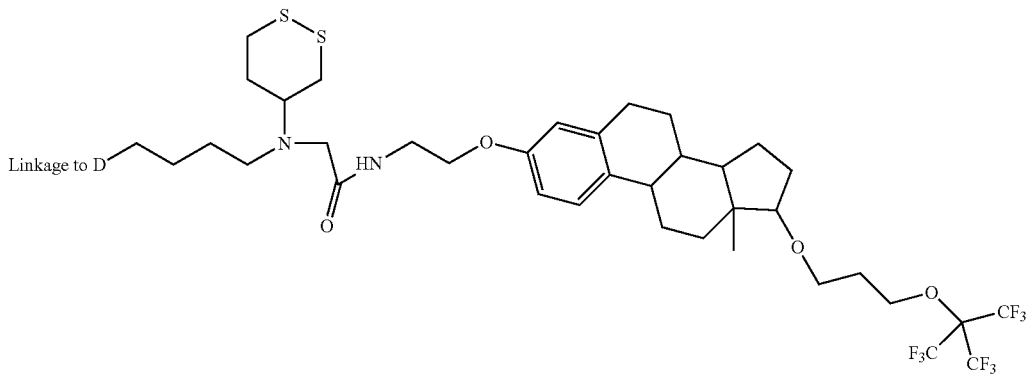

In another embodiment, the invention concerns a Conjugate, having the structure as set forth in general Formula (I), which comprises E, E' or E", having the structure as set forth in Formula (XVI):

Formula (XV)

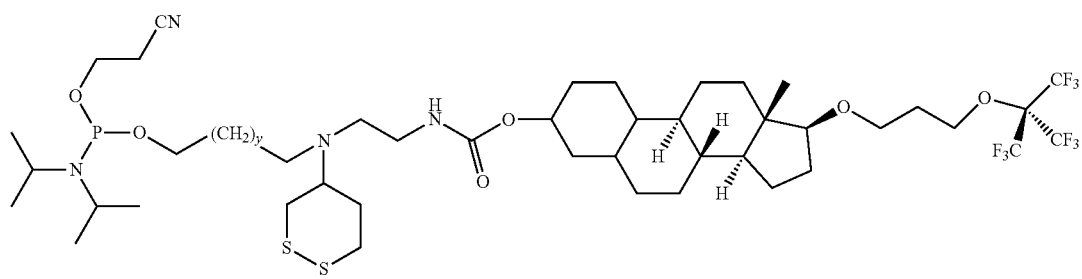

including pharmaceutically acceptable salts, hydrates, solvates and metal chelates of the compound represented by the structure as set forth in Formulae (XV) and solvates and hydrates of the salts; where y stands for an integer, selected from the group consisting of 0, 1, 2, 3, 4, 5, 6, 7, 8, 9, 10, 11 or 12. In a preferred embodiment, y=3.

In another embodiment, the invention concerns a Conjugate, having the structure as set forth in general Formula (I), which comprises E, E' or E", having the structure as set forth in Formula (XVI):

Formula (XVI)

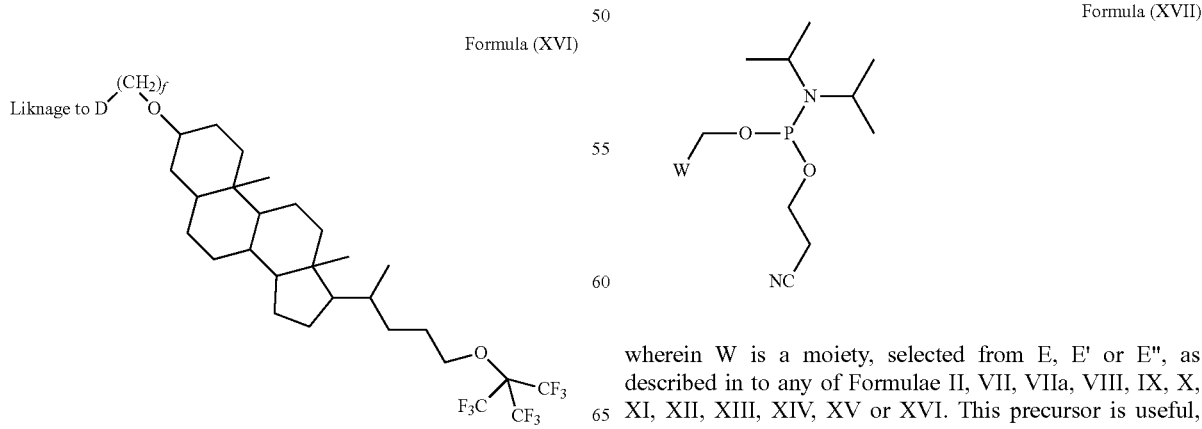

including pharmaceutically acceptable salts, hydrates, solvates and metal chelates of the compound represented by the structure as set forth in Formulae (XVI) and solvates and hydrates of the salts; where f stands for an integer, selected from the group consisting of 0, 1, 2, 3, 4, 5, 6, 7, 8, 9, 10, 11, 12, 13, 14, 15 and 16.

Also within the scope of the invention are molecules termed "precursors". A "precursor" in the context of the invention, is a chemical moiety, used in the synthesis of Conjugates according to embodiments of the invention. Often, the precursor comprises chemical groups, destined to be removed during the synthesis of the Conjugate, in stages such as attachment of a therapeutic molecule or a macromolecule to the MNMs of the invention.

In one embodiment, the precursor has the structure, as set forth in Formula (XVII):

Formula (XVII)

wherein W is a moiety, selected from E, E' or E", as described in to any of Formulae II, VII, VIIa, VIII, IX, X, XI, XII, XIII, XIV, XV or XVI. This precursor is useful, without limitation, for attachment to the 5'-end of an oligonucleotide.

Another precursor of the invention has the structure according to Formula (XVIII):

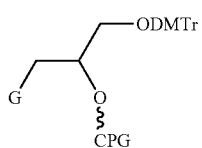

Formula (XVIII)

wherein G is a moiety, selected from E, E' or E" as described in any of Formulae II, VII, VIIa, VIII, IX, X, XI, XII, XIII, XIV, XV or XVI. This precursor may be useful, among others, for attachment to the 3'-end of an oligonucleotide; DMT=Dimethoxytrityl; CPG=Controlled Pore Glass (CPG).

In other embodiments of the Invention, the precursor has the structure as set forth in any of Formulae II, VII, VIIa, VIII, IX, X, XI, XII, XIII, XIV, XV or XVI, wherein at the point of linkage to D, there is linkage to a group selected from phosphoroamidite, an activated ester, azide or acetylene. The latter two groups may be useful for attachment to D by "click chemistry", for example without limitation, through the Azide-alkyne Huisgen cyclo-addition reaction.

Embodiments of the invention may further include pharmaceutical compositions, comprising a Conjugate, comprising a molecule according to any of Formulae II, VII, VIIa, VIII, IX, X, XI, XII, XIII, XIV, XV or XVI, and a pharmaceutically-acceptable salt or carrier.

The invention also comprises methods for specific inhibition of gene expression, in vitro or in vivo. In one embodiment, the method may include utilization of a Conjugate according to any of Formulae II, VII, VIIa, VIII, IX, X, XI, XII, XIII, XIV, XV or XVI; or a respective pharmaceutical composition, where D is siRNA or an ASO, designed to silence the expression of a specific gene. In some embodiments, the gene encodes for a pathogenic protein, having a role in the etiology or pathogenesis of a disease. In some embodiments, D is a therapeutic protein.

Conjugates according to embodiments of the invention may be used for the treatment of a medical disorder. Embodiments of the invention include methods for medical treatment, comprising the administration to a patient in need therapeutically effective amounts of a pharmaceutical composition, comprising a Conjugate according to any of Formulae II, VII, VIIa, VIII, IX, X, XI, XII, XIII, XIV, XV or XVI; where D is a drug useful for treatment of the respective medical disorder.

In one embodiment, the method is for genetic treatment with siRNA or ASO, said method comprising the administration to a patient in need therapeutically effective amounts of a pharmaceutical composition, comprising a Conjugate of the invention according to any of Formulae II, VII, VIIa, VIII, IX, X, XI, XII, XIII, XIV, XV or XVI; where D is siRNA, an ASO or a therapeutic protein, useful in inhibiting the expression of a gene which plays a role in the disease of the specific patient.

In another embodiment of the invention, the invention includes a method for medical treatment of a disease by therapeutic a protein, where D is a protein to be delivered across biological phospholipid membranes into cells, or through biological barriers, such as the blood-brain barrier. Said cells are either in cell culture in vitro, or in a living animal or a human subject in vivo.

In some embodiments, the cell is a neoplastic cell. In some embodiments, the neoplastic cell is a tumor cell. In some embodiments, the neoplastic cell is a cell within a metastasis. The cell may be a eukaryotic cell, a eukaryotic cell infected with an oncogenic agent, a human cell, a cell that is a pre-cancerous cell, or any combination thereof. The cell may be a cell within a cell culture, or within a living animal or a human subject.

In yet another embodiment of the invention, D is a protein, administered as a replacement therapy, e.g., to replace a mutated, malfunctioning protein, thus addressing a physiological need. In another embodiment, D is a protein that has as role in gene regulation, including, among others, proteins that have a role in DNA or RNA editing (adding, disrupting or changing the sequence of specific genes).

In one embodiment, said protein may be a member of the CRISPRs (clustered regularly interspaced short palindromic repeats) related proteins. Specifically, said protein can be, or may comprise the Cas9 protein (CRISPR associated protein 9), an RNA-guided DNA nuclease enzyme, or an analogue thereof.

In one of the embodiments of the invention, it describes a method for genetic treatment of a medical disorder, said method comprising administration to a patient in need, therapeutically effective amounts of a pharmaceutical composition, comprising a conjugate according to Formula (I), where D is a CRISPR protein, such as Cas9, administered together with an appropriate guide oligonucleotide, thus achieving delivery of the protein, loaded with a respective guide oligonucleotide, into the cells, where the CRISPR protein can exert its genome editing activity. A guide oligonucleotide, in this context, is a sequence of RNA or DNA that guides the Cas9 protein to a specific locus (place) on the DNA, in order to induce a double-strand DNA cleavage at that site, thus enabling to repair a local defect in the genetic material. In the case of Cas9, the guide oligonucleotide is short segment of RNA, the sequence of which is complementary to the sequence of the target DNA locus.

Therefore, conjugates according to embodiments of the invention, and the respective pharmaceutical compositions and methods may be beneficial, among others, in the treatment of medical disorders, selected, among others, from cancer, toxic insults, ischemic disease, infectious disease, protein storage disease, trauma, immune-mediated disease, or a degenerative disease.

According to some embodiments, the medical disorder is cancer. As used herein, the term "cancer" refers to the presence of cells possessing characteristics, typical of cancer-causing cells, such as uncontrolled proliferation, loss of specialized functions, immortality, significant metastatic potential, significant increase in anti-apoptotic activity, rapid growth and proliferation rate, and certain characteristic morphology and cellular markers. Typically, cancer cells are in the form of a tumor, existing locally within an animal, or circulating in the bloodstream as independent cells, as are, for example, leukemic cells.

In the field of neurological disorders, conjugates according to embodiments of the invention may be useful, among others, in the treatment of neurodegenerative disorders, such as Alzheimer's disease, Motor Neuron Disease, Parkinson's disease, Huntington's disease, multiple sclerosis and Creutzfeldt-Jacob disease.

EXAMPLES

Some examples will now be described, in order to further illustrate the invention, and in order to demonstrate how embodiments of the invention may be carried-out in practice.

In the following Examples, described are Conjugates, comprising the MNMs of the invention, attached to a single-stranded or to a double-stranded oligonucleotide. These Examples demonstrate the entire spectrum of the invention, namely, that the MNM of the Invention is: (i). Successfully synthesized; (ii). Successfully conjugated to a macromolecule drug (e.g., single-stranded or double-stranded DNA or RNA); (iii). Enable efficient delivery of heavily-charged macro-molecules (e.g., carrying 29 or 58 negative charges) across hydrophobic phospholipid membranes into cells; and (iv). Enable these macro-molecules, once inside the cells, to exert a useful biological activity (e.g., gene silencing).

Example 1

A General Method for Synthesis of Conjugates According to Embodiments of the Invention, Comprising Oligonucleotides Initially, a gene to be silenced is chosen based on its role in disease etiology or pathogenesis. Then, based on bio-informatic methodologies known in the art, the nucleotide sequence (typically 19-21 base-pairs double-stranded RNA for a RISC substrate, or 25-29 base-pairs double-stranded RNA for a Dicer substrate) is determined.

Synthesis is carried out in the 3' to 5' direction. Solid phase synthesis is applied, using phosphoramidite building blocks, derived from protected 2'-deoxynucleosides (dA, dC, dG, and T), ribonucleosides (A, C, G, and U), or chemically modified nucleosides, e.g. LNA (locked nucleic acids) or BNA (bridged nucleic acids). The building blocks are sequentially coupled to the growing oligonucleotide chain, in the order determined by the sequence of the desired siRNA.

Following the construction of the oligonucleotide, an E moiety of the invention is added, as one of the building blocks of the oligonucleotide. The E moiety is added as its precursor form, as described above. For linking the compound to the 5'-end of the oligonucleotide, a precursor according to Formula (XVII), comprising a phosphoramidite moiety is utilized. For linking the compound at the 3'-end of the oligonucleotide, a precursor according to Formula (XVIII) is utilized. Among others, this precursor may comprise acetylene or azide moieties to mediate linkage of the E moiety to the oligonucleotide chain. The process is fully automated. Upon completion of the assembly of the chain, the product is released from the solid support into solution, de-protected, and collected. The desired Conjugate is then isolated by high-performance liquid chromatography (HPLC), to obtain the desired conjugated oligonucleotide in high purity. In the case of siRNA, each of a complementary RNA strands is synthesized separately, and then annealing of the two strands is performed in standard conditions known in the art, to yield the desired double-stranded siRNA.

Example 2

Chemical Synthesis of E Moieties of the Invention (E, E' or E")

Molecular design is performed by Aposense, Ltd. Petach-Tiqva, Israel, and synthesis is performed by Syncom BV, the Netherlands. The starting material perfluoro-tertbutanol is commercially-available. In this example, the E moieties are designed to be linked to the 5'-end of the oligonucleotide, and therefore a phosphoramidite moiety is added at the last step of the synthesis, towards conjugation to the oligonucleotide chain.

Example 2a

A Method for Synthesis of an E Moiety According to Formula (VIIa)

The synthesis starts from estradiol, an estrogen that is commercially-available.

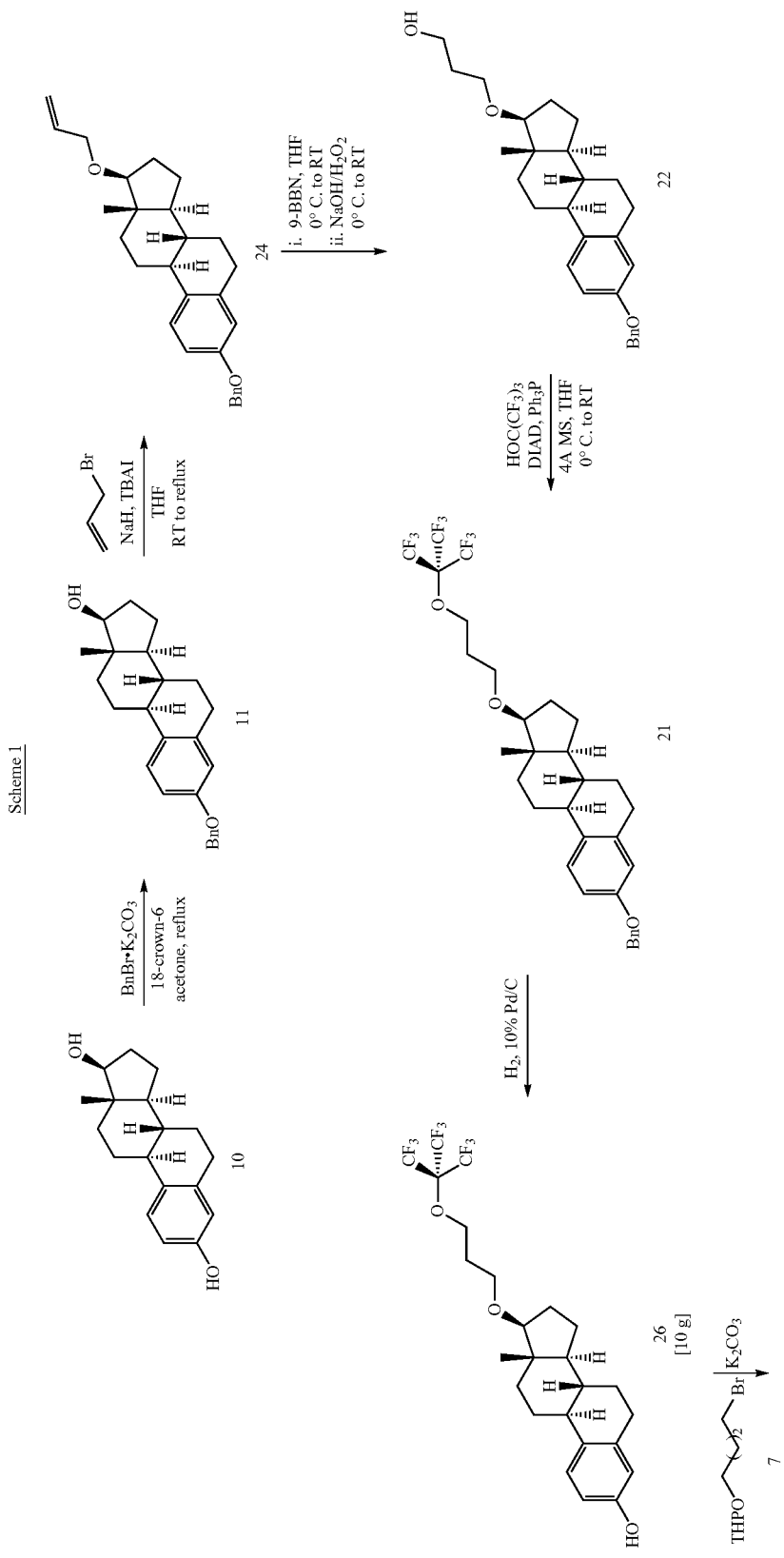

-continued
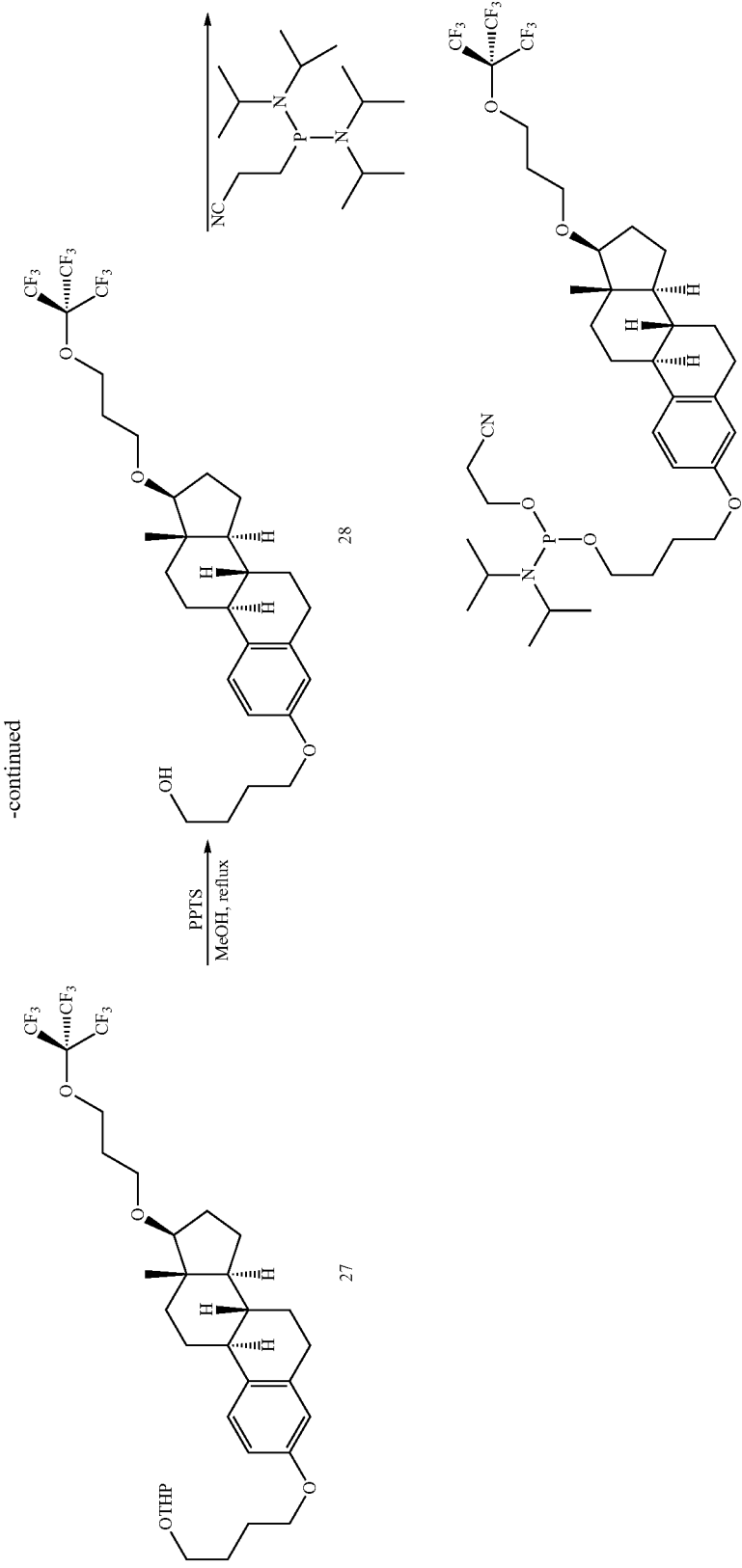

Synthesis is performed according to Scheme 1. For example, estradiol was protected by a benzyl group to provide compound 11. Allylation of alcohol 11 (25.6 g) under optimized reactions conditions (allyl bromide, NaH, cat. TBAI, THF, reflux, 16 h) afforded allyl ether 24 (21.85 g, 77%) as a white solid (purified by successive trituration in heptane and MeOH). Regio-selective hydroboration of the terminal alkene 24 (21.8 g) with 9-BBN, upon standard oxidative workup (NaOH/H$_2$O$_2$) provided alcohol 22. Mitsunobu reaction of the alcohol 22 (13.6 g) with excess perfluoro-tert-butanol under optimized reaction conditions (DIAD, PPh$_3$, 4 A MS, THF, RT, 16 h) afforded the desired ether 21. Compound 21 was subjected to catalytic hydrogenation (10% Pd/C, RT) using a mixture (1:1) of THF and 2,2,2-trifluoroethanol as solvent (5 bars, Parr reactor) to afford (after ~18 h) the phenol 26 as off-white solid. Debenzylation was then performed, followed by alkylation, using a THP-protected bromobutanol. The protecting group was then removed, followed by attachment of the phosphoramidite group, as the last step to the desired compound. This Product was then subjected to conjugation to the oligonucleotide chain, via the phosphoramidite group, as the final building block of synthesis of the oligonucleotide chain, at the 5'-end.

Example 2b

A Method for Synthesis of the E Moiety According to Formula (XVI)

The synthesis starts with lithocholic acid, a bile acid that is commercially-available. The synthesis follows synthetic Scheme 2:

Scheme 2

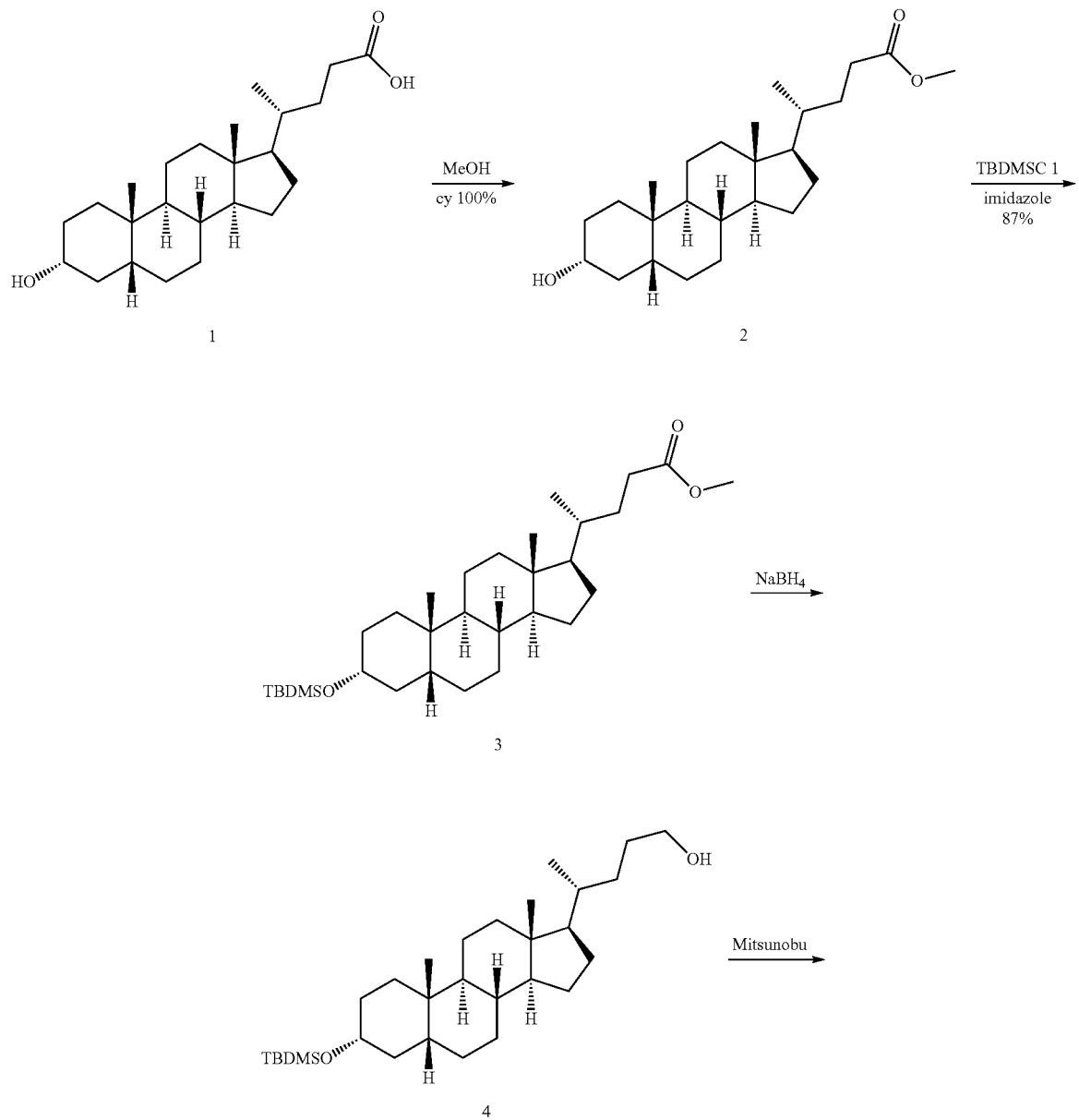

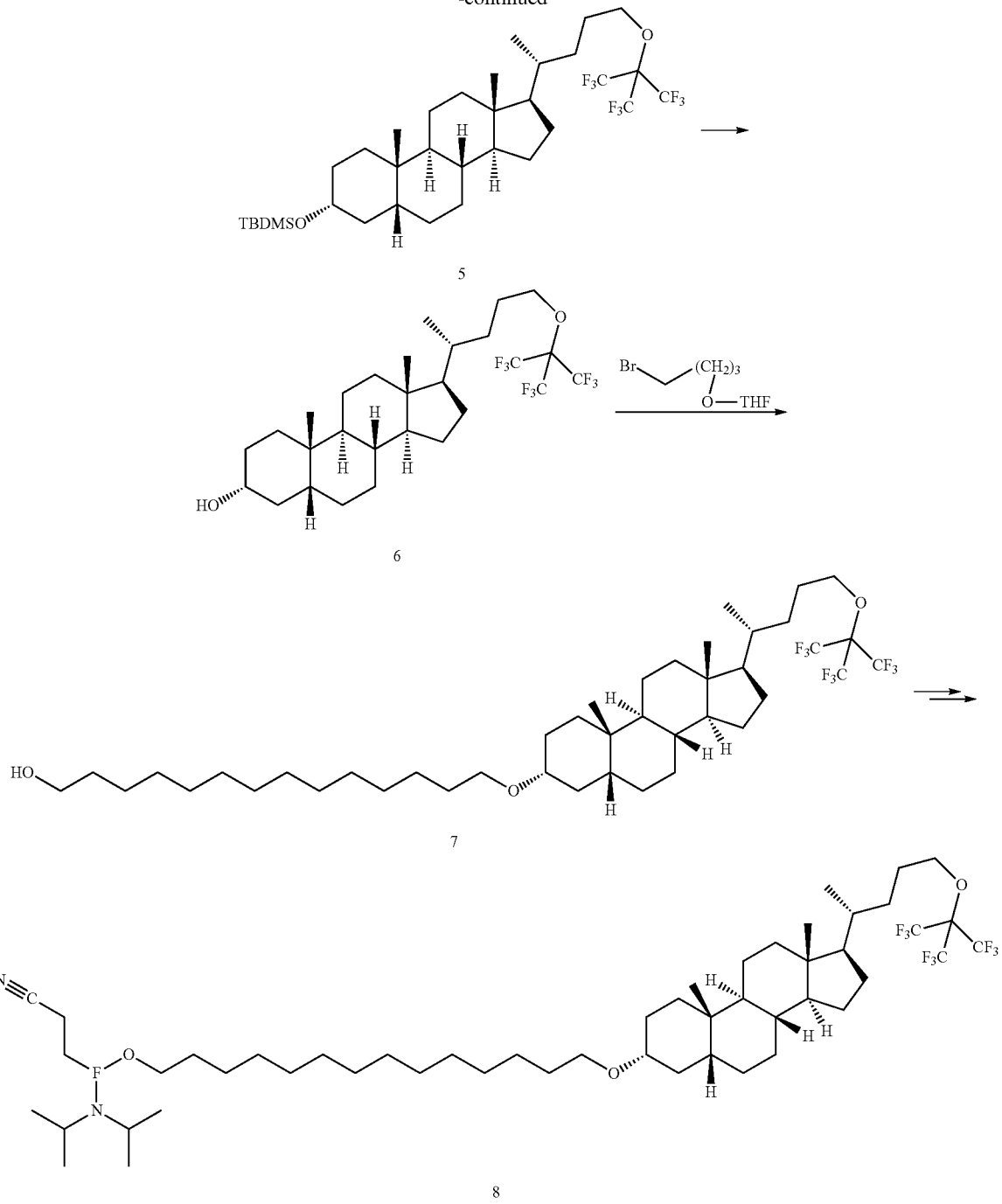

For example, 25 g of material 1 were converted to corresponding methyl-ester in a quantitative yield. 25 g of material 2 were reacted with TBDMSCl NS 29 g (87%, NMR). Pure compound 3 was obtained. Reduction of compound 3 (29 g) to 4 with NaBH$_4$ THF/MeOH gave, after work up and purification, compound 4 (85%) by NMR, still with some traces of compound 3. Mitsunobu reaction of material 4 with perfluoro t-butanol gave, after work-up column chromatography and trituration from MeOH, 33.5 g (92%) of compound 5, which was de-protected thereafter, to give steroid 6. Steroid 6 (2.5 g) was then coupled to THP-protected bromotetradecanol. The coupling took 3 days, and 4 equivalents of THP-protected bromotetradecanol were needed to reach complete conversion. The product was purified by column chromatography. After removal of the protecting group (THP) with MeOH/1,4-dioxane (HCl, 4 N)/THF, product 7 was purified by column chromatography to remove impurities. Product 7 (1.5 g, c.y. 48%) was obtained as white solid. Product 7 was then converted into the desired compound 8, by attachment of the phosphoramidite group. This Product was then subjected to attachment to the oligonucleotide chain, as the final building block of synthesis of the oligonucleotide chain, at the 5'-end.

Example 2c

A Method for Synthesis of the E Moiety According to Formula (IX)

Intermediate 26 is synthesized as described in Example 2a. Then the synthesis is performed according to the following Scheme 3.

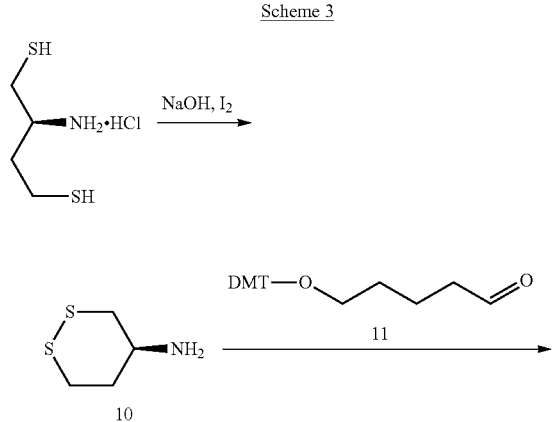

Scheme 3

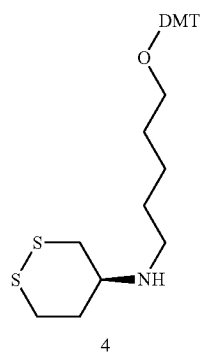

For example, dithiol-butyl amine (0.5 g) with iodine under basic conditions afforded the 1,2-dithiane 10 (3.13 g, 90%) as a crystalline-white solid. The alcohol corresponding to intermediate 11 is commercially-available, and was protected with dimethoxytrityl (DMT). Reductive amination with amine 10 (258 mg) in presence of $NaBH(OAc)_3$ afforded the desired secondary amine 4 (330 mg, 91%) as major product. Intermediate 26 is then attached to intermediate 4 through carbmoylation, as known in the art. DMT is then removed, and a phosphoramidite group is attached, to yield a precursor compound. This precursor is then subjected to conjugation to the oligonucleotide chain, as the final building block of the chain, at the 5'-end. Linkage is performed through an oxygen atom. Said conjugation yields the desired Conjugate, comprising an E moiety according to Formula (IX).

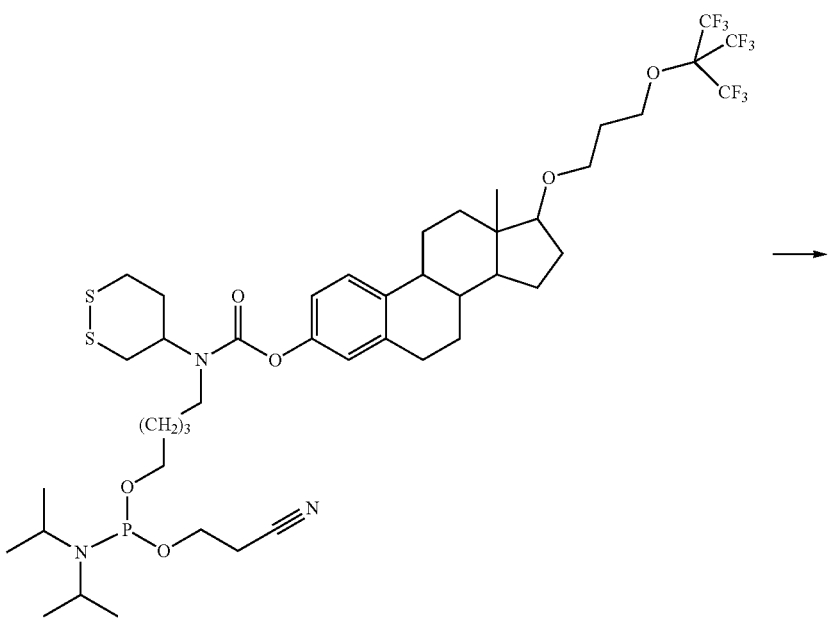

Scheme 4

Precursor as per Formula (XVII)

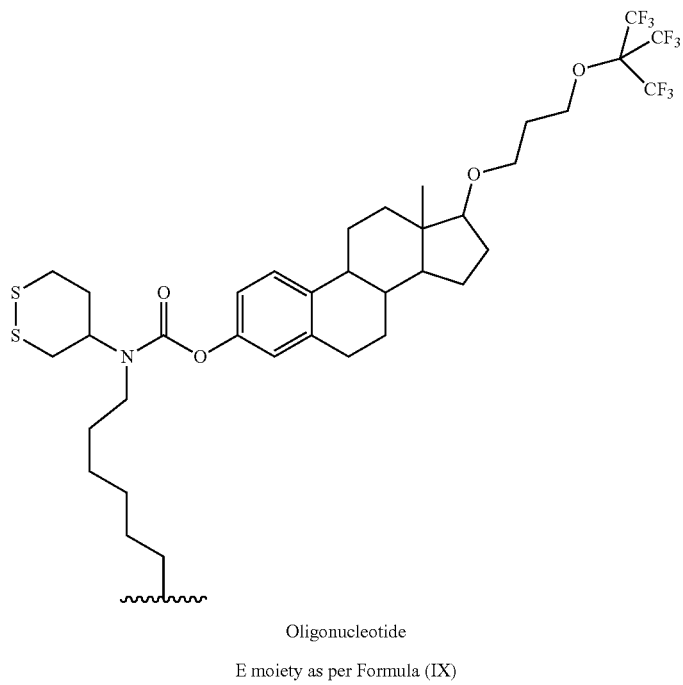

Oligonucleotide

E moiety as per Formula (IX)

Example 3

Examples of Conjugation of MNMs to Oligonucleotide Chains

Examples of structures of precursors; and respective compounds, when conjugated to an oligonucleotide chain.

a. 5' Modification:
Precursor:

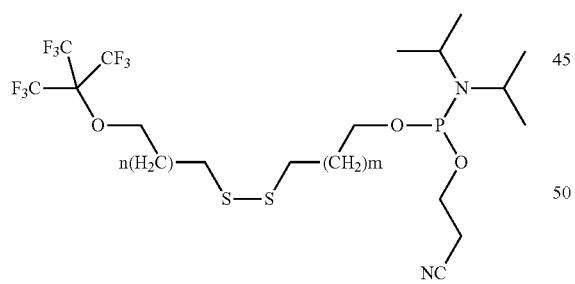

As attached to an oligonucleotide:

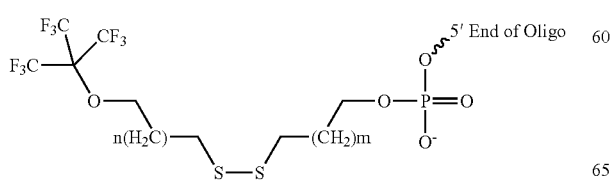

b. 3' Modification:
Precursor:

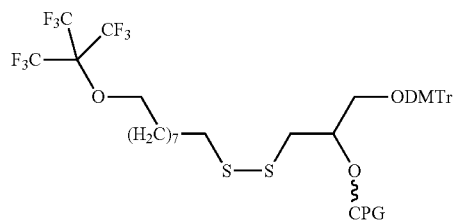

wherein DMT=Dimethoxytrityl; and CPG=Controlled Pore Glass (CPG) as a solid support for the synthesis of the oligonucleotide.

As attached to an oligonucleotide:

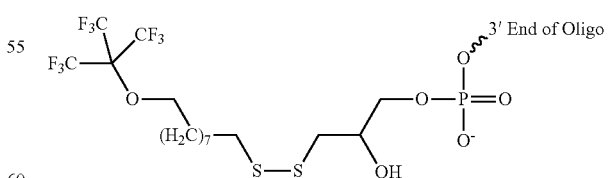

c. 5' Internal Modification:

In this modification, E comprises a nucleotide (e.g., thymine): This modification can serve for attachment of an E moiety within an oligonucleotide chain, rather than at a terminal position.

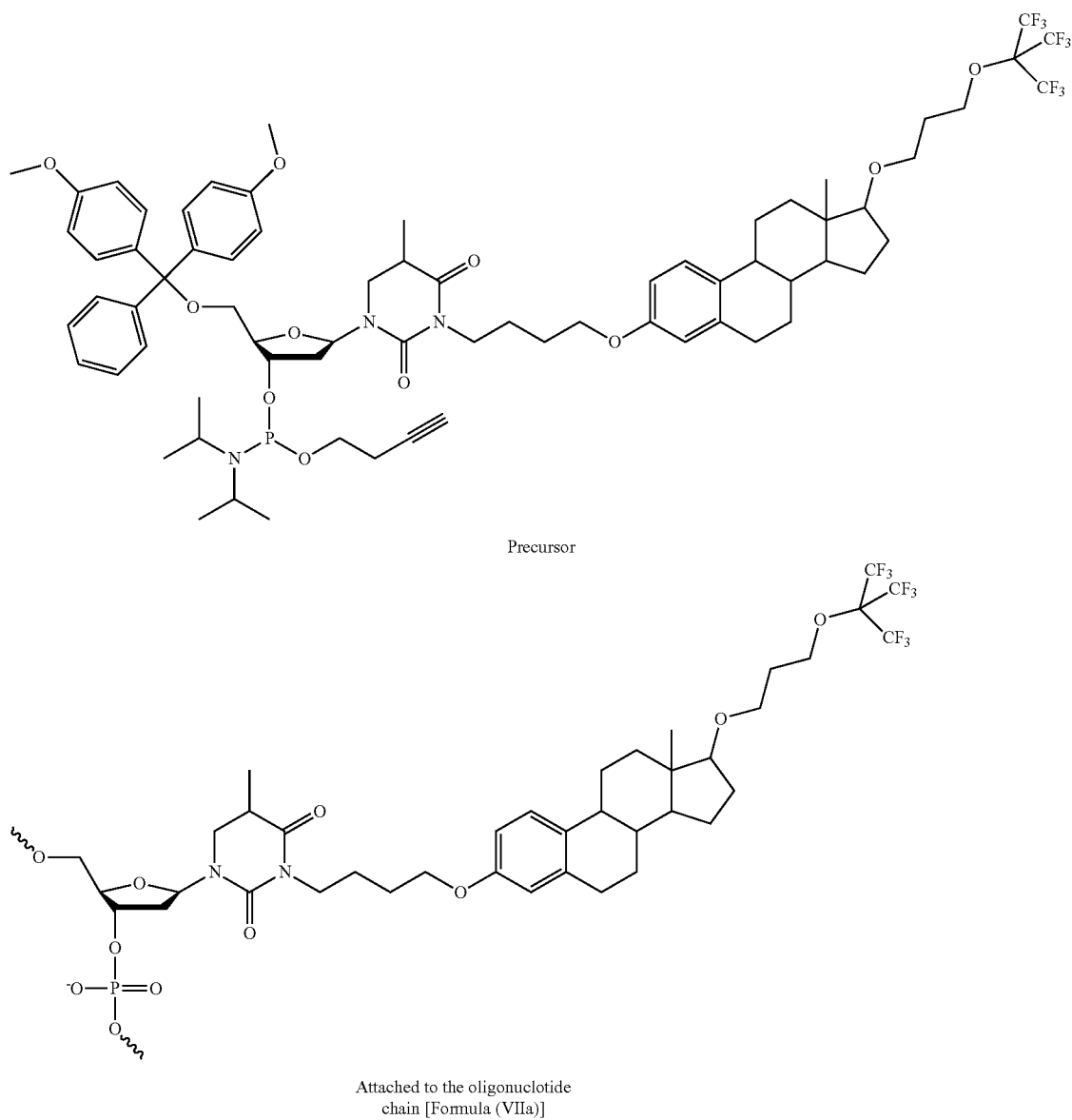

Precursor

Attached to the oligonuclotide chain [Formula (VIIa)]

Example 4

An Exemplary Structure of a Conjugate of the Invention, Comprising a Protein (for Example, without Limitation Cas9), Conjugated to E Moieties of the Invention

Figure 4:
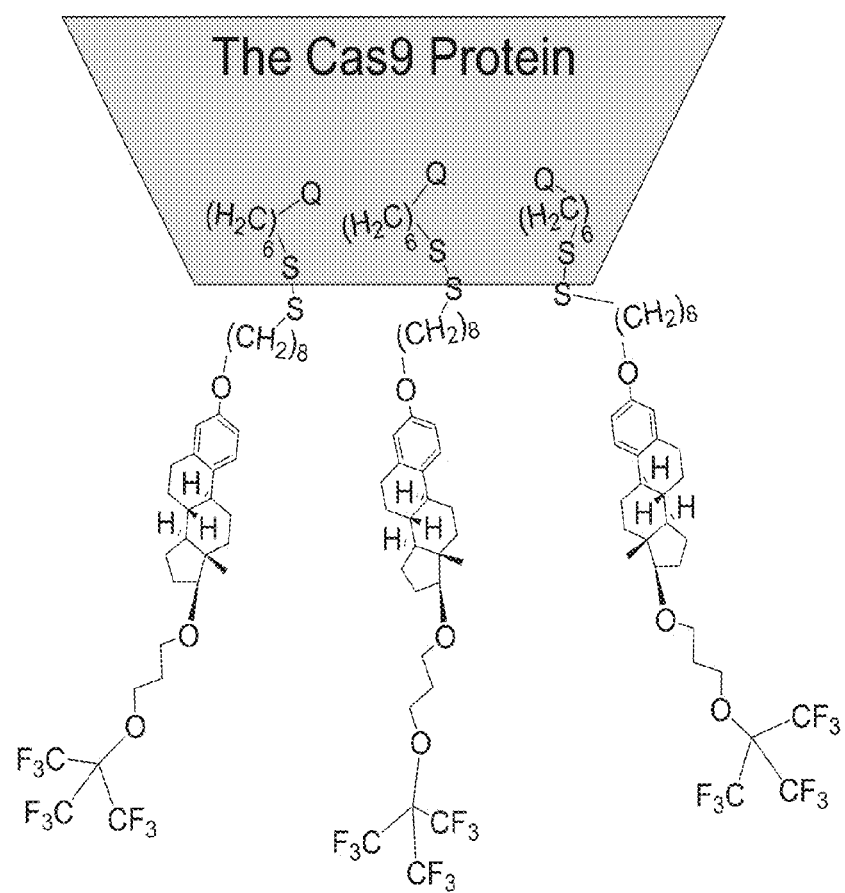
FIG. 4 shows an exemplary structure of a Conjugate of the invention, comprising a protein (for example without limitation Cas9) and E moieties as set forth Formula I.

A structure of an MNM of the invention, conjugated to the Cas9 protein is schematically illustrated in FIG. 4. MNMs E, E' or E" according to embodiments of the invention are attached through a linker group to the protein. Binding is performed through carbamate or amide bonds to lysine side-chains on the protein surface. For attachment, active esters are used. For this purpose, the alcohol is converted to an active ester (e.g., N-hydroxysuccinimide, NHS), that preferentially reacts with nitrogen of the protein lysine side-chains over oxygen (water). Reaction is performed according to the following Scheme:

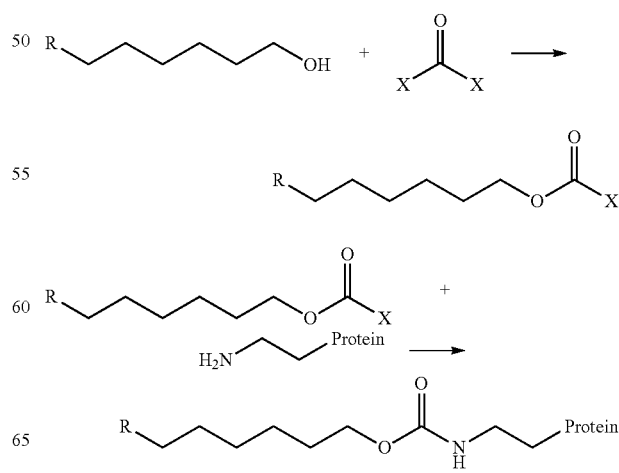

Possible derivatizing agents are:
a) Phosgene: linkage is through chloroformate ester.
b) Disuccinimidyl carbonate (X=N-hydroxysuccinimide): linkage is through a succinimidyl carbonate.
c) Carbonyldiimidazole (CDI, X=Imidazole): linkage is through imidazolyl carbamate.

Protein labeling with any of these groups takes place in an amine-free (not Tris), slightly basic buffer (pH=8-9). The linkage point is hydrophobic, thus requiring a co-solvent (normally DMF or DMSO) for the reaction with proteins to take place. High reactivity means, on the one hand shorter reaction times, but, on the other hand also lower nitrogen over oxygen selectivity, and shorter lifetime in aqueous buffer. When the product is a carbamate, it may be susceptible to enzymatic cleavage. Of the three options above, carbonyl-di-imidazole has the highest nitrogen over oxygen selectivity, as well as the simplest synthesis, and is therefore preferred. On the other hand, carbonyl-di-imidazole is associated with a longer protein derivatization time (probably overnight). The number of E, E' or E" moieties per protein molecule is determined by pre-setting of the desired molar ratios.

Example 5

Cellular Uptake of Conjugates, Comprising DNA Oligonucleotides, Conjugated to One or Two Molecular NanoMotors of the Invention In the following Examples, cellular uptake of Conjugates, comprising Apo-Si MNMs according to Formula (XI) or Formula (XVI) is provided, attached to either Cy3-labeled single-stranded 29-mer DNA sequence (carrying 29 negative charges), or to a double-stranded 58-mer DNA sequence (carrying 58 negative charges) is described. The sequences of the DNA oligonucleotides were 5' Apo-si-TT-iCy3-CG-GTGGTGCAGATGAACTTCAGGGTCA (SEQ ID NO: 1) and 5'Apo-si-TGACCCTGAAGTTC ATCTGCACCAC-CGAA (SEQ ID NO: 2). iCy3 means the fluorophore Cy3, at an internal position along the sequence). These sequences (synthesized, for example without limitation, by IDT, Iowa, USA) were chosen randomly, aimed at serving as an example for the trans-membrane delivery into the cells. The incorporation of the fluorophore served as a tool to detect the location of the examined Conjugate. Performance in various cell lines is presented, to demonstrate that the trans-membrane delivery of macromolecules by the Apo-Si MNMs is universal, and is not limited to a specific cell type.

Example 5a

3T3 Cells

Figure 5A:
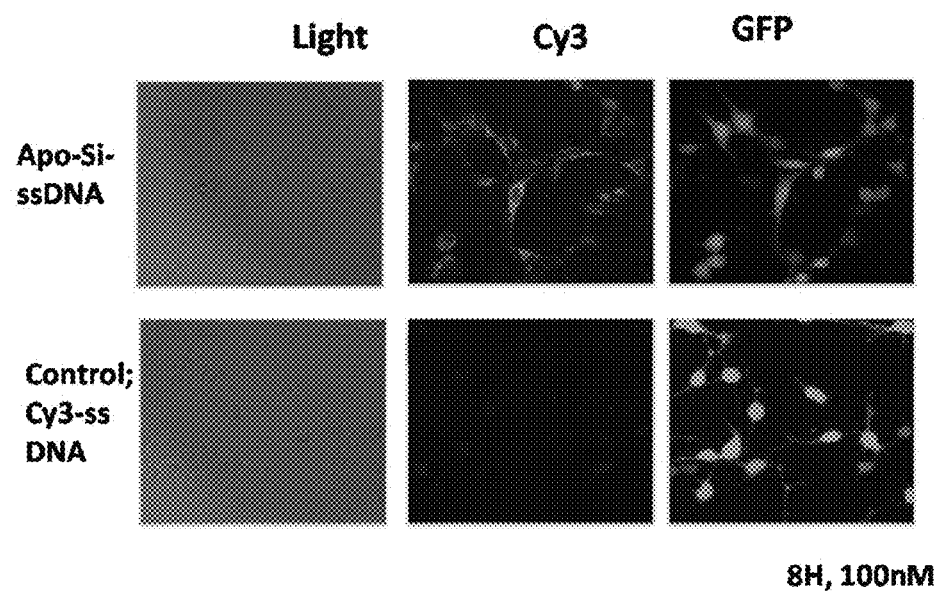
FIGS. 5a-5f, 6a-c and 7-9 exemplify the biological performance in vitro of conjugates according to embodiments of the invention, comprising MNMs of the invention, having the structure as set forth in either Formula (XI) or Formula (XVI)

In order to assess the ability of an MNM of the invention to deliver a 29-mer single strand DNA (ssDNA) oligonucleotide into cells, an assay in vitro was performed. One day before experiment, NIH-3T3 cells, stably transfected with the EGFP protein (3T3-EGFP cells) in the exponential growth phase, were plated in 24-well plates, at a density of $4.5 \times 10^4$ cells/well with DMEM, plus supplement growth medium (500 µl/well), without antibiotics. Initially, a Cy3-labeled 29-mer ssDNA oligonucleotide, having the sequence of 5'Apo-si-TT-iCy3-CGGTGGTGCAGATGAACTTCA-GGGTCA (SEQ ID NO: 1). This sequence was conjugated to a single MNM. The uptake of this Conjugate into the cells was compared to the uptake of a control compound, being the same DNA strand, with Cy3, but without the MNM. The Conjugate was diluted in 100 µl/well of Opti-Mem (Life technologies-Cat. 31985062, USA), incubated for 10 minutes in room temperature, and added to the cells at a final concentration of 100 nM. Uptake of the Conjugate by the cells versus Control was evaluated at 8 hours of incubation. At the end of the incubation period, cells were washed with Hank's Buffered Salt Solution (HBSS buffer; Biological Industries, Israel) and subjected to analysis. Cells were visualized using an Olympus fluorescent microscope (BX51TF; Olympus Optical, U.K.), with UV illumination from a mercury lamp (×20 magnitude). The Cy3-fluorophore was visualized with an excitation wavelength of 470-495 nm and emission at 590 nm, while the EGFP fluorophore was visualized with excitation at 530-550 nm and emission at 510-550 nm. As shown by fluorescent microcopy in FIG. 5a, Apo-Si-11, comprising the MNM linked to a 29-mer DNA strand, manifested efficient delivery across cell membranes into the 3T3-EGFP cells, in contrast to the Control oligonucleotide without the MNM, in which no significant uptake was observed.

Figure 5B:
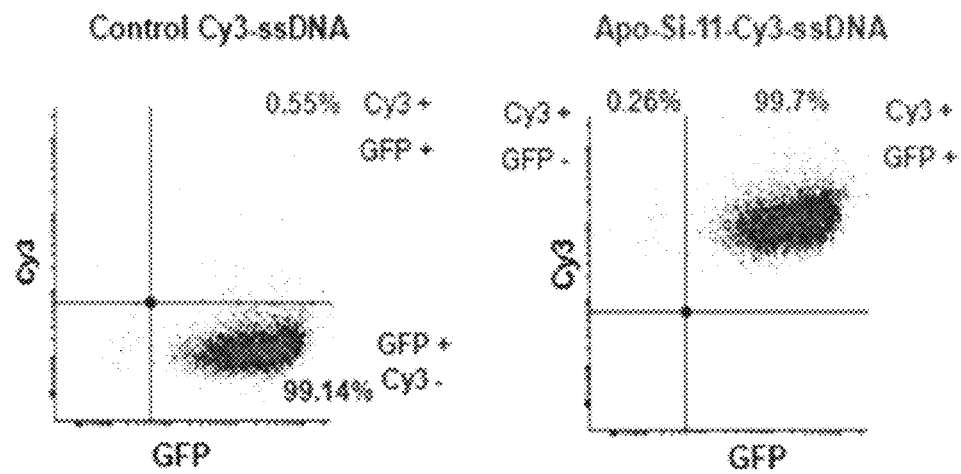
Figure 5C:
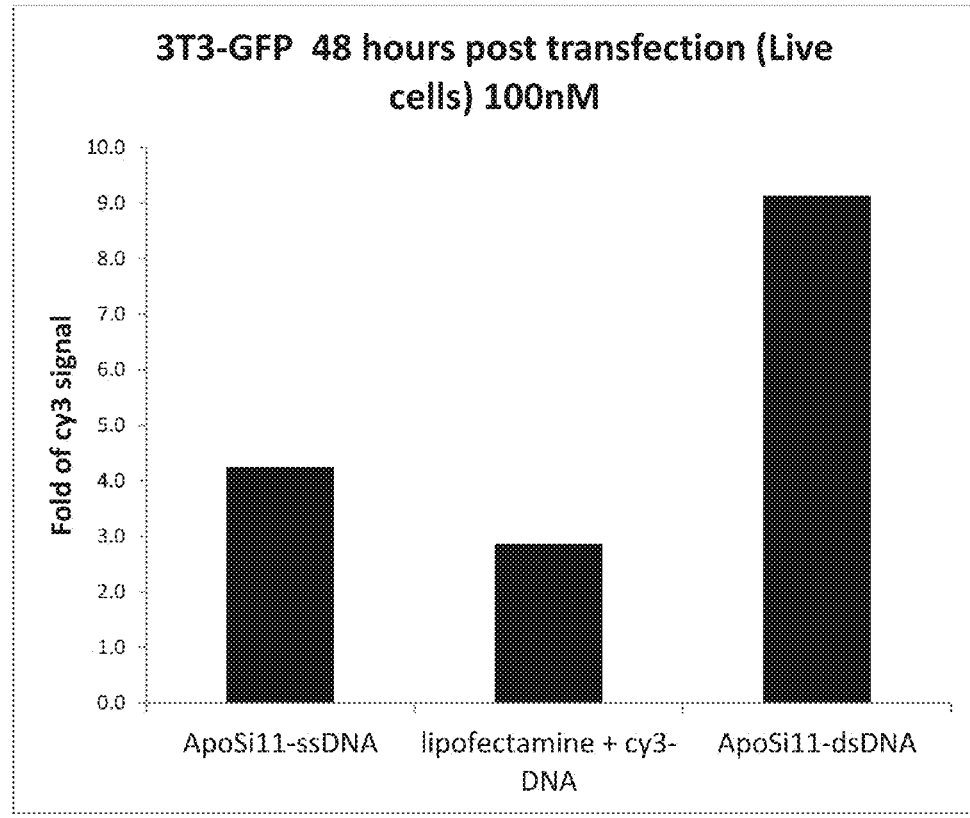

The ability of the Apo-Si MNM to the deliver 29-mer ssDNA oligonucleotide to 3T3-EGFP cells was also quantified using an ELISA reader (FIG. 5c). For this purpose, cells at an exponential growth phase were plated one day before the experiment in 24-well plates at a density of $4.5 \times 10^4$ cells/well with DMEM, plus supplements growth medium (500 µl/well) without antibiotics. Each Cy3-labeled oligonucleotide was diluted in 100 µl/well of Opti-Mem), and added to the cells, at a final concentration varying from 40 to 100 nM. The accumulation of the Apo-Si MNM-Conjugate within the cells versus the Control Compound without MNM was evaluated at 24 h of incubation. For this purpose, cells were washed with HBSS buffer and subjected to analysis. Detection and quantification of Cy3-positive population was performed using Tecan Infinite® 200 PRO multimode reader (excitation wave length 548±4.5 nm and emission 580±10 nm). Uptake of the Apo-Si MNM Conjugate was compared to the uptake of the control DNA oligonucleotide at the same concentrations, and results were expressed as percentage, compared to Control. As shown in FIG. 5c, significant uptake of the Conjugate into the cells was observed, as compared to Control.

Cellular uptake of the Apo-Si MNM, linked to a 29-mer DNA oligonucleotide was also evaluated by flow cytometric analysis (FACS). As described above, one day before the experiment, 3T3-EGFP cells in the exponential growth phase were plated in 6-well plates, at a density of $1.5 \times 10^5$ cells/well, with DMEM complete medium, without antibiotics. Each of the Cy3-labeled oligonucleotides was diluted in 500 µl/well of Opti-Mem, and added to the cells at a final concentration varying from 1 to 40 nM. Delivery of the Conjugate was evaluated at 24-72 h post transfection. Following the incubation period, cells were trypsinized, supplemented with Hank's Buffered Salt Solution (HBSS buffer; Biological Industries) and centrifuged for 5 min at 1100 rpm. Cells were then re-suspended with Hank's Buffered Salt Solution, and subjected to analysis using FACSAria III Cell Sorter (BD Biosciences, San Jose, Calif.), utilizing the Cell Diva software. For each sample, a total of $10^4$ events were collected. Detection and quantification of the Cy3-positive cell population were performed using measurements of the fluorescence intensity in the cells incubated with the Apo-Si-11 Conjugate, relative to that of the cells incubated with the control oligonucleotide, having the same sequence, but devoid of the MNM.

FACS analysis confirmed that Apo-Si MNM is capable of efficient delivery of a 29-mer ssDNA oligonucleotide to 3T3-EGFP cells. FIG. 5b provides a dot plot analysis, showing that in the cell population incubated with the Apo-Si-11 Conjugate, practically all cells manifested uptake of the Conjugate, in contrast to Controls.

Figure 5D:
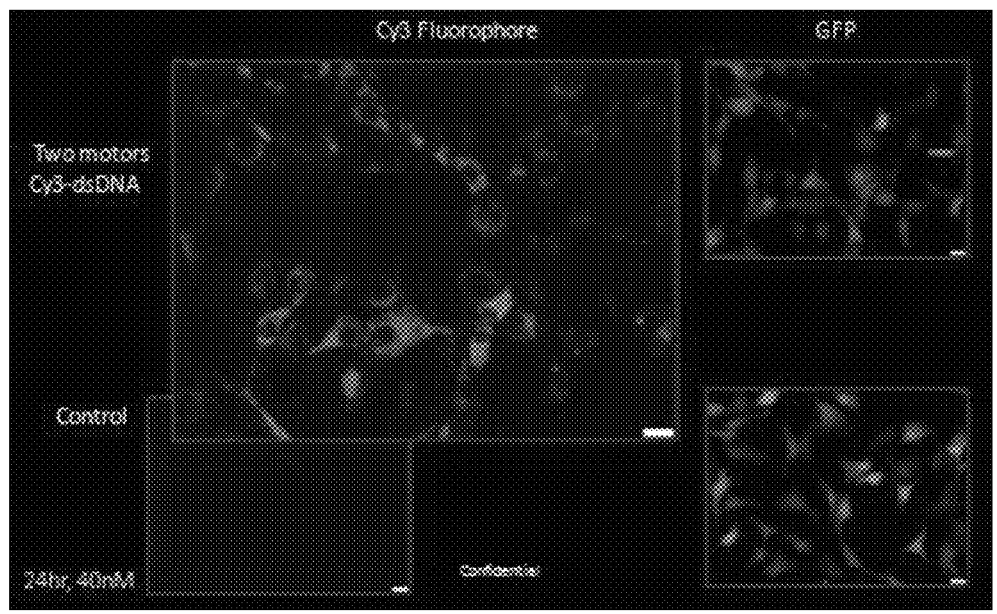

We then assessed the ability of Apo-Si-11 to deliver double-stranded oligonucleotide (dsDNA) across the cell membranes. For that purpose, two Apo-Si-11 nanomotors were attached, one at each 5'-end of a 29 bp dsDNA oligonucleotide, labeled by the cy3 fluorophore. Sequence of the dsDNA was as described above: 5'Apo-si-TT-iCy3-CGGTGGTGCAGATGAACTTCAGGGTCA (SEQ ID NO: 1) and 5Apo-si-TGACCCTGAAGTTCATC TGCACCAC-CGAA (SEQ ID NO: 2). Attachment of the MNM to the oligonucleotide was performed as exemplified in Example 3 above. 3T3-EGFP cells were incubated with 40 nM of the Conjugate, and cellular uptake was evaluated by fluorescent microscopy at 24 h of incubation, and was compared to the uptake by cells incubated with a Control identical oligonucleotide, devoid of the MNMs. As described in FIG. 5d, two Apo-Si-11 MNMs were capable of efficient delivery of the 58-mer dsDNA oligonucleotide into the 3T3-EGFP cells.

Figure 5E:
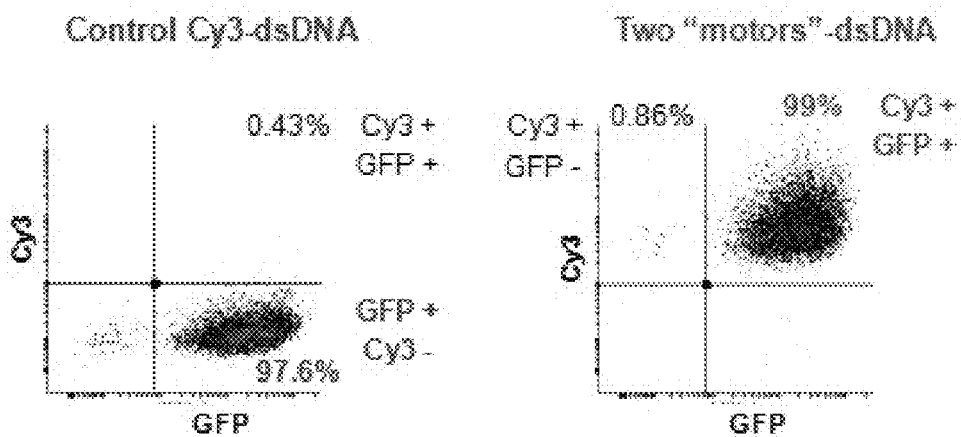
Figure 5E:
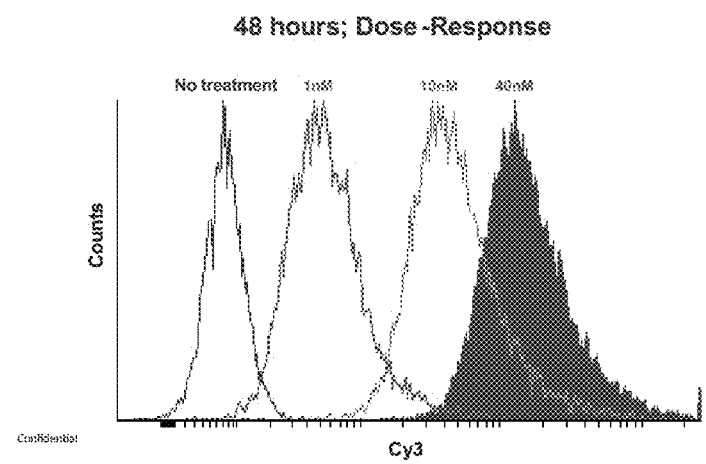

This delivery was further demonstrated by FACS. For this purpose, 3T3-EGFP cells were plated in 6-well plates, and treated as described in FIG. 5C. Each of the Cy3-labeled oligonucleotide (with and without the MNMs) was diluted in 500 µl/well of Opti-Mem, added to the cells at final concentrations of 40 nM, 10 nM and 1 nM. Following a 24 h incubation period, delivery of the oligonucleotides was evaluated by FACSAria III Cell Sorter (BD Biosciences, San Jose, Calif.) and analyzed by Cell Diva software. A total of $10^4$ events were collected for each sample. Detection and quantification of Cy3-positive population were performed using measurements of the fluorescence intensity in the cells incubated with the Apo-Si MNM Conjugate, relative to that of the cells exposed to the Control Oligonucleotide devoid of the MNMs. As shown in FIG. 5e, FACS analysis confirmed that two Apo-Si MNMs are capable of efficient delivery of a 58-mer dsDNA oligonucleotide into 3T3-EGFP cells: (i). Dot plot analysis, showing that only cells incubated with the Apo-Si-11 Conjugate manifested uptake of the Conjugate, which accumulated in practically all cells; (ii). Histogram geomean analysis, indicating a marked signal in the Apo-Si MNM-Conjugate-treated cells, in contrast to low, background levels in cells treated by the Control oligonucleotide devoid of the molecular nanomotors. A clear dose-response was observed in the examined concentrations (40 nM, 10 nM, and 1 nM).

Figure 5F:
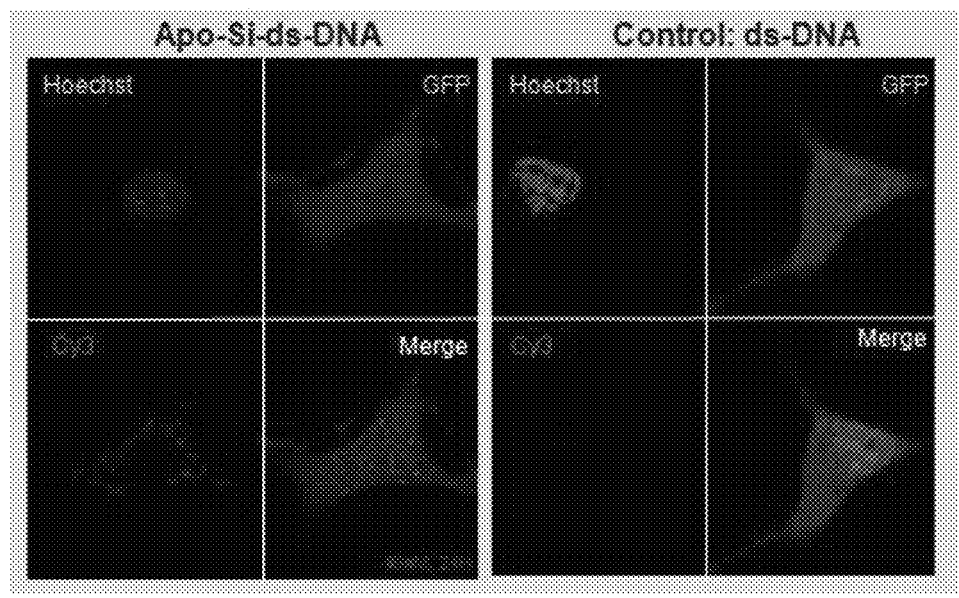

We then used confocal microscopy, in order to further confirm uptake and cytoplasmic localization of the Conjugate, attached to two Apo-Si-11 MNMs. Cells were prepared as described above. Nuclear staining with the Hoechst 33258 dye (Sigma Aldrich, USA, 1:1000 in HBSS for an hour) was also performed. As shown in FIG. 5f, the Apo-Si Conjugate manifested efficient uptake through the cell membranes and accumulation, as desired, within the cytoplasm.

Example 5b

Murine B16 Melanoma Cells

The objective was to determine the capability of a Conjugate, comprising two Apo-Si MNMs (each attached at a 5'-end of the strand), to perform uptake into cultured B16 murine-skin melanoma cells. For this purpose, B16 cells were grown and maintained as described in Example 5a. Briefly, cells were grown in DMEM (Sigma Aldrich, USA), supplemented with 10% FBS, 2 mM L-glutamine and 1% Pen-Strep at 37° C., in a humidified incubator containing 5% $CO_2$. One day before transfection, $2 \times 10^4$ B16 cells were plated in standard 24-well plate chambers. 40 nM of Cy3-labeled 58-mer double-stranded DNA, conjugated to the Apo-si-11 MNMs were incubated with the cells for 24 hours in the presence of complete growth medium. An identical Cy-3-labeled oligonucleotide, devoid of the Apo-Si MNMs, was used as control, and was incubated with the cells for the same time-period. Each well was washed twice with HBSS before quantification of Fluorescence. Microscopy figures were taken with an Olympus BX51 microscope, as described above.

The B16 cells were also subjected to FACS analysis. For this purpose, one day before transfection, $16 \times 10^4$ B16 cells were seeded in standard 6-well plates. Ten and 40 nM of Cy3-labeled 58-mer dsDNA, conjugated to two Apo-si-11 MNMs were incubated for 24 hours with complete growth medium. A Cy3-labeled 58-mer DNA, devoid of the MNMs was used as control. Cells were washed with HBSS, and analyzed for fluorescence intensity with the BD FACSAria™ III as described above.

In addition, confocal microscopy was used, in order to further confirm uptake and cytoplasmic localization of the Apo-Si MNM conjugate, comprising the two MNMs. Cells were prepared as described above. Nuclear staining with the Hoechst 33258 dye (Sigma Aldrich, USA, 1:1000 in HBSS for about an hour) was also performed.

Figure 6A:
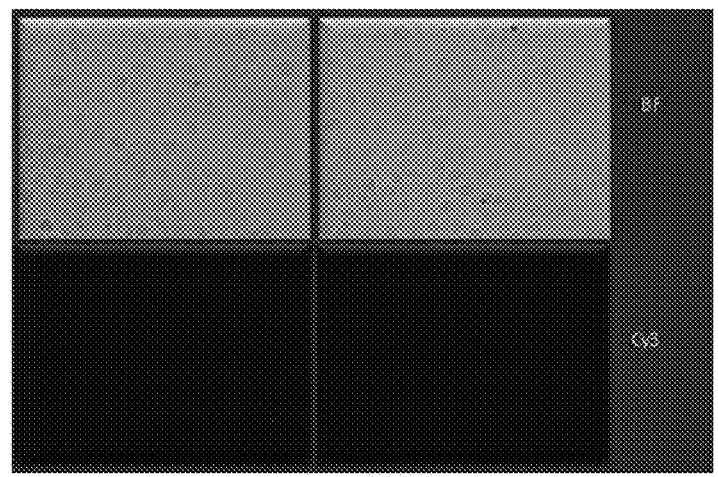
Figure 6A:
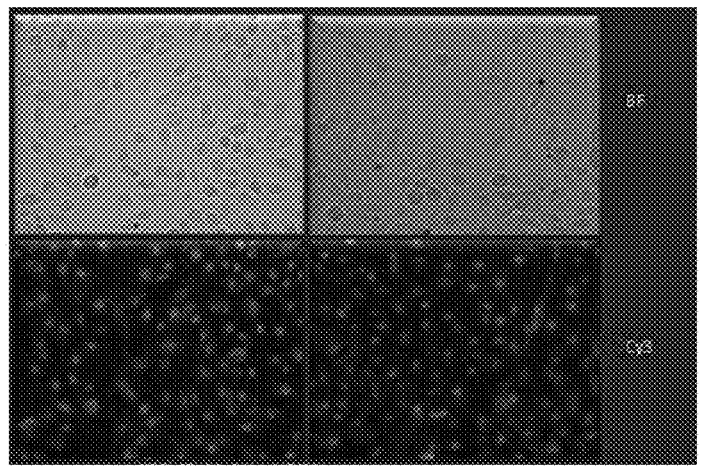
Figure 6B:
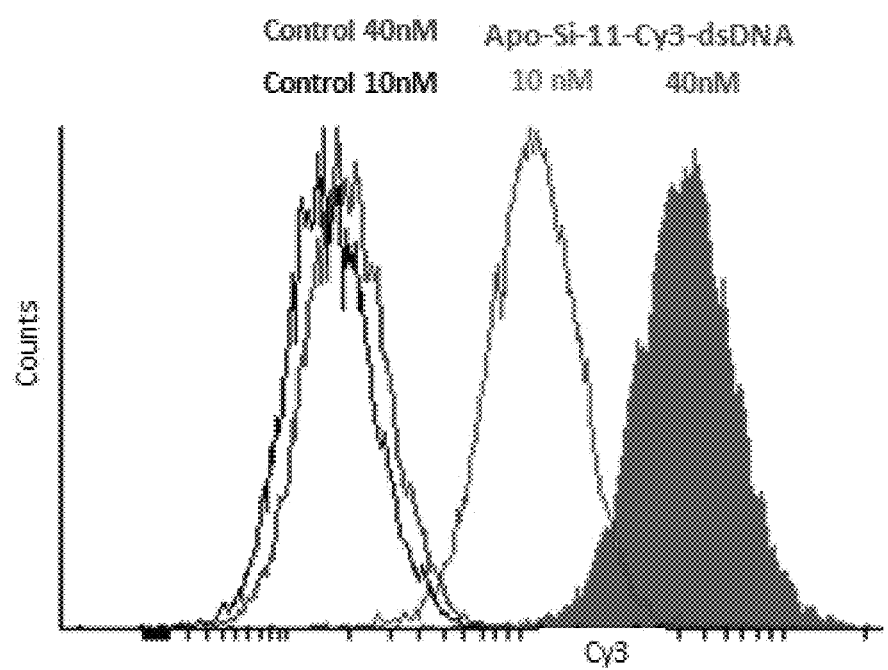
Figure 6C:
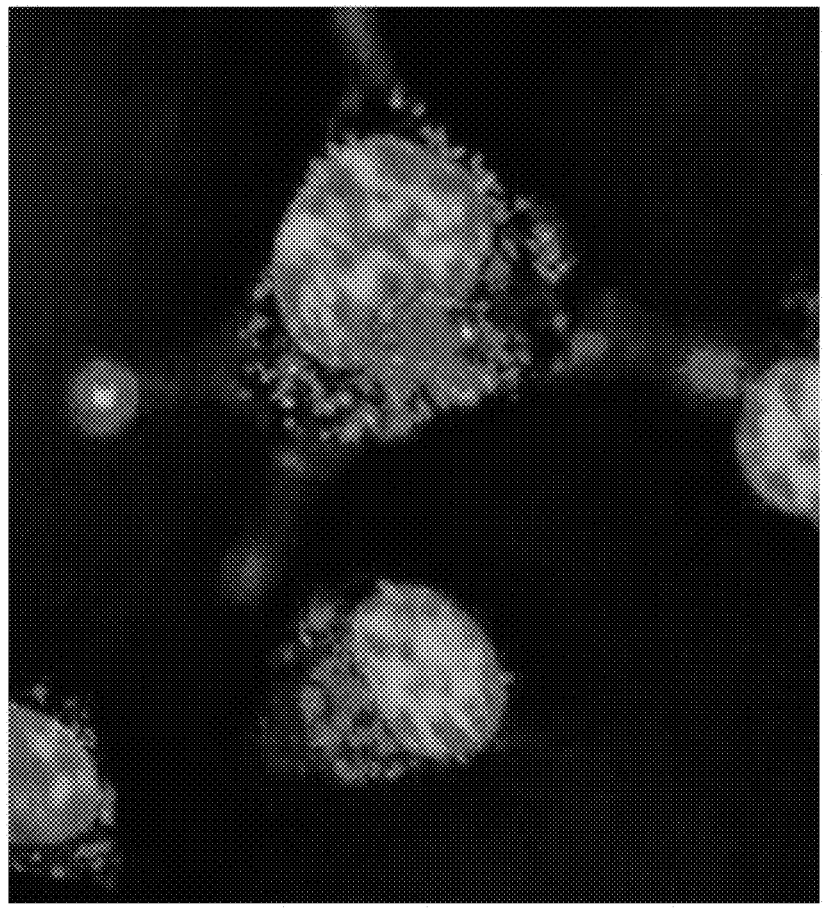

Marked uptake was detected in cells treated with the Apo-Si MNM Conjugate comprising 58-mer double-stranded DNA, but not in the cells exposed to an identical Cy3-labeled oligonucleotide but devoid of MNMs. This was evident in the fluorescent microcopy (FIG. 6a), as well as in the FACS analysis (FIG. 6b). At 40 nM, the Apo-Si MNM Conjugate manifested uptake by 98% percent of cells. A clear dose-response was observed, comparing signal intensities at 40 nM versus 10 nM. Confocal microscopy (FIG. 6c) further showed efficient uptake of the Apo-Si Conjugate through cell membranes, and accumulation in the cytoplasm.

Thus, Apo-Si MNM enables efficient delivery of a 58-mer ds-DNA oligonucleotide into B16 melanoma cells line, in a dose-dependent-manner.

Example 5c

C26 Murine Colon Adenocarcinoma Cells

In order to demonstrate the capability of Apo-Si MNMs, to enable delivery of heavily-charged 58-mer dsDNA into C26 colon adeno-carcinoma cells, cells were grown and maintained as described above. Briefly, cells were grown in DMEM, supplemented with 10% FBS 2 mM L-glutamine and 1% Pen-Strep, at 37° C. in a humidified incubator, containing 5% CO2.

Cells were subjected to FACS analysis. For this propose, one day before transfection, $16 \times 10^4$ C26 cells were seeded in a standard 6-well plates. 40 nM of the 58-mer double-stranded DNA, conjugated to two Apo-Si MNMs, each at a 5'-end of the oligonucleotide, and linked to the Cy3 fluorophore, were incubated for 24 hours in the presence of complete growth medium. The same construct, devoid of the Apo-Si MNMs, served as Control. Cells were washed with HBSS and analyzed for fluorescence intensity with the BD FACSAria™ III as mentioned above.

Figure 7:
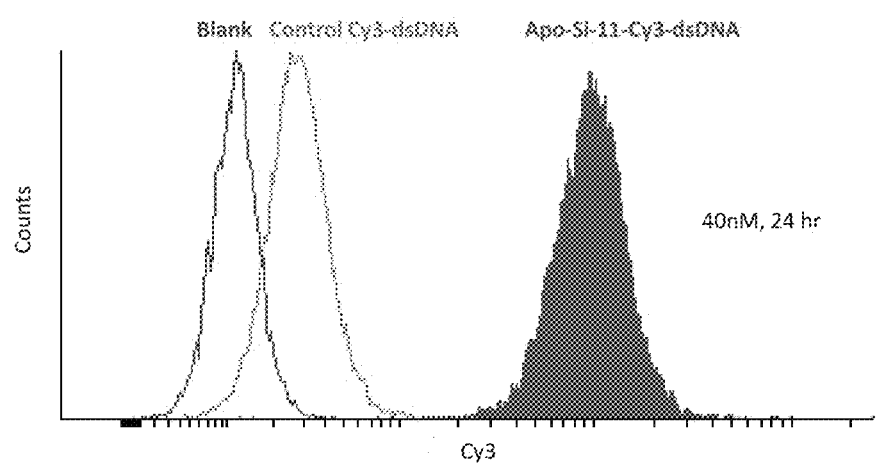

As shown in FIG. 7, marked Cy3 fluorescence was detected in 98% of cells treated with the Apo-Si Conjugate. Such uptake was not detected in the cells exposed to the control oligonucleotide. Therefore, the Apo-Si MNMs enabled efficient trans-membrane delivery of the oligonucleotide.

Example 5d

Human HeLa Cell Line

The objective was to demonstrate the capability of Apo-Si MNMs to enable delivery of heavily-charged 58-mer dsDNA into HeLa human cervical epithelial carcinoma cell line. For this purpose, cells were grown and maintained as described above. Briefly, cells were grown in DMEM supplemented with 10% FBS 2 mM L-glutamine and 1% Pen-Strep at 37° C., in a humidified incubator, containing 5% $CO_2$.

For the FACS analysis, one day before transfection, $16 \times 10^4$ HeLa cells were seeded in standard 6-well plates. 40 nM of Cy3 labeled, 58-mer double-stranded DNA, conjugated to two Apo-Si MNMs were incubated for 24 hours in the presence of complete growth medium. Cy3-labeled 58-mer DNA was used as control. Cells were washed with HBSS and analyzed for fluorescence intensity with the BD FACSAria™ III system, as mentioned above. Cells, treated with 58-mer double stranded DNA, conjugated to Apo-Si MNM manifested marked uptake into nearly all cells in the culture (FIG. 8). By contrast, such uptake was not observed in the cells treated by the Control oligonucleotide. Therefore, in conclusion, Cy3 labeled, 58-mer double-stranded DNA, thus carrying 58 negative charges, and conjugated to two Apo-Si MNMs manifests efficient delivery into cultured human HeLa cell line.

Taken together, these results presented in Example 5, and obtained from four distinct cell types: 3T3 murine fibroblast cells, murine melanoma B16 cells, murine C26 colon carcinoma cells, and human HeLa uterine cervical carcinoma cells, demonstrate an efficient trans-membrane delivery and uptake of highly-charged macromolecules when linked to one or two Apo-Si MNMs. Such uptake was not observed in the control oligonucleotides, devoid of the MNMs. These data support the notion that the performance of the MNMs of the invention in enabling trans-membrane delivery of oligonucleotides is universal, and is not limited to a specific cell type.

Example 6

A Mechanism for Intracellular Entrapment of siRNA, Comprising Administration of a Dicer Substrate In an embodiment of the invention, it discloses a method for entrapment of siRNA in the cytoplasm following its successful trans-membrane delivery by the Conjugates of the invention. The method is based on the activity of the enzyme Dicer, an endocnulease which is capable of processing double-stranded RNA, by cutting it at the size of 19-21 base pairs, suitable for interaction with RISC (RNA Inducible Silencing Complex) for gene silencing. Said method comprises: (i). Administration of a Conjugate of the invention, wherein the oligonucleotide is a Dicer substrate, consisting of a double-stranded RNA of 25-30-nucleotide long, being of the sequence required for silencing a specific target gene; and conjugated to MNMs of the invention, attached each at the 3'-end of the sense (passenger) strand, and/or at the 5'-end antisense (guide) strand; (ii). Trans-membrane delivery of the siRNA, enabled by the MNMs; (iii). Cleavage of the dsRNA by the Dicer enzyme, thus removing one MNM from the Duplex; (iv) physiological subsequent separation of the double-helix (e.g., by the Helicase enzyme) leading to release of the antisense strand, to interact with RISC, in order to silence the specific target gene (FIG. 3).

In order to examine cleavage by Dicer in vitro, siRNA duplexes (100 pmol) were incubated in 20 ml of 20 mM Tris pH 8.0, 200 mM NaCl, 2.5 mM MgCl2, with 1 unit of recombinant human Dicer (Stratagene) for 24 h. A 3-ml aliquot of each reaction (15 pmol RNA) was then separated in a 15% non-denaturing polyacrylamide gel, stained with GelStar (Ambrex) and visualized using UV excitation. Electrospray-ionization liquid chromatography mass spectroscopy (ESILCMS) of the duplex RNAs before and after treatment with Dicer was then performed, utilizing an Oligo HTCS system (Novatia), consisting of ThermoFinniganTSQ7000, Xcalibur data system, ProMass data processing software and Paradigm MS4 HPLC (Michrom BioResources).

Example 7

Silencing of the EGFP Gene by a Conjugate of the Invention In Vitro

The biological system used for this demonstration is human HeLA cells, stably expressing the enhanced green fluorescent protein (EGFP) gene (NIH-HeLa EGFP cells). The administered Conjugate of the Invention comprised siRNA, designed to silence the expression of the EGFP gene. Normally, unless utilizing a transfection reagent, such RNA construct cannot pass through the cell membrane into the cytoplasm, where it can exert its gene-silencing activity. Due to conjugation of this siRNA to the MNMs of the invention [for example without limitation, E moieties having the structure as set forth in Formula (X)] gene silencing activity is enabled and observed, without the need for a transfection reagent.

For this purpose, cells were incubated with a Conjugate of the invention, comprising siRNA designed for silencing of the EGFP protein (IDT, Iowa, USA), linked to two MNMs according to Formula (XVI). The sequence of the double-stranded RNA was: Sense sequence 5' to 3': ACCCUGAAGUUCAUCUGCACCACCG (SEQ ID NO:

3); Antisense sequence 5' to 3': CGGUGGUGCA-GAUGAACUUCAGGGUCA (SEQ ID NO: 4). A respective double-stranded DNA sequence, linked to the MNM moiety served as Control, since such DNA construct cannot exert gene-silencing activity.

Specifically, one day before the experiment, NIH-HeLa EGFP cells at the exponential growth phase were plated in 24-well plates, at a density of $4.5 \times 10^4$ cells/well, with DMEM and supplements growth medium (500 μl/well), without antibiotics. The siRNA-Apo-Si-MNM Conjugate was diluted in 100 μl/well of Opti-Mem (Life technologies), and added to the cells, at a final concentration of 40 nM.

of a highly-charged 58-mer ds-DNA, in comparison to the controls, devoid of the MNM moieties. Notable are also the observed dose-response, and the observation that the uptake was not saturable, at least not at the examined dose-range.

Example 9

Mechanism of Redox-Sensitive Cleavage of the Conjugate of the Invention According to Formula (XI), and its Utilization for Targeting the Cargo Drug (D) to the Cytoplasm

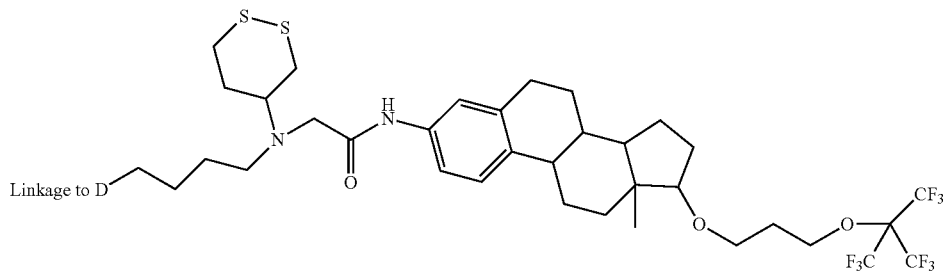

Formula (XI)

Gene silencing was assessed at 96 hours of incubation. At that time-point, cells were washed with Hank's Buffered Salt Solution (HBSS buffer; Biological Industries, Israel) and subjected to analysis. Detection and quantification of the EGFP-related fluorescent signal was performed by ELISA reader, utilizing Tecan Infinite® 200 PRO multimode reader (excitation wave length 488±4.5 nm and emission 535±10 nm). As shown in FIG. 9, while the Conjugate comprising DNA did not show any significant silencing of the EGFP gene; gene silencing was exerted by the respective Conjugate of siRNA linked to the MNMs.

Example 8

Delivery Across Cell Membranes of a Conjugate of the Invention where E has the Structure According to Formula (VIIa)

3T3 cells and C26 cells were grown and prepared as described in Example 5 above. Cells were incubated for 1, 2, and 24 hours with a Conjugate comprising a 58-mer double-stranded (ds)DNA, linked to Cy3 fluorophore, and to two E moieties according to Formula (VIIa) wherein g=4. Two concentrations of the Conjugate were tested: 40 nM and 100 nM. Analysis comprised fluorescent microscopy, and signal quantification by ELISA reader, as described in Example 5 above. An identical 58-mer dsDNA, not linked to E moieties, served as Control.

Fluorescent detection of the Conjugate within the cells was possible already after one hour. Signal was obtained, as desired, in the cytoplasm. Signal intensity marked increased by 2 hours, with additional augmentation by 24 hours of incubation. Uptake was very clearly measured by the ELISA reader. The ratios of signal intensity of the Conjugate versus the respective control dsDNA, devoid of the MNMs were, for the C26 cells: 352- and 320-fold; while for the 3T3, ratios were 104-, and 101-fold, for concentrations of 40 nM and 100 nM, respectively. Therefore, for both cell types, the Conjugate of the invention enabled highly efficient delivery The mechanism is presented in a non-limiting manner. The Conjugate has a disulfide moiety within a six-member ring. Due to the oxidative conditions that prevail in the extracellular space, this ring will manifest stability in the plasma and extracellular space. By contrast, within the cells, the Conjugate will be subjected to reductive ambient conditions, provided by the high glutathione levels in the cytoplasm. Consequentially, there is cleavage of the disulfide bond, resulting in free thiol groups. Based on analogy to other disulfide molecules the pKa values of the free thiol groups are anticipated to be about 8 and 9. Considering the physiological intracellular pH, being about 7, the vast majority of the thiol groups generated upon cleavage of the disulfide bond, at any time, about 10-20% of the molecules will be as free thiol groups (—SH), and not as the respective nucleophilic thiolate (—S⁻). The Conjugate according to Formula (XI) comprises an aromatic amide group. Importantly, this group is linked to the phenolic ring of estradiol (Ring A), which is therefore considered to be a good leaving group. Strategically, the amide carbonyl group is located five and four atoms away from the thiol groups. Similar to its action in catalysis of proteolysis in cysteine proteases, a nucleophilic action in attacking the carbonyl carbon atom of the amide group, leading to cleavage of the estradiol moiety. This action therefore selectively liberates the cargo drug (D) in the cytoplasm. In the case that D is, for example, an siRNA or a Dicer Substrate, this will lead to entrapment of the highly negatively-charged oligonucleotide in the cytoplasm, ready to interact in situ with the RNA-inducible silencing complex (RISC), in order to exert its gene silencing activity.

This mechanism is described in FIG. 10, where I. represents the intact Conjugate n the extracellular space; II. represents the cleavage of the disulfide bonfd in the reductive cytoplasmatic millieu; III. represents activation of the thiol into the thiolate, in a pka-dependent process; IV. represents nucleophilic attack of the thiolate on the carbonyl moiety of the amide group; and V. represents the consequent cleavage of the Conjugate.

The invention claimed is:

1. A method for delivery of a drug across biological membranes, the method comprising utilization of a Conjugate, having the structure as set forth in Formula (I):

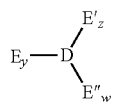

Formula (I)

wherein:
D is a drug to be delivered across biological membranes, selected from a group consisting of a protein, and a native or modified, single-stranded or double-stranded DNA or RNA, siRNA or ASO;

y, z and w are each an integer, independently selected from 0, 1, 2, 3, 4, 5, 6; wherein at least one of y, z or w is different from 0;

E, E', or E" can be the same or different, each having the structure as set forth in general Formula (II):

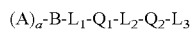

Formula (II)

wherein B is a steroid moiety selected from the group consisting of cholesterol, bile acid, estradiol, estriol; and any combination thereof; wherein B is optionally further substituted by one or more groups selected from the group consisting of:

linear $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl;

linear $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene;

$C_5$, $C_6$, $C_7$, $C_8$, $C_9$, $C_{10}$, $C_{11}$, $C_{12}$, $C_{13}$, $C_{14}$ aryl or heteroaryl;

wherein B is optionally substituted by a hydroxyl, amine, or thiol;

$Q_1$ and $Q_2$ are each independently an optionally cleavable group, selected from null, ester, thio-ester, amide [—C(=O)—NH— or —NH—C(=O)—], carbamate [—O—C(=O)—NH— or —NH—C(=O)—O—], urea [—NH—C(=O)—NH—], disulfide [—(S—S)—], ether [—O—], imidazole, triazole, analogs of BAPTA and EGTA; and any combinations thereof;

$L_1$ and $L_2$ are each independently selected from null or $L_1$, $L_2$ and $L_3$ are each independently selected from the group consisting of:

linear $C_1, C_2, C_3, C_4, C_5, C_6, C_7, C_8, C_9, C_{10}, C_{11}, C_{12}, C_{13}$ or $C_{14}$, alkyl, cyclic or branched $C_3, C_4, C_5, C_6, C_7, C_8, C_9, C_{10}, C_{11}, C_{12}, C_{13}, C_{14}$, alkyl or heteroalkyl;

linear, $C_2, C_3, C_4, C_5, C_6, C_7, C_8, C_9, C_{10}, C_{11}, C_{12}, C_{13}$ or $C_{14}$ alkyl, cyclic or branched $C_3, C_4, C_5, C_6, C_7, C_8, C_9, C_{10}, C_{11}, C_{12}, C_{13}, C_{14}$ alkylene or heteroalkylene;

$C_5, C_6, C_7, C_8, C_9, C_{10}, C_{11}, C_{12}, C_{13}$ or $C_{14}$ aryl or heteroaryl;

$-(O-CH_2-CH_2)_u-$, wherein u is an integer of 1, 2, 3, 4 or 5;

nucleoside, nucleotide; imidazole, azide, acetylene; and any combinations thereof;

wherein each group is optionally substituted by one or more hydroxyl, amine, or thiol;

wherein each of $Q_1, Q_2, L_1, L_2$ and $L_3$ is optionally an initiator group, selected from $C_4, C_5, C_6$-1,2-dithiocycloalkyl(1,2-dithiocyclo-butane; 1,2-dithiocyclo-pentane; 1,2-dithiocyclohexane; 1,2-dithiocycloheptane); γ-Lactam (5 atoms amide ring), δ-Lactam (6 atoms amide ring) or ϵ-Lactam (7 atoms amide ring); γ-butyrolactone (5 atoms ester ring), δ-valerolactone (6 atoms ester ring) or ϵ-caprolactone (7 atoms ester ring); an amine group or both an initiator group and an amine group;

A is selected from the group consisting of Formulae (III), Formula (IV), Formula (V) and Formula (VI):

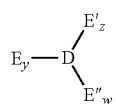

Formula (III)

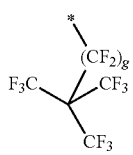

Formula (IV)

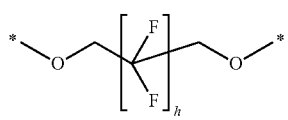

Formula (V)

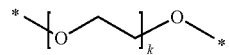

Formula (VI)

M is selected from $-O-$ or $-CH_2-$; and g, h and k are each individually an integer selected from the group consisting of 0, 1, 2, 3, 4, 5, 6, 7, 8, 9, 10, 11, 12, 13, 14, 15 and 16; * is $-H$, or a point of linkage to B; a is an integer, selected from 1, 2, 3 or 4.

2. A method according to claim 1, wherein y=1, z=o and w=0; or y=1, z=1 and w=0.

3. A method for delivery of a drug across biological membranes, the method comprising utilization of a Conjugate, having the structure as set forth in Formula (I):

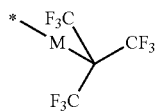

Formula (I)

wherein:

D is a drug to be delivered across biological membranes, selected from a group consisting of a protein, and a native or modified, single-stranded or double-stranded DNA or RNA, siRNA or ASO;

y, z and w are each an integer, independently selected from 0, 1, 2, 3, 4, 5, 6; wherein at least one of y, z or w is different from 0;

E, E' or E" has the structure as set forth in Formula (VII):

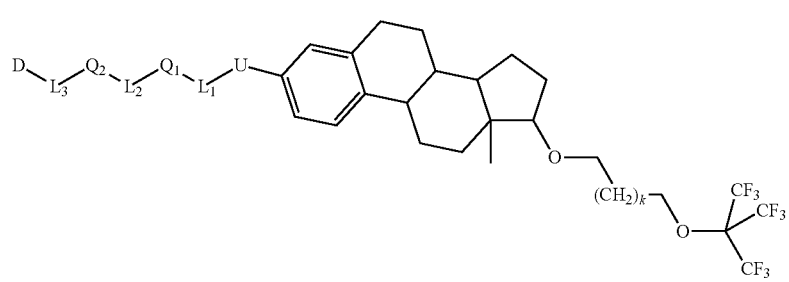

Formula (VII)

wherein k is an integer, selected from 0, 1, 2, 3, and 4; U is selected from null, O, N and NH; and wherein B is a steroid moiety selected from the group consisting of cholesterol, bile acid, estradiol, estriol; and any combination thereof; wherein B is optionally further substituted by one or more groups selected from the group consisting of:

linear $C_1, C_2, C_3, C_4, C_5, C_6, C_7, C_8, C_9, C_{10}, C_{11}, C_{12}, C_{13}, C_{14}$ alkyl, cyclic or branched $C_3, C_4, C_5, C_6, C_7, C_8, C_9, C_{10}, C_{11}, C_{12}, C_{13}, C_{14}$, alkyl or hetero-alkyl;

linear, $C_2, C_3, C_4, C_5, C_6, C_7, C_8, C_9, C_{10}, C_{11}, C_{12}, C_{13}, C_{14}$ alkyl, cyclic or branched $C_3, C_4, C_5, C_6, C_7, C_8, C_9, C_{10}, C_{11}, C_{12}, C_{13}, C_{14}$ alkylene or heteroalkylene;

$C_5$, $C_6$, $C_7$, $C_8$, $C_9$, $C_{10}$, $C_{11}$, $C_{12}$, $C_{13}$, $C_{14}$ aryl or heteroaryl;

wherein B is optionally substituted by a hydroxyl, amine, or thiol;

$Q_1$ and $Q_2$ are each independently an optionally cleavable group, selected from null, ester, thio-ester, amide [—C(=O)—NH— or —NH—C(=O)—], carbamate [—O—C(=O)—NH— or —NH—C(=O)—O—], urea [—NH—C(=O)—NH—], disulfide [—(S—S)—], ether [—O—], imidazole, triazole, analogs of BAPTA and EGTA; and any combinations thereof;

$L_1$ and $L_2$ are each independently selected from null or $L_1$, $L_2$ and $L_3$ are each independently selected from the group consisting of:

linear, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl, cyclic or branched $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl;

linear, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene;

$C_5$, $C_6$, $C_7$, $C_8$, $C_9$, $C_{10}$, $C_{11}$, $C_{12}$, $C_{13}$ or $C_{14}$ aryl or heteroaryl;

—(O—CH$_2$—CH$_2$)$_u$—, wherein u is an integer of 1, 2, 3, 4 or 5;

nucleoside, nucleotide; imidazole, azide, acetylene; and any combinations thereof;

wherein each group is optionally substituted by one or more hydroxyl, amine, or thiol;

wherein each of $Q_1$, $Q_2$, $L_1$, $L_2$ and $L_3$ is optionally an initiator group, selected from $C_4$, $C_5$,$C_6$-1,2-dithiocloalkyl(1,2-dithiocyclo-butane; 1,2-dithiocyclo-pentane; 1,2-dithiocyclohexane; 1,2-dithiocycloheptane);

γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); an amine group; or both an initiator group and an amine group.

4. A method according to claim 3, wherein k=1.

5. A method according to claim 3, wherein $L_1$ and $L_2$ are each individually selected form null or $L_1$, $L_2$ and $L_3$ are each individually selected from null and a linear $C_1$, $C_2$, $C_3$, $C_4$, $C_5$, $C_6$, $C_7$, $C_8$ cyclic or branched $C_3$, $C_4$, $C_5$, $C_6$, $C_7$, $C_8$ hydrocarbon chain; $L_1$, $L_2$ and $L_3$ can be the same or different.

6. A method according to claim 3, wherein $Q_1$ or $Q_2$ is selected from the group consisting of an amide group, an ester, a carbamate, a disulfide, imidazole; and any combination thereof.

7. A method according to claim 3, wherein $L_1$, $L_2$ or $L_3$ is 1,2-dithiocyclo-butane, optionally linked to an amide or amine group.

8. A method according to claim 1, wherein E, E' or E" have the structure as set forth in Formulae (VIIa):

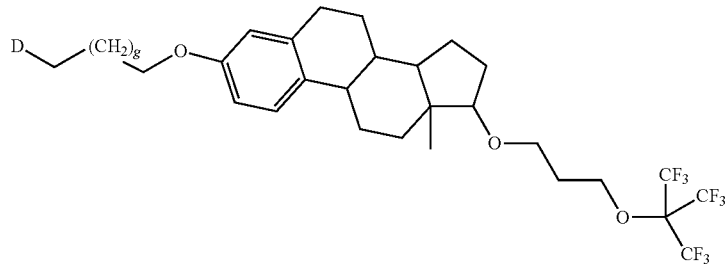

Formula (VIIa)

wherein g stands for an integer of 0, 1, 2, 3, 4, 5, 6, 7, 8, 9, 10, 11, 12, 13, 14.

9. A method according to claim 8, wherein g=2.

10. A method according to claim 1, wherein E, E' or E" have the structure as set forth in Formula (VIII):

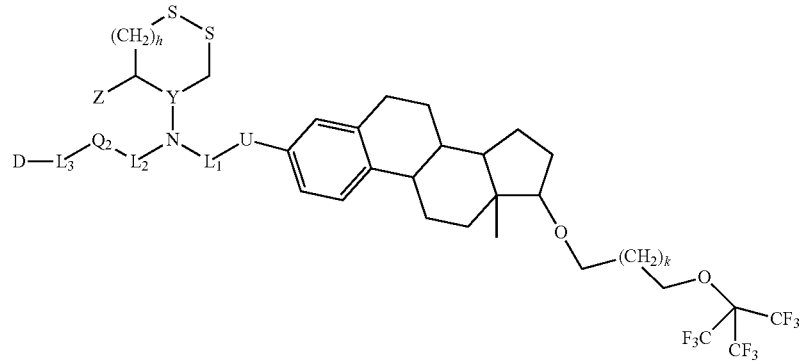

Formula (VIII)

where k stands for an integer, selected from the group consisting of 0, 1, 2, 3, 4, 5, 6, 7, 8, 9, 10, 11, 12, 13, 14, 15 and 16; h stands for an integer, selected from the group consisting of 0, 1, 2, 3 and 4; U is selected from null, O, N or NH; Z is selected from hydrogen, hydroxyl and amine groups; Y is selected from —CH— and a nitrogen atom.

11. A method according to claim 10, wherein k=1, and h=1.

12. A method according to claim 1, wherein E, E' or E" have the structure as set forth in Formula (IX):

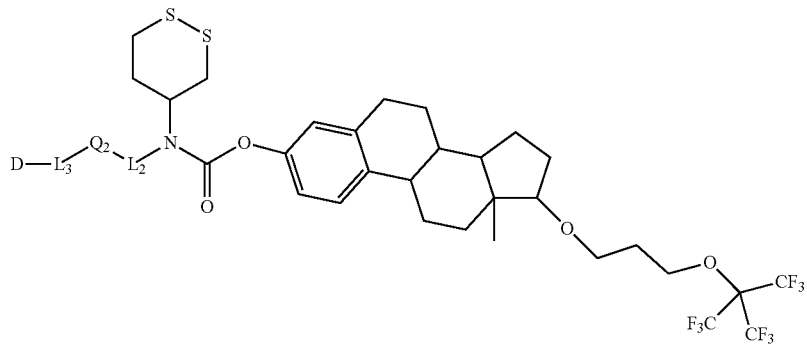

Formula (IX)

or has the conjugate structure as set forth in Formula (X):

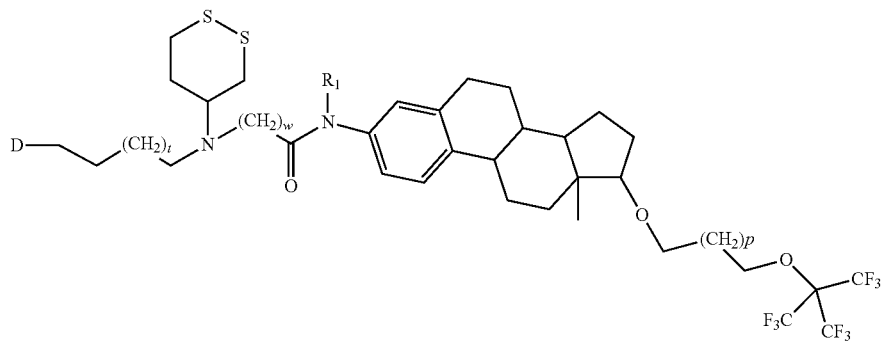

Formula (X)

wherein w stands for an integer of 0, 1, 2 or 3; t stands for an integer of 0, 1, 2, 3, 4, 5, 6, 7, 8, 9, 10, 11, 12, 13 or 14; p stands for an integer of 0, 1, 2 or 3; $R_1$ stands for hydrogen, or an alkyl group of 1, 2 or 3 carbon atoms; or has the conjugate structure as set forth in Formula (XI):

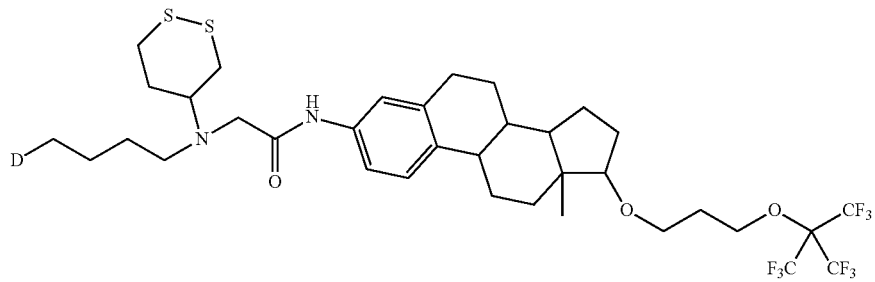

Formula (XI)

or has the conjugate structure as set forth in Formula (XII):
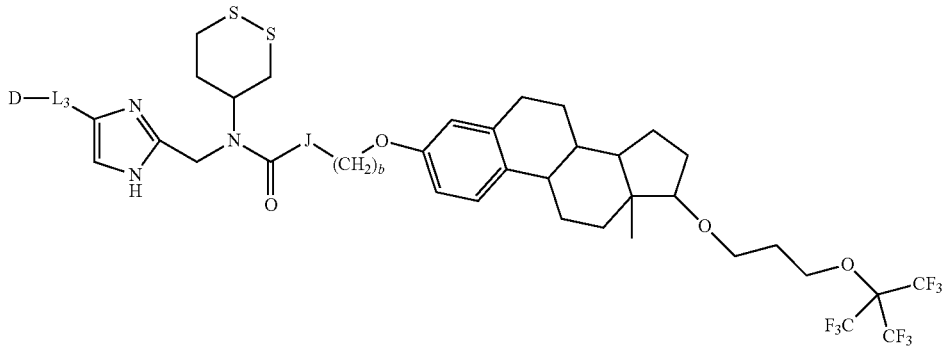
Formula (XII)
wherein b stands for an integer of 0, 1, 2, 3, 4, 5, 6, 7, 8 or 9; J is selected from null, nitrogen or an oxygen atom;
or has the conjugate structure as set forth in Formula (XIII):
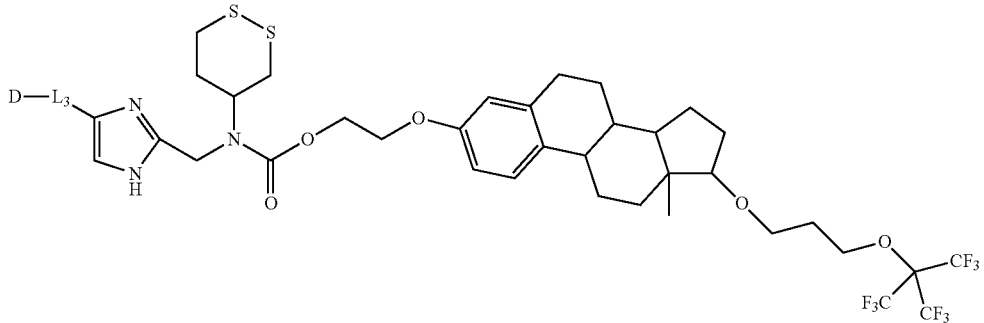
Formula (XIII)
or has the conjugate structure as set forth in-Formula (XIV):
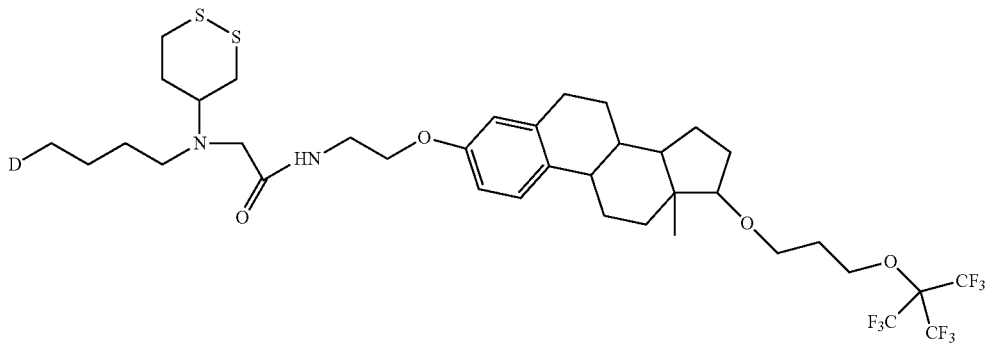
Formula (XIV)

or has the conjugate structure as set forth in Formula (XV):

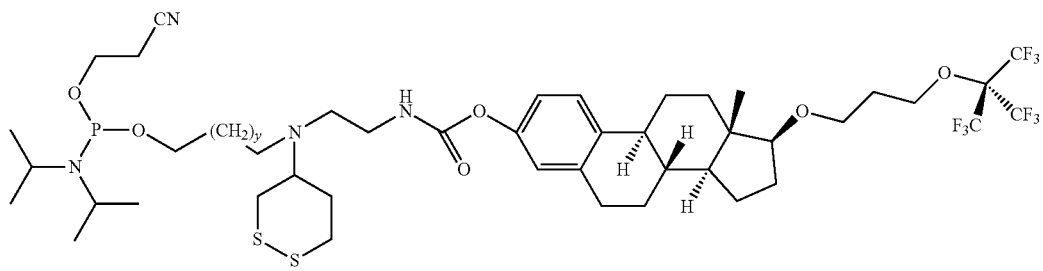

Formula (XV)

where y stands for an integer, selected from the group consisting of 0, 1, 2, 3, 4, 5, 6, 7, 8, 9, 10, 11 and 12;
or has the conjugate structure as set forth in Formula (XVI):

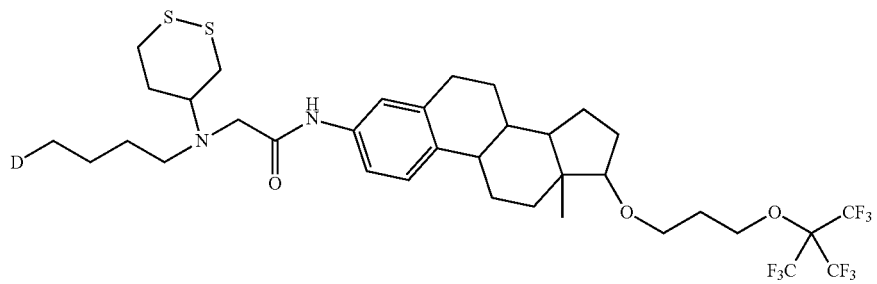

Formula (XVI)

or has the conjugate structure as set forth in Formula (XVII):

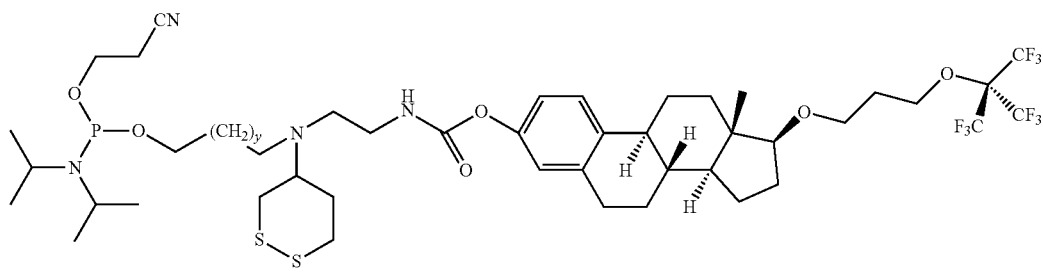

Formula (XVII)

where y stands for an integer, selected from the group consisting of 0, 1, 2, 3, 4, 5, 6, 7, 8, 9, 10, 11 and 12. In a preferred embodiment, y=1.

13. A conjugate according to Formula (I):

$$E_y\text{—}D\begin{matrix}E'_z\\ \diagup\\ \diagdown\\ E''_w\end{matrix}$$

Formula (I)

wherein:
D is a drug to be delivered across biological membranes, selected from a group consisting of a protein, and a native or modified, single-stranded or double-stranded DNA or RNA, siRNA or ASO;

y, z and w are each an integer, independently selected from 0, 1, 2, 3, 4, 5, 6; wherein at least one of y, z or w is different from 0;

E, E', or E" can be the same or different, each having the structure as set forth in general Formula (II):

$(A)_a\text{-}B\text{-}L_1\text{-}Q_1\text{-}L_2\text{-}Q_2\text{-}L_3$  Formula (II)

wherein B is a steroid moiety selected from the group consisting of cholesterol, bile acid, estradiol, estriol; and any combination thereof; wherein B is optionally further substituted by one or more groups selected from the group consisting of:
linear $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$ alkyl or hetero-alkyl;
linear, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene;

$C_5$, $C_6$, $C_7$, $C_8$, $C_9$, $C_{10}$, $C_{11}$, $C_{12}$, $C_{13}$, $C_{14}$ aryl or heteroaryl;

wherein B is optionally substituted by a hydroxyl, amine, or thiol;

$Q_1$ and $Q_2$ are each independently an optionally cleavable group, selected from null, ester, thio-ester, amide [—C(=O)—NH— or —NH—C(=O)—], carbamate [—O—C(=O)—NH— or —NH—C(=O)—O—], urea [—NH—C(=O)—NH—], disulfide [—(S—S)—], ether [—O—], imidazole, triazole, analogs of BAPTA and EGTA; and any combinations thereof;

$L_1$ and $L_2$ are each independently selected from null or $L_1$, $L_2$ and $L_3$ are each independently selected from the group consisting of:

linear, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl, cyclic or branched $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl;

linear $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl, cyclic or branched $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene;

$C_5$, $C_6$, $C_7$, $C_8$, $C_9$, $C_{10}$, $C_{11}$, $C_{12}$, $C_{13}$ or $C_{14}$ aryl or heteroaryl;

—(O—CH$_2$—CH$_2$)$_u$—, wherein u is an integer of 1, 2, 3, 4 or 5;

nucleoside, nucleotide; imidazole, azide, acetylene; and any combinations thereof;

wherein each group is optionally substituted by one or more hydroxyl, amine, or thiol;

wherein each of $Q_1$, $Q_2$, $L_1$, $L_2$ and $L_3$ is optionally an initiator group, selected from $C_4$, $C_5$,$C_6$-1,2-dithiocycloalkyl(1,2-dithiocyclo-butane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); an amine group; or both an initiator group and an amine group;

A is selected from the group consisting of Formulae (III), Formula (IV), Formula (V) and Formula (VI):

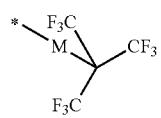

Formula (III)

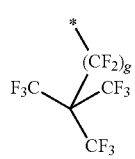

Formula (IV)

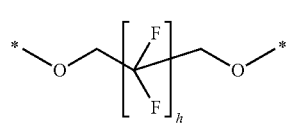

Formula (V)

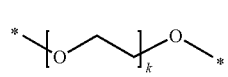

Formula (VI)

M is selected from —O— or -CH$_2$-; and g, h and k are each individually an integer selected from the group consisting of 0, 1, 2, 3, 4, 5, 6, 7, 8, 9, 10, 11, 12, 13, 14, 15 and 16; * is —H, or a point of linkage to B; a is an integer, selected from 1, 2, 3 or 4.

14. A conjugate according to claim 13, wherein the drug is a macromolecule, selected from the group consisting of siRNA, ASO and a therapeutic protein.

15. A conjugate according to claim 14, wherein the therapeutic protein comprises a CRISPR protein.

16. A conjugate according to claim 15, wherein the CRISPR protein is Cas9 protein.

17. A pharmaceutical composition, comprising a Conjugate according to claim 13 and a pharmaceutically-acceptable salt or carrier.

18. A method for delivery of a drug into biological cells, wherein said cells are in culture, or in a living animal or a human subject; the method comprising contacting the cells with a Conjugate according to claim 13.

19. The method according to claim 1, where the biological membrane is selected from a group consisting of cell membranes and biological barriers, selected from the blood-brain-barrier, blood-ocular-barrier or the blood-fetal-barrier.

20. A precursor, having the structure as set forth in Formula (XVII):

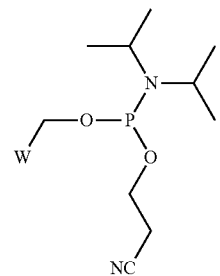

Formula (XVII)

wherein W is a moiety, selected from E, E' or E''as described in any of Formula II, VII, VIIa, VIII, IX, X, XI, XII, XIII, XIV, XV or XVI;

wherein Formula (II) is defined as:

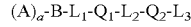

(A)$_a$-B-L$_1$-Q$_1$-L$_2$-Q$_2$-L$_3$    Formula (II)

wherein B is a steroid moiety selected from the group consisting of cholesterol, bile acid, estradiol, estriol; and any combination thereof; wherein B is optionally further substituted by one or more groups selected from the group consisting of:

linear $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl;

linear, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$alkylene or heroalkylene;

$C_5$, $C_6$, $C_7$, $C_8$, $C_9$, $C_{10}$, $C_{11}$, $C_{12}$, $C_{13}$, $C_{14}$ aryl or heteroaryl;

wherein B is optionally substituted by a hydroxyl, amine, or thiol;

$Q_1$ and $Q_2$ are each independently an optionally cleavable group, selected from null, ester, thio-ester, amide [—C(=O)—NH— or —NH—C(=O)—], carbamate [—O—C(=O)—NH— or —NH—C(=O)—O—], urea [—NH—C(=O)—NH—], disulfide [—(S—S)—], ether [—O—], imidazole, triazole, analogs of BAPTA and EGTA; and any combinations thereof;

$L_1$ and $L_2$ are each independently selected from null or $L_1$, $L_2$ and $L_3$ are each independently selected from the group consisting of:

linear, $C_1, C_2, C_3, C_4, C_5, C_6, C_7, C_8, C_9, C_{10}, C_{11}, C_{12}, C_{13}, C_{14}$, alkyl, cyclic or branched $C_3, C_4, C_5, C_6, C_7, C_8, C_9, C_{10}, C_{11}, C_{12}, C_{13}, C_{14}$, alkyl or heteroalkyl;

linear $C_2, C_3, C_4, C_5, C_6, C_7, C_8, C_9, C_{10}, C_{11}, C_{12}, C_{13}, C_{14}$, alkyl, cyclic or branched $C_3, C_4, C_5, C_6, C_7, C_8, C_9, C_{10}, C_{11}, C_{12}, C_{13}$ or $C_{14}$ alkylene or heteroalkylene;

$C_5, C_6, C_7, C_8, C_9, C_{10}, C_{11}, C_{12}, C_{13}$ or $C_{14}$ aryl or heteroaryl;

—(O—CH$_2$—CH$_2$)$_u$—, wherein u is an integer of 1, 2, 3, 4 or 5;

nucleoside, nucleotide; imidazole, azide, acetylene; and any combinations thereof;

wherein each group is optionally substituted by one or more hydroxyl, amine, or thiol;

wherein each of $Q_1, Q_2, L_1, L_2$ and $L_3$ is optionally an initiator group, selected from $C_4, C_5, C_6$-1,2-dithiocycloalkyl(1,2-dithiocyclo-butane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); an amine group; or both an initiator group and an amine group;

A is selected from the group consisting of Formulae (III), Formula (IV), Formula (V) and Formula (VI):

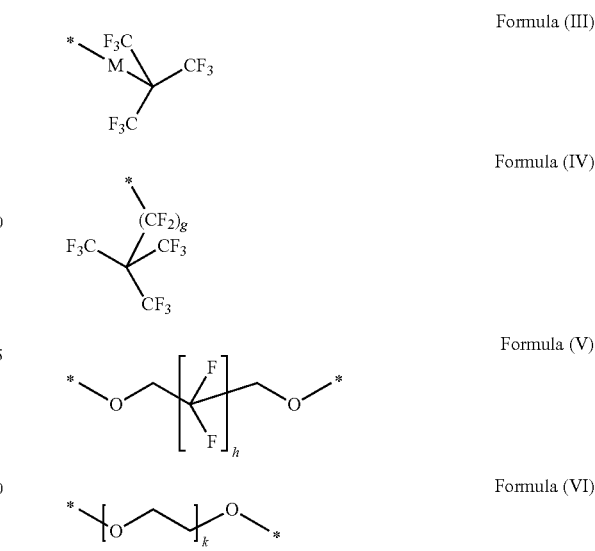

M is selected from —O— or —CH$_2$-; and g, h and k are each individually an integer selected from the group consisting of 0, 1, 2, 3, 4, 5, 6, 7, 8, 9, 10, 11, 12, 13, 14, 15 and 16; * is —H, or a point of linkage to B; a is an integer, selected from 1, 2, 3 or 4 and wherein Formula VII is defined as:

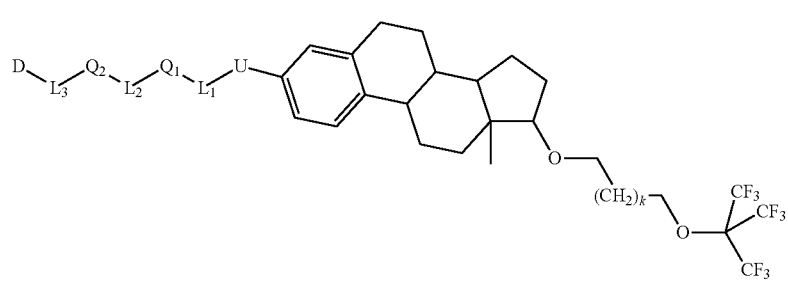

wherein k is an integer, selected from 0, 1, 2, 3, and 4; U is selected from null, O, N and NH;

D is a drug to be delivered across biological membranes, selected from a group consisting of a protein, and a native or modified, single-stranded or double-stranded DNA or RNA, siRNA or ASO;

Formulae (VIIa) is defined as:

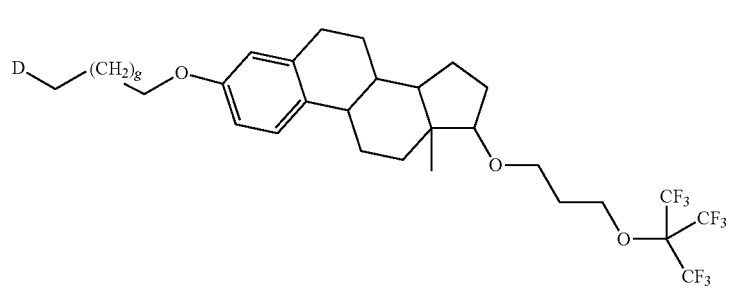

wherein g stands for an integer of 0, 1, 2, 3, 4, 5, 6, 7, 8, 9, 10, 11, 12, 13, 14 Formula (VIII) is defined as:

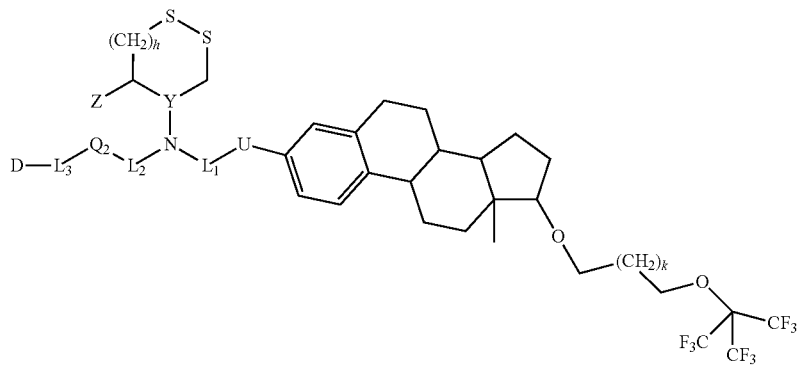

Formula (VIII)

where k stands for an integer, selected from the group consisting of 0, 1, 2, 3, 4, 5, 6, 7, 8, 9, 10, 11, 12, 13, 14, 15 and 16; h stands for an integer, selected from the group consisting of 0, 1, 2, 3 and 4; U is selected from null, O, N or NH; Z is selected from hydrogen, hydroxyl and amine groups; Y is selected from —CH— and a nitrogen atom Formula (IX) is defined as:

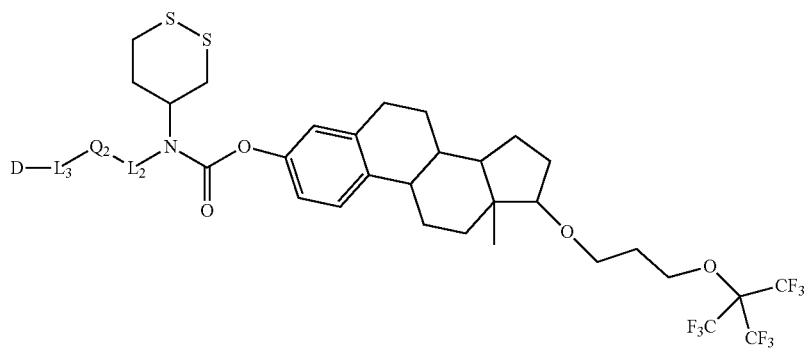

Formula (IX)

Formula (X) is defined as:

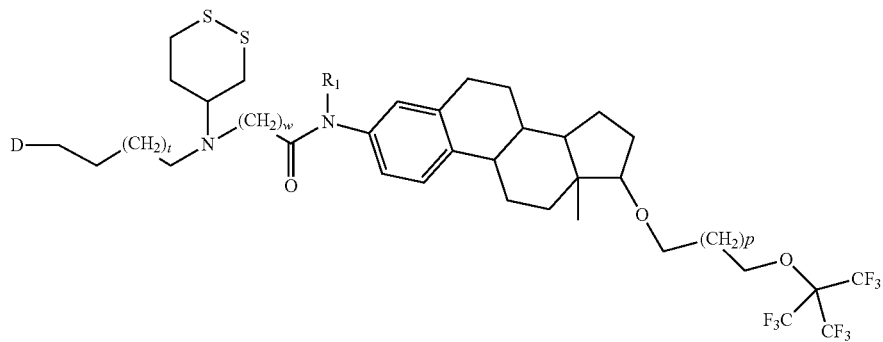

Formula (X)

wherein w stands for an integer of 0, 1, 2 or 3; t stands for an integer of 0, 1, 2, 3, 4, 5, 6, 7, 8, 9, 10, 11, 12, 13 or 14; p stands for an integer of 0, 1, 2 or 3; $R_1$ stands for hydrogen, or an alkyl group of 1, 2 or 3 carbon atoms;

Formula (XI) is defined as:
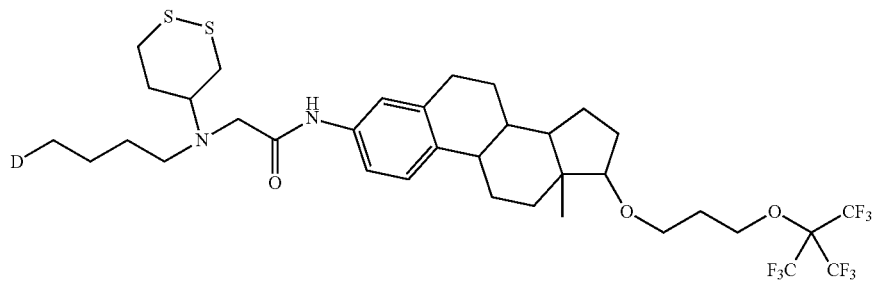
Formula (XI)
Formula (XII) is defined as:
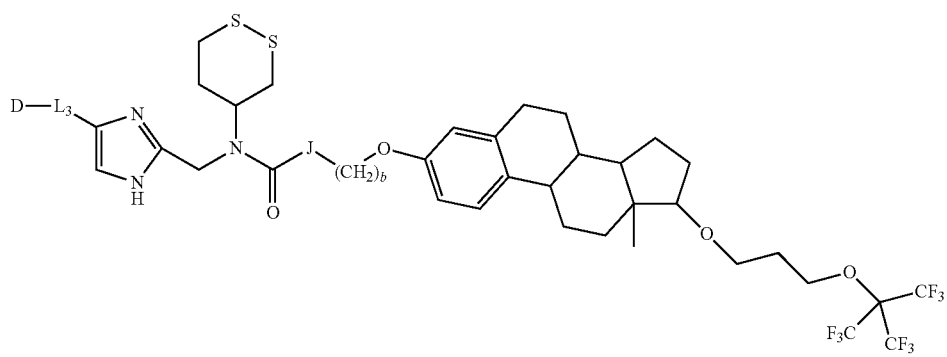
Formula (XII)
wherein b stands for an integer of 0, 1, 2, 3, 4, 5, 6, 7, 8 or 9; J is selected from null, nitrogen or an oxygen atom;
Formula (XIII) is defined as:
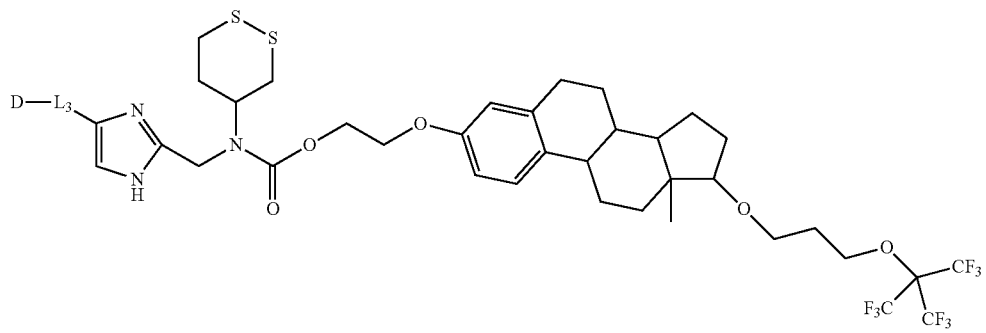
Formula (XIII)

Formula (XIV) is defined as:

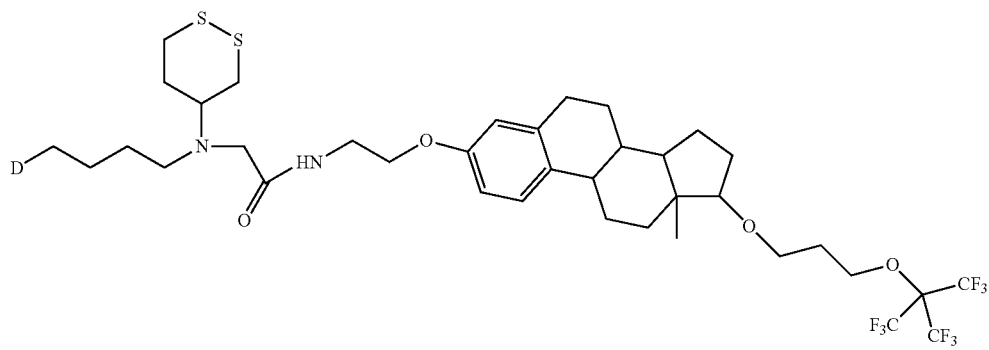

Formula (XIV)

Formula (XV) is defined as:

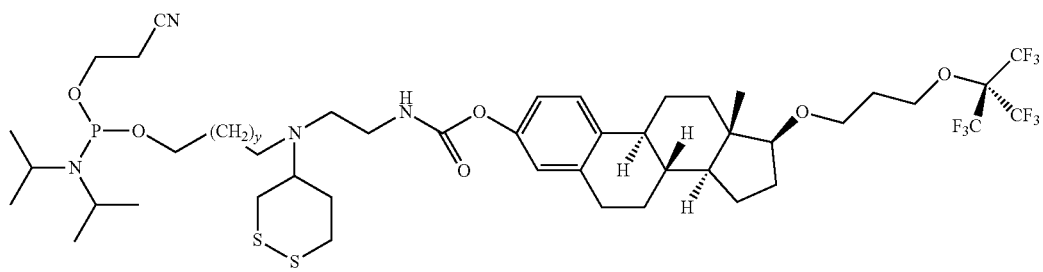

Formula (XV)

where y stands for an integer, selected from the group consisting of 0, 1, 2, 3, 4, 5, 6, 7, 8, 9, 10, 11 and 12;
Formula (XVI) is defined as:

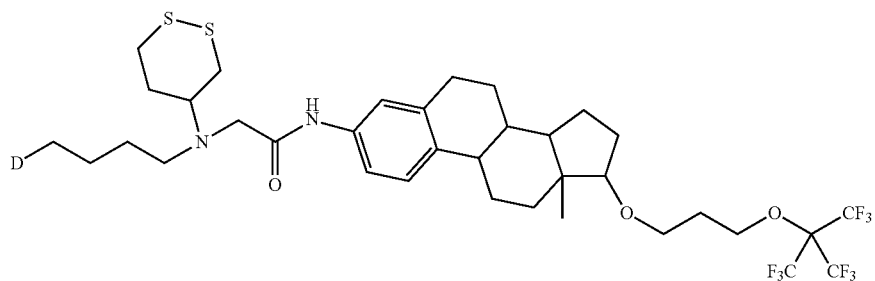

Formula (XVI)

or has a structure as set forth in Formula (XVIII):

Formula (XVIII)

```
      ┌─ODMTr
      │
   G  O
      ║
      CPG
``` wherein G is a moiety, selected from E, E' or E" as described in any of Formula II, VII, VIIa, VIII, IX, X, XI, XII, XIII, XIV, XV or XVI and where DMT (dimethoxytrityl) is a protecting group for a hydroxyl; and CPG is Controlled Pore Glass.

21. A precursor, having the structure as set forth in any of Formula II, VII, VIIa, VIII, IX, X, XI, XII, XIII, XIV, XV or XVI, wherein D is selected from phosphoroamidate, an activated ester, azide or acetylene and wherein Formula (II) is defined as:

$(A)_a\text{-B-L}_1\text{-Q}_1\text{-L}_2\text{-Q}_2\text{-L}_3$  Formula (II)

wherein B is a steroid moiety selected from the group consisting of cholesterol, bile acid, estradiol, estriol; and any combination thereof; wherein B is optionally further substituted by one or more groups selected from the group consisting of:

linear $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl;

linear, $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkyl, cyclic or branched $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene;

$C_5$, $C_6$, $C_7$, $C_8$, $C_9$, $C_{10}$, $C_{11}$, $C_{12}$, $C_{13}$, $C_{14}$ aryl or heteroaryl;

wherein B is optionally substituted by a hydroxyl, amine, or thiol;

$Q_1$ and $Q_2$ are each independently an optionally cleavable group, selected from null, ester, thio-ester, amide [—C(=O)—NH— or —NH—C(=O)—], carbamate [—O—C(=O)—NH— or —NH—C(=O)—O—], urea [—NH—C(=O)—NH—], disulfide [—(S—S)—], ether [—O—], imidazole, triazole, analogs of BAPTA and EGTA; and any combinations thereof;

$L_1$ and $L_2$ are each independently selected from null or $L_1$, $L_2$ and $L_3$ are each independently selected from the group consisting of:

linear $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl, cyclic or branched $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl;

linear $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl, cyclic or branched $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene;

$C_5$, $C_6$, $C_7$, $C_8$, $C_9$, $C_{10}$, $C_{11}$, $C_{12}$, $C_{13}$ or $C_{14}$ aryl or heteroaryl;

—(O—$CH_2$—$CH_2$)$_u$—, wherein u is an integer of 1, 2, 3, 4 or 5;

nucleoside, nucleotide; imidazole, azide, acetylene; and any combinations thereof;

wherein each group is optionally substituted by one or more hydroxyl, amine, or thiol;

wherein each of $Q_1$, $Q_2$, $L_1$, $L_2$ and $L_3$ is optionally an initiator group, selected from $C_4$, $C_5$, $C_6$-1,2-dithiocycloalkyl(1,2-dithiocyclo-butane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); an amine group; or both an initiator group and an amine group;

A is selected from the group consisting of Formulae (III), Formula (IV), Formula (V) and Formula (VI):

Formula (III)

Formula (IV)

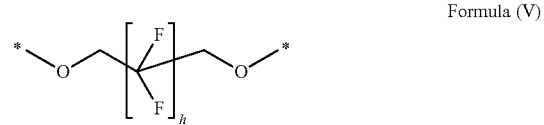

Formula (V)

Formula (VI)

M is selected from —O— or —$CH_2$-; and g, h and k are each individually an integer selected from the group consisting of 0, 1, 2, 3, 4, 5, 6, 7, 8, 9, 10, 11, 12, 13, 14, 15 and 16; * is —H, or a point of linkage to B; a is an integer, selected from 1, 2, 3 or 4 and wherein Formula VII is defined as:

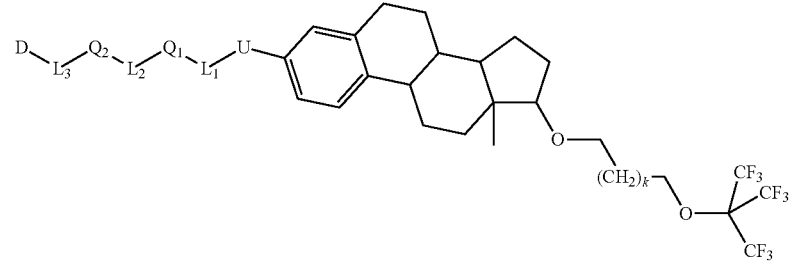

Formula (VII)

wherein k is an integer, selected from 0, 1, 2, 3, and 4; U is selected from null, O, N and NH Formulae (VIIa) is defined as:

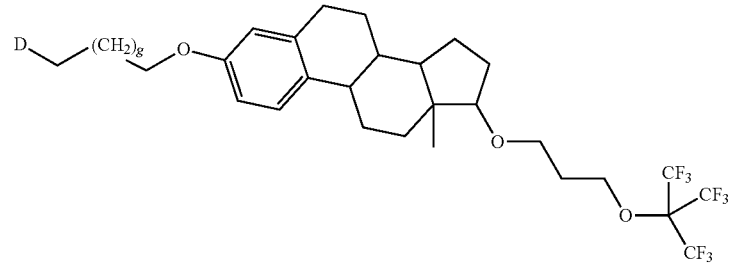

Formula (VIIa)

wherein g stands for an integer of 0, 1, 2, 3, 4, 5, 6, 7, 8, 9, 10, 11, 12, 13, 14
Formula (VIII) is defined as:

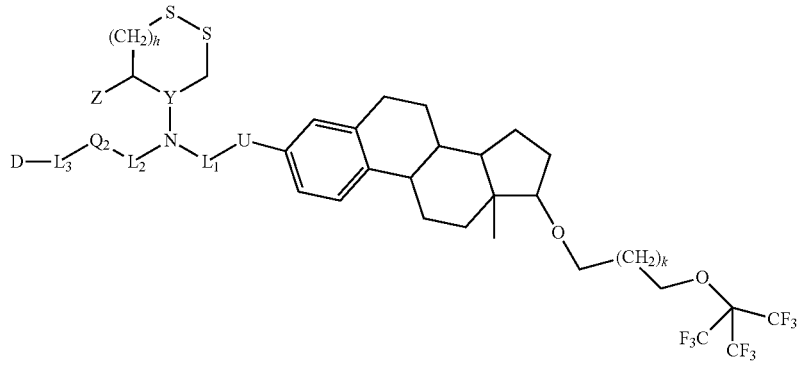

Formula (VIII)

where k stands for an integer, selected from the group consisting of 0, 1, 2, 3, 4, 5, 6, 7, 8, 9, 10, 11, 12, 13, 14, 15 and 16; h stands for an integer, selected from the group consisting of 0, 1, 2, 3 and 4; U is selected from null, O, N or NH; Z is selected from hydrogen, hydroxyl and amine groups; Y is selected from —CH— and a nitrogen atom Formula (IX) is defined as:

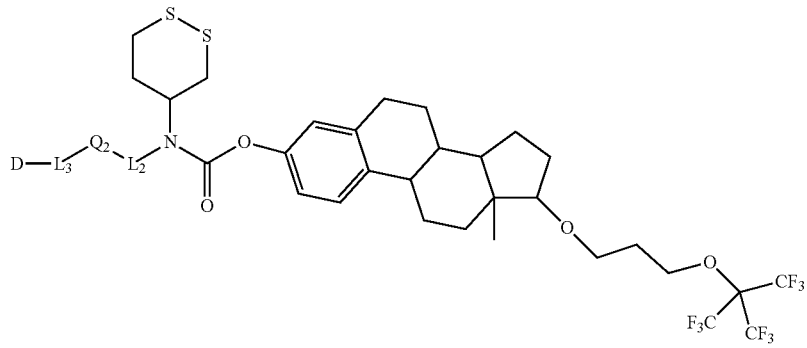

Formula (IX)

Formula (X) is defined as:

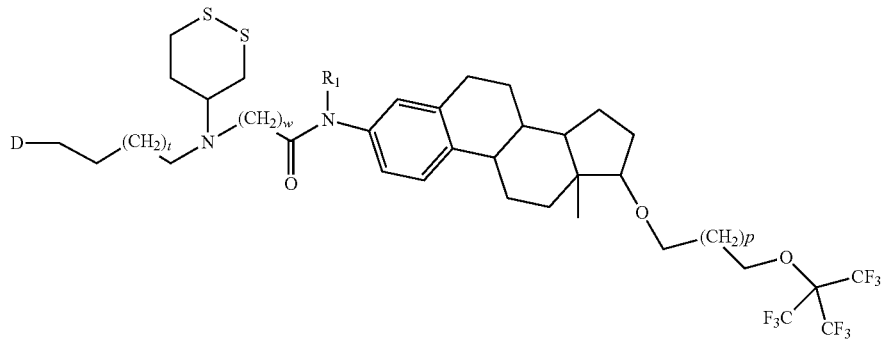

Formula (X)

wherein w stands for an integer of 0, 1, 2 or 3; t stands for an integer of 0, 1, 2, 3, 4, 5, 6, 7, 8, 9, 10, 11, 12, 13 or 14; p stands for an integer of 0, 1, 2 or 3; $R_1$ stands for hydrogen, or an alkyl group of 1, 2 or 3 carbon atoms;

Formula (XI) is defined as:
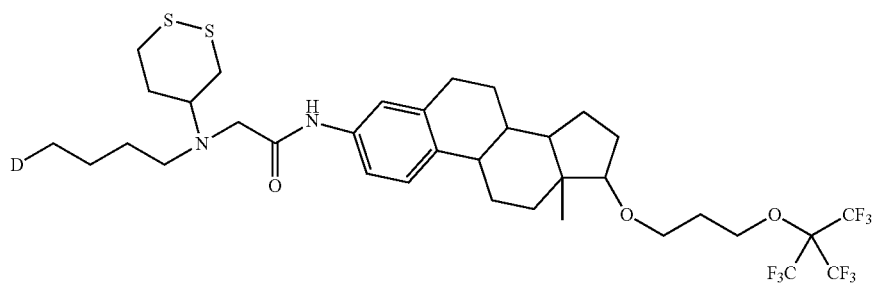
Formula (XI)
Formula (XII) is defined as:
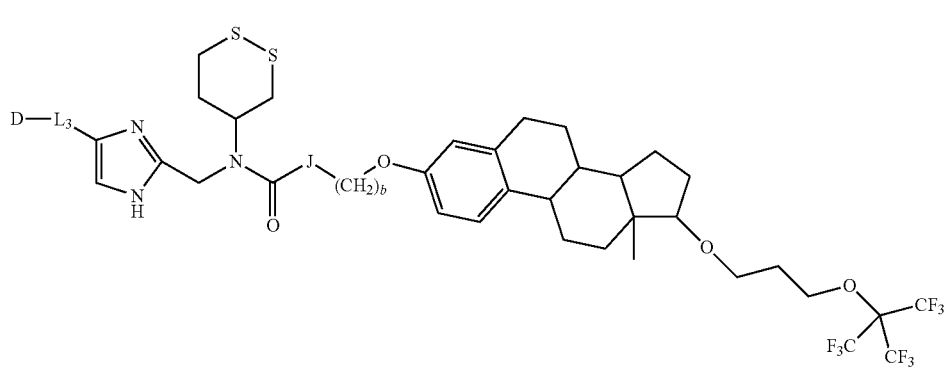
Formula (XII)
wherein b stands for an integer of 0, 1, 2, 3, 4, 5, 6, 7, 8 or 9; J is selected from null, nitrogen or an oxygen atom;
Formula (XIII) is defined as:
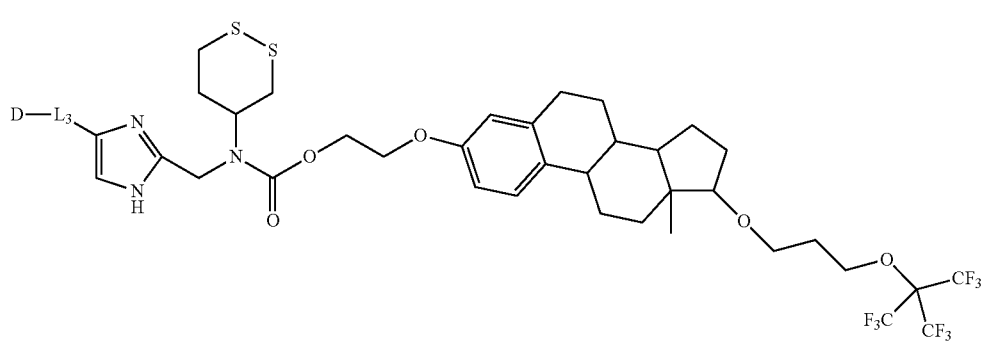
Formula (XIII)
Formula (XIV) is defined as:
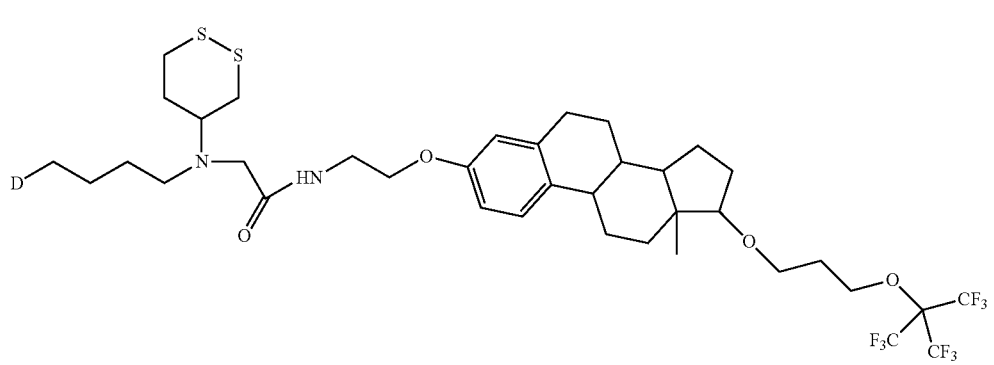
Formula (XIV)

Formula (XV) is defined as:

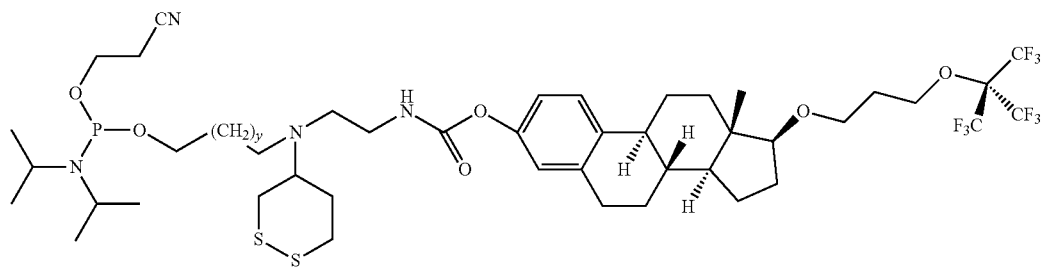

Formula (XV)

where y stands for an integer, selected from the group consisting of 0, 1, 2, 3, 4, 5, 6, 7, 8, 9, 10, 11 and 12;
Formula (XVI) is defined as:

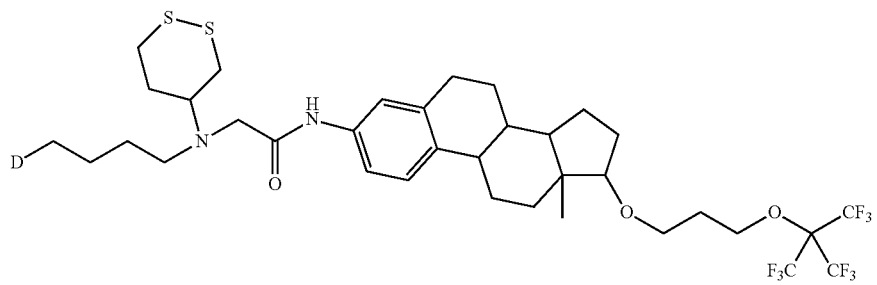

Formula (XVI)

and wherein Formula (XVIII):

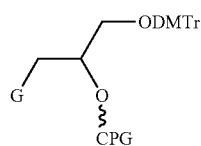

Formula (XVIII)

wherein G is a moiety, selected from E, E' or E" as described in any of Formula II, VII, VIIa, VIII, IX, X, XI, XII, XIII, XIV, XV or XVI and where DMT (dimethoxytrityl) is a protecting group for a hydroxyl; and CPG is Controlled Pore Glass.

22. The method according to claim 1, wherein the steroid moiety is selected from cholesterol, bile acid, estrogen, estradiol, and estriol.

23. A method of delivering a drug across a biological membrane, the method comprising:
conjugating at least one asymmetrically polar chemical moiety to a drug, wherein the moiety is capable of moving within the hydrophobic membrane milieu towards the membrane core, directed by the internal membrane electrical field; and
contacting the biological membrane with the conjugated-drug.

24. A method of delivering a drug across a biological membrane, the method comprising:
providing a conjugate of a drug and at least one asymmetrically polar chemical moiety, wherein the moiety is capable of moving within the hydrophobic membrane milieu towards the membrane core, directed by the internal membrane electrical field; and contacting the biological membrane with the conjugated-drug.

25. A conjugate of a drug and at least one asymmetrically polar chemical moiety, wherein the moiety is capable of moving within the hydrophobic membrane milieu towards the membrane core, directed by the internal membrane electrical field, for use in delivering a drug across a biological membrane.

26. A method according to claim 24, wherein the asymmetrically polar chemical moiety has an octanol/water partition coefficient >1.

27. A method according to claim 24, wherein the asymmetrically polar chemical moiety comprises a focused negative pole comprising at least one electronegative atom, and a dispersed positive pole.

28. A method according to claim 27, wherein
the negative pole comprises at least one electronegative atom selected from a halogen such as fluorine, or oxygen, and/or
the positive pole comprises a hydrocarbon chain(s), a steroid moiety or a combinations thereof, optionally substituted by electropositive atoms selected from silicon, boron, phosphorus and sulfur.

29. A conjugate according to claim 13, wherein E, E' or E" has the structure as set forth in Formula (VII):

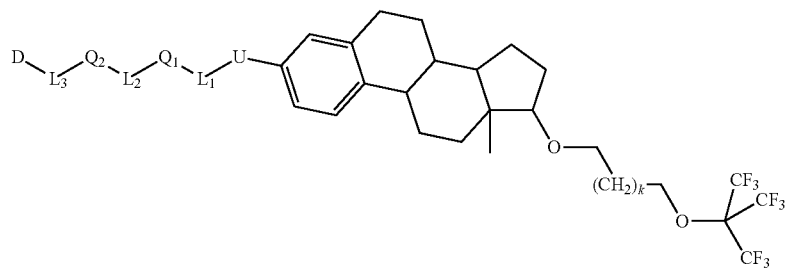
Formula (VII)
30. A pharmaceutical composition, comprising a Conjugate according to claim 29 and a pharmaceutically-acceptable salt or carrier.
* * * * *